US010626431B2

(12) United States Patent
Winge

(10) Patent No.: US 10,626,431 B2
(45) Date of Patent: Apr. 21, 2020

(54) METHOD FOR IMPROVED ISOLATION OF RECOMBINANTLY PRODUCED PROTEINS

(71) Applicant: OCTAPHARMA AG, Lachen (SE)

(72) Inventor: Stefan Winge, Arsta (SE)

(73) Assignee: OCTAPHARMA AG, Lachen (CH)

( * ) Notice: Subject to any disclaimer, the term of this patent is extended or adjusted under 35 U.S.C. 154(b) by 561 days.

(21) Appl. No.: 15/199,585

(22) Filed: Jun. 30, 2016

(65) Prior Publication Data

US 2017/0183703 A1 Jun. 29, 2017

Related U.S. Application Data

(63) Continuation of application No. 11/887,677, filed as application No. PCT/EP2006/061148 on Mar. 29, 2006, now Pat. No. 9,388,402.

(30) Foreign Application Priority Data

Mar. 29, 2005 (EP) .................................... 05102475

(51) Int. Cl.

| | |
|---|---|
| ***C12P 21/00*** | (2006.01) |
| ***C12N 15/79*** | (2006.01) |
| ***C12N 5/00*** | (2006.01) |
| ***B01D 15/08*** | (2006.01) |
| ***C12N 9/64*** | (2006.01) |
| ***C12P 21/02*** | (2006.01) |
| ***C07K 14/755*** | (2006.01) |

(52) U.S. Cl.

CPC .............. *C12P 21/00* (2013.01); *B01D 15/08* (2013.01); *C07K 14/755* (2013.01); *C12N 5/0018* (2013.01); *C12N 9/644* (2013.01); *C12N 9/647* (2013.01); *C12N 15/79* (2013.01); *C12P 21/02* (2013.01); *C12Y 304/21022* (2013.01); *Y02P 20/52* (2015.11)

(58) Field of Classification Search

None

See application file for complete search history.

(56) References Cited

U.S. PATENT DOCUMENTS

| | | | | |
|---|---|---|---|---|
| 4,770,999 A | | 9/1988 | Kaufman et al. | 435/68 |
| 4,868,112 A | | 9/1989 | Toole, Jr. | 435/68 |
| 4,980,456 A | | 12/1990 | Scandella et al. | 530/383 |
| 5,045,455 A | | 9/1991 | Kuo et al. | 435/69.6 |
| 5,122,469 A | | 6/1992 | Mather et al. | |
| 5,521,070 A | | 5/1996 | Meulien | 435/69.1 |
| 5,770,561 A | * | 6/1998 | Horwitz | C07K 14/47 514/2.2 |
| 5,789,203 A | | 8/1998 | Chapman et al. | 435/69.6 |
| 5,831,026 A | | 11/1998 | Almstedt et al. | 530/383 |
| 5,851,800 A | | 12/1998 | Adamson | 435/69.1 |
| 6,338,964 B1 | | 1/2002 | Matanguihan | 435/325 |
| 6,897,040 B2 | | 5/2005 | Morris et al. | |
| 2002/0012991 A1 | | 1/2002 | Fong et al. | |
| 2005/0227920 A1 | * | 10/2005 | Lin | C07K 14/70575 435/69.1 |

FOREIGN PATENT DOCUMENTS

| | | |
|---|---|---|
| EP | 150735 | 8/1985 |
| EP | 160457 | 11/1985 |
| EP | 232112 | 8/1987 |
| EP | 251843 | 1/1988 |
| EP | 253455 | 1/1988 |
| EP | 254076 | 1/1988 |
| EP | 265778 | 5/1988 |
| EP | 294910 | 12/1988 |
| EP | 303540 | 2/1989 |
| EP | 0500734 | 9/1992 |
| WO | WO 1986/01961 | 3/1986 |
| WO | WO 1986/06101 | 10/1986 |
| WO | WO 1987/04187 | 7/1987 |
| WO | WO 1987/07144 | 12/1987 |
| WO | WO 1988/00381 | 1/1988 |
| WO | WO 1991/07490 | 5/1991 |
| WO | WO 1991/09122 | 6/1991 |
| WO | WO 1995/13300 | 5/1995 |
| WO | WO 2000/49147 | 8/2000 |
| WO | WO 2001/023527 | 4/2001 |
| WO | WO 2001/70968 | 9/2001 |

OTHER PUBLICATIONS

"Cell Harvest Clarification Scaling Strategies" (Retrieved from the Internet <http://www.millipore.com/processdev/pd3/cellharvestscaling>, retrieved on Oct. 13, 2011).*

Keay, "Autoclavable Low Cost Serum-Free Cell Culture Media. The Growth of L Cells and BHK Cells on Peptones", Biotechnology and Engineering, XVII:745-764 (1975).

Hasegawa et al., "Proteose Peptone Enhances Production of Tissue-Type Plasminogen Activator From Human Diploid Fibroblasts", Biochemical and Biophysical Research Communications, 150(3):1230-1236 (1988).

"Membrane Protein and Carbohydrate" from "Instant notes in Biochemistry", Extract from Hames BD and Hooper NM, 2nd Edition, BIOS Scientific Publishers, pp. 124-129 (2000).

Ohlendieck, "Extraction of Membrane Proteins", Methods in Molecular Biology, 244:283-293 (1996) Protein Publication Protocols, Second Edition.

Schroder et al. (Serum- and protein-free media formulations for the Chinese hamster ovary cell line DUKXB11, Journal of Biotechnology 108 (2004) 279-292.

(Continued)

*Primary Examiner* — Suzanne M Noakes

*Assistant Examiner* — Jae W Lee

(74) *Attorney, Agent, or Firm* — Wenderoth, Lind & Ponack, L.L.P.

(57) ABSTRACT

The present invention provides a method for increasing the yield of a protein produced by cultivating eukaryotic cells and adding an ionic substance to the culture medium prior to harvest of the protein. Suitable ionic substances are the salts of the Hofmeister series, amino acids and peptone.

12 Claims, 4 Drawing Sheets

Specification includes a Sequence Listing.

(56) References Cited

OTHER PUBLICATIONS

Adamson R. (1994) Design and operation of a recombinant mammalian cell manufacturing process for rFVIII. Ann Hematol. 68 Suppl 3:S9-S14.
Fang H, et al. (2007) The protein structure and effect of factor VIII. Thromb Res: 119(1):1-13.
Fuentes-Prior P, et al., (2002) New insights into binding interfaces of coagulation factors V and VIII and their homologues lessons from high resolution crystal structures. Curr Protein Pept Sci. 3(3):313-339.
Pratt KP, et al. (1999) Structure of the C2 domain of human factor VIII at 1.5 A resolution. Nature. 402(6760):439-442.
Spiegel PC Jr, et al. (2001) Structure of a factor VIII C2 domain-immunoglobulin G4kappa Fab complex: identification of an inhibitory antibody epitope on the surface of factor VIII. Blood. 98(1):13-19.
"Chapter 6—The Plasma Membrane" in *Molecular Biology of the Cell*, 2nd Edition (Bruce Alberts, et al., Eds.; Published in New York, New York, 1989), pp. 284-285.
"Chapter 12—Protein Conformation, Dynamics, and Function" in *Biochemistry*, 3rd Edition (Lubert Stryer, Ed.); Published in USA, 1988); pp. 292-293.
"Chapter 11—The Molecular Biology of Blood Coagulation" in *Current Hematology*, vol. 2 (Virgil F. Fairbanks, Ed.); Published in USA, 1983, pp. 347-374.
"Chapter 29—Extraction of Membrane Proteins" in *Methods in Molecular Biology*, vol. 244—Protein Purification Protocols, 2nd Edition (P. Cutler, Ed.); 2003, pp. 283-293.
"Chapter 3—Protein Structure and Function" in *Molecular Cell Biology*, 4th Edition (Harvey Lodish, et al., Eds.); Published in the USA, 1999; pp. 82-85.
Product Information for Catalog No. N6658—Nutrient Mixture F12 (Ham); available at Sigma webpage, www.sigmaldrich.com (1 page) (2002) retrieved Oct. 27, 2005.
"E2—Membrane Protein and Carbohydrate" in *Biochemistry*, 3rd Edition (David Hames, et al., Eds.); Published in USA, 2005, pp. 124-129.
Technical Resources—Media Formulations—Catalog No. 11320—DMEM/F-12; available at Life Technologies webpage, http://www.lifetechnologies.com (2 pages) retrieved Jun. 18, 2013.
Technical Resources—Media Formulations—Catalog No. 21700—Ham's F-12 Nutrient Mix, available at Life Technologies webpage, http://www.lifetechnologies.com (1 page) retrieved Aug. 17, 2011.
International Preliminary Report on Patentability and Written Opinion dated Mar. 26, 2007 for PCT/GB2009/050115, which published as WO/2006/103258 on Oct. 5, 2006 (Stefan Winge is inventor and Octapharma AG is Applicant).
International Search Report dated Aug. 18, 2009 for PCT/GB2009/050115, which published as WO/2006/103258 on Oct. 5, 2006 (Stefan Winge is inventor and Octapharma AG is Applicant).
Boedeker BG. (2001) Production processes of licensed recombinant factor VIII preparations. Semin Thromb Hemost. 27(4): 385-394.
Fay PJ, Mastri M, Koszelak ME. (2001) Factor VIIIa cofactor activity shows enhanced ionic strength sensitivity in the absence of phospholipid. Biochim Biophys Acta. 1548(1): 159-168.
Larsson H, Akerud P, Nordling K, Raub-Segall E, Claesson-Welsh L, Björk I. (2001) A novel anti-angiogenic form of antithrombin with retained proteinase binding ability and heparin affinity. J Biol Chem. 276(15):11996-2002.
Kolind MP, Nørby PL, Flintegaard TV, Berchtold MW, Johnsen LB. (2010) The B-domain of Factor VIII reduces cell membrane attachment to host cells under serum free conditions. J Biotechnol. 147(3-4): 198-204.
Mounier CM, Ghomashchi F, Lindsay MR, et al. (2004) Supplementary Material for Arachidonic acid release from mammalian cells transfected with human groups IIA and X secreted phospholipase A(2) occurs predominantly during the secretory process and with the involvement of cytosolic phospholipase A(2)-alpha. Biol Chem. 279(24): 25024-25038.
Spiegel PC, Kaiser SM, Simon JA, Stoddard BL. (2004) Disruption of protein-membrane binding and identification of small-molecule inhibitors of coagulation factor VIII. Chem Biol. 11(10): 1413-1422.
Decision to Grant a European Patent pursuant to Article 97(1) EPC dated Nov. 5, 2010 for EP 06725404.5-1212, which was filed on Mar. 29, 2006 (Stefan Winge is inventor and Octapharma AG is Applicant).
Communication under Rule 71(3) EPC dated Jun. 11, 2010 for EP 06725404.5-1212, which was filed on Mar. 29, 2006 (Stefan Winge is inventor and Octapharma AG is Applicant).
Minutes of the Oral Proceedings issued Jun. 4, 2010 for EP 06725404.5-1212, which was filed on Mar. 29, 2006 (Stefan Winge is inventor and Octapharma AG is Applicant).
Brief Communication regarding Oral Proceedings issued May 7, 2010 for EP 06725404.5-1212, which was filed on Mar. 29, 2006 (Stefan Winge is inventor and Octapharma AG is Applicant).
Response to Summons for Oral Proceedings filed Apr. 20, 2010 for EP 06725404.5-1212, which was filed on Mar. 29, 2006 (Stefan Winge is inventor and Octapharma AG is Applicant).
Summons for Oral Proceedings issued Nov. 24, 2009 for EP 06725404.5-1212, which was filed on Mar. 29, 2006 (Stefan Winge is inventor and Octapharma AG is Applicant).
Brief Communication regarding Oral Proceedings issued Nov. 23, 2009 for EP 06725404.5-1212, which was filed on Mar. 29, 2006 (Stefan Winge is inventor and Octapharma AG is Applicant).
Response to Summons for Oral Proceedings filed Oct. 29, 2009 for EP 06725404.5-1212, which was filed on Mar. 29, 2006 (Stefan Winge is inventor and Octapharma AG is Applicant).
Summons for Oral Proceedings issued Sep. 16, 2009 for EP 06725404.5-1212, which was filed on Mar. 29, 2006 (Stefan Winge is inventor and Octapharma AG is Applicant).
Response filed Sep. 22, 2008 for EP 06725404.5-1212, which was filed on Mar. 29, 2006 (Stefan Winge is inventor and Octapharma AG is Applicant).
Communication pursuant to Article 94(3) EPC dated Mar. 13, 2008 for EP 06725404.5-1212, which was filed on Mar. 29, 2006 (Stefan Winge is inventor and Octapharma AG is Applicant).
Demand for International Preliminary Examination filed Jan. 27, 2007 for EP 06725404.5-1212, which was filed on Mar. 29, 2006 (Stefan Winge is inventor and Octapharma AG is Applicant).
Extended European Search Report dated Nov. 4, 2010 for EP 10181018.0-1212, which was filed on Sep. 24, 2010 (Stefan Winge is inventor and Octapharma AG is Applicant).
Bollard E, Bourgoin SG, Bernatchez C, Poubelle PE, Surette ME. (2003) Interaction of low molecular weight group IIA phospholipase A2 with apoptotic human T cells: role of heparan sulfate proteoglycans. FASEB J. 17(9): 1068-1080.
Berman, K. et al., "Isolation and Characterization of pmk-(1-3): Three p38 Homologs in *Caenorhabditis elegans*" Mol. Cell Biol. Res. Com. 4, 337-344(2001).
Chen, C. et al., "High-Efficiency Transformation of Mammalian Cells by Plasid DNA" Mol. Cell Biol. 7(8), 2745-2752 (1987).
Denys, A. et al., "Involvement of two classes of binding sites in the interactions of cyclophilin B with peripheral blood T-lymphocytes" Biochem J., 336, 689-697 (1998).
Eriksson et al., "The Manufacturing Process for B-Domain Deleted Recombinant Factor VIII" Seminars in Hematology 38, Suppl. 4, 24-31 (2001).
Fannon, M. et al., "Potentiation and Inhibition of bFGF Binding by Heparin: A Model for Regulation of Cellular Response" Biochemistry 39, 1434-1445 (2000).
Fuire and Furie, "The Molecular Basis of Blood Coagulation" Cell (1988) 53, 505-518.
Graham, F.L., "Characteristics of a Human Cell Line Transformed by DNA from Human Adenovirus Type 5" J. Gen Virol. 36(1), 59-74 (1974).
Grasser et al., "Camelysin is a Novel Surface Metalloproteinase from *Bacillus cereus*" Infection and Immunity. p. 213-228 (2004).
Herlitschka et al., High expression of a B-domain deleted factor VIII gene in a human hepatic cell line Journal of Biotechnology 61, 165-173 (1998).

(56) References Cited

OTHER PUBLICATIONS

Mounier et al., "Arachidonic Acid Release from Mammalian Cells Transfected with Human Groups IIA and X Secreted Phospholipase $A_2$ Occurs Predominantly during the Secretory Process and with the Involvement of Cytosolic Phospholipase $A_2$-$\alpha$" J. Biol. Chem. 279, No. 24, pp. 25024-25038 (2004).
Norbeck, J. et al., Proein expression during exponential growth in 0.7 M NaCl medium of *Sacchatomyces cerevisiae*FEMS Microbiology Letters 137, p. 108 (1996).
Sandberg et al., "Structural and Functional Characterization of B-Domain Deleted Recombinant Factor VIII" Seminars in Hematology 38, Suppl 4, 24-31 (2001).
Vaandrager et al., "N-terminal Myristoylation is Required for Membrane Localization of cGMP-dependent Protein Kinase Type II" J. Biol. Chem., vol. 271, No. 12, pp. 7025-7029 (1996).
Wang et al., "Coagulation factor VIII: structure and stability" International Journal of Pharmaceutics 259, 1-15 (2003).
Zuber et al., "Cysteine-Rich FGF Receptor Regulates Intracellular FGF-1 and FGF-2 Levels" J. Cell Physiology, 170:217-227 (1997).

* cited by examiner

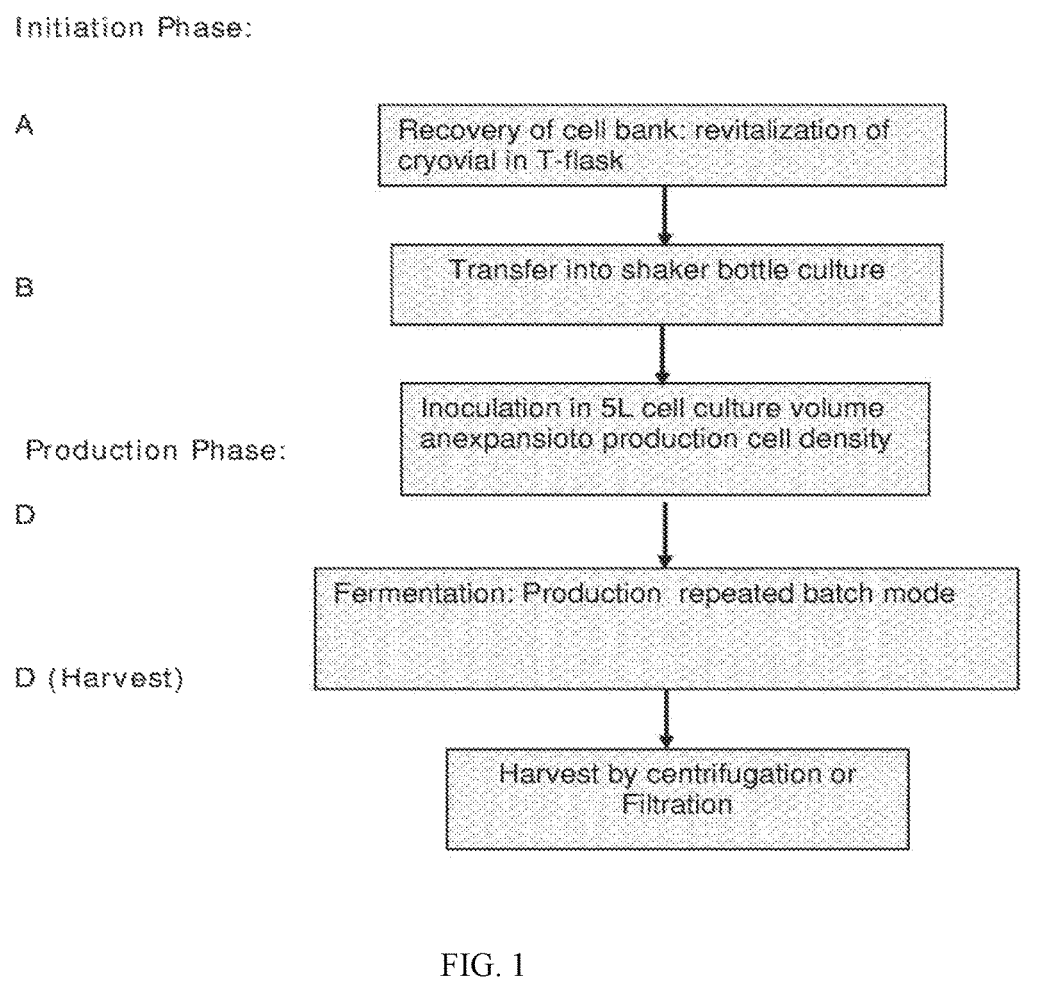

Initiation Phase:

A

B

Production Phase:

D

D (Harvest)

Recovery of cell bank: revitalization of cryovial in T-flask

Transfer into shaker bottle culture

Inoculation in 5L cell culture volume anexpansioto production cell density

Fermentation: Production repeated batch mode

Harvest by centrifugation or Filtration

FIG. 1

SEQUENCE LISTING

```
<160> NUMBER OF SEQ ID NOS: 11

<210> SEQ ID NO 1
<211> LENGTH: 6996
<212> TYPE: DNA
<213> ORGANISM: Homo sapiens
<220> FEATURE:
<221> NAME/KEY: CDS
<222> LOCATION: (1)..(6996)

<400> SEQUENCE: 1

gcc acc aga aga tac tac ctg ggt gca gtg gaa ctg tca tgg gac tat       48
Ala Thr Arg Arg Tyr Tyr Leu Gly Ala Val Glu Leu Ser Trp Asp Tyr
1               5                   10                  15

atg caa agt gat ctc ggt gag ctg cct gtg gac gca aga ttt cct cct       96
Met Gln Ser Asp Leu Gly Glu Leu Pro Val Asp Ala Arg Phe Pro Pro
            20                  25                  30

aga gtg cca aaa tct ttt cca ttc aac acc tca gtc gtg tac aaa aag      144
Arg Val Pro Lys Ser Phe Pro Phe Asn Thr Ser Val Val Tyr Lys Lys
```

```
        35                  40                  45

act ctg ttt gta gaa ttc acg gtt cac ctt ttc aac atc gct aag cca      192
Thr Leu Phe Val Glu Phe Thr Val His Leu Phe Asn Ile Ala Lys Pro
    50                  55                  60

agg cca ccc tgg atg ggt ctg cta ggt cct acc atc cag gct gag gtt      240
Arg Pro Pro Trp Met Gly Leu Leu Gly Pro Thr Ile Gln Ala Glu Val
65                  70                  75                  80

tat gat aca gtg gtc att aca ctt aag aac atg gct tcc cat cct gtc      288
Tyr Asp Thr Val Val Ile Thr Leu Lys Asn Met Ala Ser His Pro Val
                85                  90                  95

agt ctt cat gct gtt ggt gta tcc tac tgg aaa gct tct gag gga gct      336
Ser Leu His Ala Val Gly Val Ser Tyr Trp Lys Ala Ser Glu Gly Ala
            100                 105                 110

gaa tat gat gat cag acc agt caa agg gag aaa gaa gat gat aaa gtc      384
Glu Tyr Asp Asp Gln Thr Ser Gln Arg Glu Lys Glu Asp Asp Lys Val
        115                 120                 125

ttc cct ggt gga agc cat aca tat gtc tgg cag gtc ctg aaa gag aat      432
Phe Pro Gly Gly Ser His Thr Tyr Val Trp Gln Val Leu Lys Glu Asn
    130                 135                 140

ggt cca atg gcc tct gac cca ctg tgc ctt acc tac tca tat ctt tct      480
Gly Pro Met Ala Ser Asp Pro Leu Cys Leu Thr Tyr Ser Tyr Leu Ser
145                 150                 155                 160

cat gtg gac ctg gta aaa gac ttg aat tca ggc ctc att gga gcc cta      528
His Val Asp Leu Val Lys Asp Leu Asn Ser Gly Leu Ile Gly Ala Leu
                165                 170                 175

cta gta tgt aga gaa ggg agt ctg gcc aag gaa aag aca cag acc ttg      576
Leu Val Cys Arg Glu Gly Ser Leu Ala Lys Glu Lys Thr Gln Thr Leu
            180                 185                 190

cac aaa ttt ata cta ctt ttt gct gta ttt gat gaa ggg aaa agt tgg      624
His Lys Phe Ile Leu Leu Phe Ala Val Phe Asp Glu Gly Lys Ser Trp
        195                 200                 205

cac tca gaa aca aag aac tcc ttg atg cag gat agg gat gct gca tct      672
His Ser Glu Thr Lys Asn Ser Leu Met Gln Asp Arg Asp Ala Ala Ser
    210                 215                 220

gct cgg gcc tgg cct aaa atg cac aca gtc aat ggt tat gta aac agg      720
Ala Arg Ala Trp Pro Lys Met His Thr Val Asn Gly Tyr Val Asn Arg
225                 230                 235                 240

tct ctg cca ggt ctg att gga tgc cac agg aaa tca gtc tat tgg cat      768
Ser Leu Pro Gly Leu Ile Gly Cys His Arg Lys Ser Val Tyr Trp His
                245                 250                 255

gtg att gga atg ggc acc act cct gaa gtg cac tca ata ttc ctc gaa      816
Val Ile Gly Met Gly Thr Thr Pro Glu Val His Ser Ile Phe Leu Glu
            260                 265                 270

ggt cac aca ttt ctt gtg agg aac cat cgc cag gcg tcc ttg gaa atc      864
Gly His Thr Phe Leu Val Arg Asn His Arg Gln Ala Ser Leu Glu Ile
        275                 280                 285

tcg cca ata act ttc ctt act gct caa aca ctc ttg atg gac ctt gga      912
Ser Pro Ile Thr Phe Leu Thr Ala Gln Thr Leu Leu Met Asp Leu Gly
    290                 295                 300

cag ttt cta ctg ttt tgt cat atc tct tcc cac caa cat gat ggc atg      960
Gln Phe Leu Leu Phe Cys His Ile Ser Ser His Gln His Asp Gly Met
305                 310                 315                 320

gaa gct tat gtc aaa gta gac agc tgt cca gag gaa ccc caa cta cga     1008
Glu Ala Tyr Val Lys Val Asp Ser Cys Pro Glu Glu Pro Gln Leu Arg
                325                 330                 335

atg aaa aat aat gaa gaa gcg gaa gac tat gat gat gat ctt act gat     1056
Met Lys Asn Asn Glu Glu Ala Glu Asp Tyr Asp Asp Asp Leu Thr Asp
            340                 345                 350

tct gaa atg gat gtg gtc agg ttt gat gat gac aac tct cct tcc ttt     1104
```

```
Ser Glu Met Asp Val Val Arg Phe Asp Asp Asp Asn Ser Pro Ser Phe
        355                 360                 365

atc caa att cgc tca gtt gcc aag aag cat cct aaa act tgg gta cat      1152
Ile Gln Ile Arg Ser Val Ala Lys Lys His Pro Lys Thr Trp Val His
    370                 375                 380

tac att gct gct gaa gag gag gac tgg gac tat gct ccc tta gtc ctc      1200
Tyr Ile Ala Ala Glu Glu Glu Asp Trp Asp Tyr Ala Pro Leu Val Leu
385                 390                 395                 400

gcc ccc gat gac aga agt tat aaa agt caa tat ttg aac aat ggc cct      1248
Ala Pro Asp Asp Arg Ser Tyr Lys Ser Gln Tyr Leu Asn Asn Gly Pro
                405                 410                 415

cag cgg att ggt agg aag tac aaa aaa gtc cga ttt atg gca tac aca      1296
Gln Arg Ile Gly Arg Lys Tyr Lys Lys Val Arg Phe Met Ala Tyr Thr
            420                 425                 430

gat gaa acc ttt aag act cgt gaa gct att cag cat gaa tca gga atc      1344
Asp Glu Thr Phe Lys Thr Arg Glu Ala Ile Gln His Glu Ser Gly Ile
        435                 440                 445

ttg gga cct tta ctt tat ggg gaa gtt gga gac aca ctg ttg att ata      1392
Leu Gly Pro Leu Leu Tyr Gly Glu Val Gly Asp Thr Leu Leu Ile Ile
    450                 455                 460

ttt aag aat caa gca agc aga cca tat aac atc tac cct cac gga atc      1440
Phe Lys Asn Gln Ala Ser Arg Pro Tyr Asn Ile Tyr Pro His Gly Ile
465                 470                 475                 480

act gat gtc cgt cct ttg tat tca agg aga tta cca aaa ggt gta aaa      1488
Thr Asp Val Arg Pro Leu Tyr Ser Arg Arg Leu Pro Lys Gly Val Lys
                485                 490                 495

cat ttg aag gat ttt cca att ctg cca gga gaa ata ttc aaa tat aaa      1536
His Leu Lys Asp Phe Pro Ile Leu Pro Gly Glu Ile Phe Lys Tyr Lys
            500                 505                 510

tgg aca gtg act gta gaa gat ggg cca act aaa tca gat cct cgg tgc      1584
Trp Thr Val Thr Val Glu Asp Gly Pro Thr Lys Ser Asp Pro Arg Cys
        515                 520                 525

ctg acc cgc tat tac tct agt ttc gtt aat atg gag aga gat cta gct      1632
Leu Thr Arg Tyr Tyr Ser Ser Phe Val Asn Met Glu Arg Asp Leu Ala
    530                 535                 540

tca gga ctc att ggc cct ctc ctc atc tgc tac aaa gaa tct gta gat      1680
Ser Gly Leu Ile Gly Pro Leu Leu Ile Cys Tyr Lys Glu Ser Val Asp
545                 550                 555                 560

caa aga gga aac cag ata atg tca gac aag agg aat gtc atc ctg ttt      1728
Gln Arg Gly Asn Gln Ile Met Ser Asp Lys Arg Asn Val Ile Leu Phe
                565                 570                 575

tct gta ttt gat gag aac cga agc tgg tac ctc aca gag aat ata caa      1776
Ser Val Phe Asp Glu Asn Arg Ser Trp Tyr Leu Thr Glu Asn Ile Gln
            580                 585                 590

cgc ttt ctc ccc aat cca gct gga gtg cag ctt gag gat cca gag ttc      1824
Arg Phe Leu Pro Asn Pro Ala Gly Val Gln Leu Glu Asp Pro Glu Phe
        595                 600                 605

caa gcc tcc aac atc atg cac agc atc aat ggc tat gtt ttt gat agt      1872
Gln Ala Ser Asn Ile Met His Ser Ile Asn Gly Tyr Val Phe Asp Ser
    610                 615                 620

ttg cag ttg tca gtt tgt ttg cat gag gtg gca tac tgg tac att cta      1920
Leu Gln Leu Ser Val Cys Leu His Glu Val Ala Tyr Trp Tyr Ile Leu
625                 630                 635                 640

agc att gga gca cag act gac ttc ctt tct gtc ttc ttc tct gga tat      1968
Ser Ile Gly Ala Gln Thr Asp Phe Leu Ser Val Phe Phe Ser Gly Tyr
                645                 650                 655

acc ttc aaa cac aaa atg gtc tat gaa gac aca ctc acc cta ttc cca      2016
Thr Phe Lys His Lys Met Val Tyr Glu Asp Thr Leu Thr Leu Phe Pro
            660                 665                 670
```

```
ttc tca gga gaa act gtc ttc atg tcg atg gaa aac cca ggt cta tgg     2064
Phe Ser Gly Glu Thr Val Phe Met Ser Met Glu Asn Pro Gly Leu Trp
        675                 680                 685

att ctg ggg tgc cac aac tca gac ttt cgg aac aga ggc atg acc gcc     2112
Ile Leu Gly Cys His Asn Ser Asp Phe Arg Asn Arg Gly Met Thr Ala
    690                 695                 700

tta ctg aag gtt tct agt tgt gac aag aac act ggt gat tat tac gag     2160
Leu Leu Lys Val Ser Ser Cys Asp Lys Asn Thr Gly Asp Tyr Tyr Glu
705                 710                 715                 720

gac agt tat gaa gat att tca gca tac ttg ctg agt aaa aac aat gcc     2208
Asp Ser Tyr Glu Asp Ile Ser Ala Tyr Leu Leu Ser Lys Asn Asn Ala
                725                 730                 735

att gaa cca aga agc ttc tcc cag aat tca aga cac cct agc act agg     2256
Ile Glu Pro Arg Ser Phe Ser Gln Asn Ser Arg His Pro Ser Thr Arg
            740                 745                 750

caa aag caa ttt aat gcc acc aca att cca gaa aat gac ata gag aag     2304
Gln Lys Gln Phe Asn Ala Thr Thr Ile Pro Glu Asn Asp Ile Glu Lys
        755                 760                 765

act gac cct tgg ttt gca cac aga aca cct atg cct aaa ata caa aat     2352
Thr Asp Pro Trp Phe Ala His Arg Thr Pro Met Pro Lys Ile Gln Asn
    770                 775                 780

gtc tcc tct agt gat ttg ttg atg ctc ttg cga cag agt cct act cca     2400
Val Ser Ser Ser Asp Leu Leu Met Leu Leu Arg Gln Ser Pro Thr Pro
785                 790                 795                 800

cat ggg cta tcc tta tct gat ctc caa gaa gcc aaa tat gag act ttt     2448
His Gly Leu Ser Leu Ser Asp Leu Gln Glu Ala Lys Tyr Glu Thr Phe
                805                 810                 815

tct gat gat cca tca cct gga gca ata gac agt aat aac agc ctg tct     2496
Ser Asp Asp Pro Ser Pro Gly Ala Ile Asp Ser Asn Asn Ser Leu Ser
            820                 825                 830

gaa atg aca cac ttc agg cca cag ctc cat cac agt ggg gac atg gta     2544
Glu Met Thr His Phe Arg Pro Gln Leu His His Ser Gly Asp Met Val
        835                 840                 845

ttt acc cct gag tca ggc ctc caa tta aga tta aat gag aaa ctg ggg     2592
Phe Thr Pro Glu Ser Gly Leu Gln Leu Arg Leu Asn Glu Lys Leu Gly
    850                 855                 860

aca act gca gca aca gag ttg aag aaa ctt gat ttc aaa gtt tct agt     2640
Thr Thr Ala Ala Thr Glu Leu Lys Lys Leu Asp Phe Lys Val Ser Ser
865                 870                 875                 880

aca tca aat aat ctg att tca aca att cca tca gac aat ttg gca gca     2688
Thr Ser Asn Asn Leu Ile Ser Thr Ile Pro Ser Asp Asn Leu Ala Ala
                885                 890                 895

ggt act gat aat aca agt tcc tta gga ccc cca agt atg cca gtt cat     2736
Gly Thr Asp Asn Thr Ser Ser Leu Gly Pro Pro Ser Met Pro Val His
            900                 905                 910

tat gat agt caa tta gat acc act cta ttt ggc aaa aag tca tct ccc     2784
Tyr Asp Ser Gln Leu Asp Thr Thr Leu Phe Gly Lys Lys Ser Ser Pro
        915                 920                 925

ctt act gag tct ggt gga cct ctg agc ttg agt gaa gaa aat aat gat     2832
Leu Thr Glu Ser Gly Gly Pro Leu Ser Leu Ser Glu Glu Asn Asn Asp
    930                 935                 940

tca aag ttg tta gaa tca ggt tta atg aat agc caa gaa agt tca tgg     2880
Ser Lys Leu Leu Glu Ser Gly Leu Met Asn Ser Gln Glu Ser Ser Trp
945                 950                 955                 960

gga aaa aat gta tcg tca aca gag agt ggt agg tta ttt aaa ggg aaa     2928
Gly Lys Asn Val Ser Ser Thr Glu Ser Gly Arg Leu Phe Lys Gly Lys
                965                 970                 975

aga gct cat gga cct gct ttg ttg act aaa gat aat gcc tta ttc aaa     2976
Arg Ala His Gly Pro Ala Leu Leu Thr Lys Asp Asn Ala Leu Phe Lys
            980                 985                 990
```

-continued

```
gtt agc atc tct ttg tta aag aca  aac aaa act tcc aat  aat tca gca     3024
Val Ser Ile Ser Leu Leu Lys Thr  Asn Lys Thr Ser Asn  Asn Ser Ala
        995                 1000                 1005

act aat  aga aag act cac att  gat ggc cca tca tta  tta att gag      3069
Thr Asn  Arg Lys Thr His Ile  Asp Gly Pro Ser Leu  Leu Ile Glu
    1010                 1015                 1020

aat agt  cca tca gtc tgg caa  aat ata tta gaa agt  gac act gag      3114
Asn Ser  Pro Ser Val Trp Gln  Asn Ile Leu Glu Ser  Asp Thr Glu
    1025                 1030                 1035

ttt aaa  aaa gtg aca cct ttg  att cat gac aga atg  ctt atg gac      3159
Phe Lys  Lys Val Thr Pro Leu  Ile His Asp Arg Met  Leu Met Asp
    1040                 1045                 1050

aaa aat  gct aca gct ttg agg  cta aat cat atg tca  aat aaa act      3204
Lys Asn  Ala Thr Ala Leu Arg  Leu Asn His Met Ser  Asn Lys Thr
    1055                 1060                 1065

act tca  tca aaa aac atg gaa  atg gtc caa cag aaa  aaa gag ggc      3249
Thr Ser  Ser Lys Asn Met Glu  Met Val Gln Gln Lys  Lys Glu Gly
    1070                 1075                 1080

ccc att  cca cca gat gca caa  aat cca gat atg tcg  ttc ttt aag      3294
Pro Ile  Pro Pro Asp Ala Gln  Asn Pro Asp Met Ser  Phe Phe Lys
    1085                 1090                 1095

atg cta  ttc ttg cca gaa tca  gca agg tgg ata caa  agg act cat      3339
Met Leu  Phe Leu Pro Glu Ser  Ala Arg Trp Ile Gln  Arg Thr His
    1100                 1105                 1110

gga aag  aac tct ctg aac tct  ggg caa ggc ccc agt  cca aag caa      3384
Gly Lys  Asn Ser Leu Asn Ser  Gly Gln Gly Pro Ser  Pro Lys Gln
    1115                 1120                 1125

tta gta  tcc tta gga cca gaa  aaa tct gtg gaa ggt  cag aat ttc      3429
Leu Val  Ser Leu Gly Pro Glu  Lys Ser Val Glu Gly  Gln Asn Phe
    1130                 1135                 1140

ttg tct  gag aaa aac aaa gtg  gta gta gga aag ggt  gaa ttt aca      3474
Leu Ser  Glu Lys Asn Lys Val  Val Val Gly Lys Gly  Glu Phe Thr
    1145                 1150                 1155

aag gac  gta gga ctc aaa gag  atg gtt ttt cca agc  agc aga aac      3519
Lys Asp  Val Gly Leu Lys Glu  Met Val Phe Pro Ser  Ser Arg Asn
    1160                 1165                 1170

cta ttt  ctt act aac ttg gat  aat tta cat gaa aat  aat aca cac      3564
Leu Phe  Leu Thr Asn Leu Asp  Asn Leu His Glu Asn  Asn Thr His
    1175                 1180                 1185

aat caa  gaa aaa aaa att cag  gaa gaa ata gaa aag  aag gaa aca      3609
Asn Gln  Glu Lys Lys Ile Gln  Glu Glu Ile Glu Lys  Lys Glu Thr
    1190                 1195                 1200

tta atc  caa gag aat gta gtt  ttg cct cag ata cat  aca gtg act      3654
Leu Ile  Gln Glu Asn Val Val  Leu Pro Gln Ile His  Thr Val Thr
    1205                 1210                 1215

ggc act  aag aat ttc atg aag  aac ctt ttc tta ctg  agc act agg      3699
Gly Thr  Lys Asn Phe Met Lys  Asn Leu Phe Leu Leu  Ser Thr Arg
    1220                 1225                 1230

caa aat  gta gaa ggt tca tat  gag ggg gca tat gct  cca gta ctt      3744
Gln Asn  Val Glu Gly Ser Tyr  Glu Gly Ala Tyr Ala  Pro Val Leu
    1235                 1240                 1245

caa gat  ttt agg tca tta aat  gat tca aca aat aga  aca aag aaa      3789
Gln Asp  Phe Arg Ser Leu Asn  Asp Ser Thr Asn Arg  Thr Lys Lys
    1250                 1255                 1260

cac aca  gct cat ttc tca aaa  aaa ggg gag gaa gaa  aac ttg gaa      3834
His Thr  Ala His Phe Ser Lys  Lys Gly Glu Glu Glu  Asn Leu Glu
    1265                 1270                 1275

ggc ttg  gga aat caa acc aag  caa att gta gag aaa  tat gca tgc      3879
Gly Leu  Gly Asn Gln Thr Lys  Gln Ile Val Glu Lys  Tyr Ala Cys
```

```
    1280                1285                1290

acc aca  agg ata tct cct aat  aca agc cag cag aat  ttt gtc acg      3924
Thr Thr  Arg Ile Ser Pro Asn  Thr Ser Gln Gln Asn  Phe Val Thr
    1295                1300                1305

caa cgt  agt aag aga gct ttg  aaa caa ttc aga ctc  cca cta gaa      3969
Gln Arg  Ser Lys Arg Ala Leu  Lys Gln Phe Arg Leu  Pro Leu Glu
    1310                1315                1320

gaa aca  gaa ctt gaa aaa agg  ata att gtg gat gac  acc tca acc      4014
Glu Thr  Glu Leu Glu Lys Arg  Ile Ile Val Asp Asp  Thr Ser Thr
    1325                1330                1335

cag tgg  tcc aaa aac atg aaa  cat ttg acc ccg agc  acc ctc aca      4059
Gln Trp  Ser Lys Asn Met Lys  His Leu Thr Pro Ser  Thr Leu Thr
    1340                1345                1350

cag ata  gac tac aat gag aag  gag aaa ggg gcc att  act cag tct      4104
Gln Ile  Asp Tyr Asn Glu Lys  Glu Lys Gly Ala Ile  Thr Gln Ser
    1355                1360                1365

ccc tta  tca gat tgc ctt acg  agg agt cat agc atc  cct caa gca      4149
Pro Leu  Ser Asp Cys Leu Thr  Arg Ser His Ser Ile  Pro Gln Ala
    1370                1375                1380

aat aga  tct cca tta ccc att  gca aag gta tca tca  ttt cca tct      4194
Asn Arg  Ser Pro Leu Pro Ile  Ala Lys Val Ser Ser  Phe Pro Ser
    1385                1390                1395

att aga  cct ata tat ctg acc  agg gtc cta ttc caa  gac aac tct      4239
Ile Arg  Pro Ile Tyr Leu Thr  Arg Val Leu Phe Gln  Asp Asn Ser
    1400                1405                1410

tct cat  ctt cca gca gca tct  tat aga aag aaa gat  tct ggg gtc      4284
Ser His  Leu Pro Ala Ala Ser  Tyr Arg Lys Lys Asp  Ser Gly Val
    1415                1420                1425

caa gaa  agc agt cat ttc tta  caa gga gcc aaa aaa  aat aac ctt      4329
Gln Glu  Ser Ser His Phe Leu  Gln Gly Ala Lys Lys  Asn Asn Leu
    1430                1435                1440

tct tta  gcc att cta acc ttg  gag atg act ggt gat  caa aga gag      4374
Ser Leu  Ala Ile Leu Thr Leu  Glu Met Thr Gly Asp  Gln Arg Glu
    1445                1450                1455

gtt ggc  tcc ctg ggg aca agt  gcc aca aat tca gtc  aca tac aag      4419
Val Gly  Ser Leu Gly Thr Ser  Ala Thr Asn Ser Val  Thr Tyr Lys
    1460                1465                1470

aaa gtt  gag aac act gtt ctc  ccg aaa cca gac ttg  ccc aaa aca      4464
Lys Val  Glu Asn Thr Val Leu  Pro Lys Pro Asp Leu  Pro Lys Thr
    1475                1480                1485

tct ggc  aaa gtt gaa ttg ctt  cca aaa gtt cac att  tat cag aag      4509
Ser Gly  Lys Val Glu Leu Leu  Pro Lys Val His Ile  Tyr Gln Lys
    1490                1495                1500

gac cta  ttc cct acg gaa act  agc aat ggg tct cct  ggc cat ctg      4554
Asp Leu  Phe Pro Thr Glu Thr  Ser Asn Gly Ser Pro  Gly His Leu
    1505                1510                1515

gat ctc  gtg gaa ggg agc ctt  ctt cag gga aca gag  gga gcg att      4599
Asp Leu  Val Glu Gly Ser Leu  Leu Gln Gly Thr Glu  Gly Ala Ile
    1520                1525                1530

aag tgg  aat gaa gca aac aga  cct gga aaa gtt ccc  ttt ctg aga      4644
Lys Trp  Asn Glu Ala Asn Arg  Pro Gly Lys Val Pro  Phe Leu Arg
    1535                1540                1545

gta gca  aca gaa agc tct gca  aag act ccc tcc aag  cta ttg gat      4689
Val Ala  Thr Glu Ser Ser Ala  Lys Thr Pro Ser Lys  Leu Leu Asp
    1550                1555                1560

cct ctt  gct tgg gat aac cac  tat ggt act cag ata  cca aaa gaa      4734
Pro Leu  Ala Trp Asp Asn His  Tyr Gly Thr Gln Ile  Pro Lys Glu
    1565                1570                1575

gag tgg  aaa tcc caa gag aag  tca cca gaa aaa aca  gct ttt aag      4779
```

```
Glu Trp  Lys Ser Gln Glu Lys  Ser Pro Glu Lys Thr  Ala Phe Lys
    1580                 1585                 1590

aaa aag  gat acc att ttg tcc  ctg aac gct tgt gaa  agc aat cat      4824
Lys Lys  Asp Thr Ile Leu Ser  Leu Asn Ala Cys Glu  Ser Asn His
    1595                 1600                 1605

gca ata  gca gca ata aat gag  gga caa aat aag ccc  gaa ata gaa      4869
Ala Ile  Ala Ala Ile Asn Glu  Gly Gln Asn Lys Pro  Glu Ile Glu
    1610                 1615                 1620

gtc acc  tgg gca aag caa ggt  agg act gaa agg ctg  tgc tct caa      4914
Val Thr  Trp Ala Lys Gln Gly  Arg Thr Glu Arg Leu  Cys Ser Gln
    1625                 1630                 1635

aac cca  cca gtc ttg aaa cgc  cat caa cgg gaa ata  act cgt act      4959
Asn Pro  Pro Val Leu Lys Arg  His Gln Arg Glu Ile  Thr Arg Thr
    1640                 1645                 1650

act ctt  cag tca gat caa gag  gaa att gac tat gat  gat acc ata      5004
Thr Leu  Gln Ser Asp Gln Glu  Glu Ile Asp Tyr Asp  Asp Thr Ile
    1655                 1660                 1665

tca gtt  gaa atg aag aag gaa  gat ttt gac att tat  gat gag gat      5049
Ser Val  Glu Met Lys Lys Glu  Asp Phe Asp Ile Tyr  Asp Glu Asp
    1670                 1675                 1680

gaa aat  cag agc ccc cgc agc  ttt caa aag aaa aca  cga cac tat      5094
Glu Asn  Gln Ser Pro Arg Ser  Phe Gln Lys Lys Thr  Arg His Tyr
    1685                 1690                 1695

ttt att  gct gca gtg gag agg  ctc tgg gat tat ggg  atg agt agc      5139
Phe Ile  Ala Ala Val Glu Arg  Leu Trp Asp Tyr Gly  Met Ser Ser
    1700                 1705                 1710

tcc cca  cat gtt cta aga aac  agg gct cag agt ggc  agt gtc cct      5184
Ser Pro  His Val Leu Arg Asn  Arg Ala Gln Ser Gly  Ser Val Pro
    1715                 1720                 1725

cag ttc  aag aaa gtt gtt ttc  cag gaa ttt act gat  ggc tcc ttt      5229
Gln Phe  Lys Lys Val Val Phe  Gln Glu Phe Thr Asp  Gly Ser Phe
    1730                 1735                 1740

act cag  ccc tta tac cgt gga  gaa cta aat gaa cat  ttg gga ctc      5274
Thr Gln  Pro Leu Tyr Arg Gly  Glu Leu Asn Glu His  Leu Gly Leu
    1745                 1750                 1755

ctg ggg  cca tat ata aga gca  gaa gtt gaa gat aat  atc atg gta      5319
Leu Gly  Pro Tyr Ile Arg Ala  Glu Val Glu Asp Asn  Ile Met Val
    1760                 1765                 1770

act ttc  aga aat cag gcc tct  cgt ccc tat tcc ttc  tat tct agc      5364
Thr Phe  Arg Asn Gln Ala Ser  Arg Pro Tyr Ser Phe  Tyr Ser Ser
    1775                 1780                 1785

ctt att  tct tat gag gaa gat  cag agg caa gga gca  gaa cct aga      5409
Leu Ile  Ser Tyr Glu Glu Asp  Gln Arg Gln Gly Ala  Glu Pro Arg
    1790                 1795                 1800

aaa aac  ttt gtc aag cct aat  gaa acc aaa act tac  ttt tgg aaa      5454
Lys Asn  Phe Val Lys Pro Asn  Glu Thr Lys Thr Tyr  Phe Trp Lys
    1805                 1810                 1815

gtg caa  cat cat atg gca ccc  act aaa gat gag ttt  gac tgc aaa      5499
Val Gln  His His Met Ala Pro  Thr Lys Asp Glu Phe  Asp Cys Lys
    1820                 1825                 1830

gcc tgg  gct tat ttc tct gat  gtt gac ctg gaa aaa  gat gtg cac      5544
Ala Trp  Ala Tyr Phe Ser Asp  Val Asp Leu Glu Lys  Asp Val His
    1835                 1840                 1845

tca ggc  ctg att gga ccc ctt  ctg gtc tgc cac act  aac aca ctg      5589
Ser Gly  Leu Ile Gly Pro Leu  Leu Val Cys His Thr  Asn Thr Leu
    1850                 1855                 1860

aac cct  gct cat ggg aga caa  gtg aca gta cag gaa  ttt gct ctg      5634
Asn Pro  Ala His Gly Arg Gln  Val Thr Val Gln Glu  Phe Ala Leu
    1865                 1870                 1875
```

-continued

```
ttt ttc  acc atc ttt gat gag  acc aaa agc tgg tac  ttc act gaa      5679
Phe Phe  Thr Ile Phe Asp Glu  Thr Lys Ser Trp Tyr  Phe Thr Glu
    1880                 1885                 1890

aat atg  gaa aga aac tgc agg  gct ccc tgc aat atc  cag atg gaa      5724
Asn Met  Glu Arg Asn Cys Arg  Ala Pro Cys Asn Ile  Gln Met Glu
    1895                 1900                 1905

gat ccc  act ttt aaa gag aat  tat cgc ttc cat gca  atc aat ggc      5769
Asp Pro  Thr Phe Lys Glu Asn  Tyr Arg Phe His Ala  Ile Asn Gly
    1910                 1915                 1920

tac ata  atg gat aca cta cct  ggc tta gta atg gct  cag gat caa      5814
Tyr Ile  Met Asp Thr Leu Pro  Gly Leu Val Met Ala  Gln Asp Gln
    1925                 1930                 1935

agg att  cga tgg tat ctg ctc  agc atg ggc agc aat  gaa aac atc      5859
Arg Ile  Arg Trp Tyr Leu Leu  Ser Met Gly Ser Asn  Glu Asn Ile
    1940                 1945                 1950

cat tct  att cat ttc agt gga  cat gtg ttc act gta  cga aaa aaa      5904
His Ser  Ile His Phe Ser Gly  His Val Phe Thr Val  Arg Lys Lys
    1955                 1960                 1965

gag gag  tat aaa atg gca ctg  tac aat ctc tat cca  ggt gtt ttt      5949
Glu Glu  Tyr Lys Met Ala Leu  Tyr Asn Leu Tyr Pro  Gly Val Phe
    1970                 1975                 1980

gag aca  gtg gaa atg tta cca  tcc aaa gct gga att  tgg cgg gtg      5994
Glu Thr  Val Glu Met Leu Pro  Ser Lys Ala Gly Ile  Trp Arg Val
    1985                 1990                 1995

gaa tgc  ctt att ggc gag cat  cta cat gct ggg atg  agc aca ctt      6039
Glu Cys  Leu Ile Gly Glu His  Leu His Ala Gly Met  Ser Thr Leu
    2000                 2005                 2010

ttt ctg  gtg tac agc aat aag  tgt cag act ccc ctg  gga atg gct      6084
Phe Leu  Val Tyr Ser Asn Lys  Cys Gln Thr Pro Leu  Gly Met Ala
    2015                 2020                 2025

tct gga  cac att aga gat ttt  cag att aca gct tca  gga caa tat      6129
Ser Gly  His Ile Arg Asp Phe  Gln Ile Thr Ala Ser  Gly Gln Tyr
    2030                 2035                 2040

gga cag  tgg gcc cca aag ctg  gcc aga ctt cat tat  tcc gga tca      6174
Gly Gln  Trp Ala Pro Lys Leu  Ala Arg Leu His Tyr  Ser Gly Ser
    2045                 2050                 2055

atc aat  gcc tgg agc acc aag  gag ccc ttt tct tgg  atc aag gtg      6219
Ile Asn  Ala Trp Ser Thr Lys  Glu Pro Phe Ser Trp  Ile Lys Val
    2060                 2065                 2070

gat ctg  ttg gca cca atg att  att cac ggc atc aag  acc cag ggt      6264
Asp Leu  Leu Ala Pro Met Ile  Ile His Gly Ile Lys  Thr Gln Gly
    2075                 2080                 2085

gcc cgt  cag aag ttc tcc agc  ctc tac atc tct cag  ttt atc atc      6309
Ala Arg  Gln Lys Phe Ser Ser  Leu Tyr Ile Ser Gln  Phe Ile Ile
    2090                 2095                 2100

atg tat  agt ctt gat ggg aag  aag tgg cag act tat  cga gga aat      6354
Met Tyr  Ser Leu Asp Gly Lys  Lys Trp Gln Thr Tyr  Arg Gly Asn
    2105                 2110                 2115

tcc act  gga acc tta atg gtc  ttc ttt ggc aat gtg  gat tca tct      6399
Ser Thr  Gly Thr Leu Met Val  Phe Phe Gly Asn Val  Asp Ser Ser
    2120                 2125                 2130

ggg ata  aaa cac aat att ttt  aac cct cca att att  gct cga tac      6444
Gly Ile  Lys His Asn Ile Phe  Asn Pro Pro Ile Ile  Ala Arg Tyr
    2135                 2140                 2145

atc cgt  ttg cac cca act cat  tat agc att cgc agc  act ctt cgc      6489
Ile Arg  Leu His Pro Thr His  Tyr Ser Ile Arg Ser  Thr Leu Arg
    2150                 2155                 2160

atg gag  ttg atg ggc tgt gat  tta aat agt tgc agc  atg cca ttg      6534
Met Glu  Leu Met Gly Cys Asp  Leu Asn Ser Cys Ser  Met Pro Leu
    2165                 2170                 2175
```

```
gga atg  gag agt aaa gca ata  tca gat gca cag att  act gct tca      6579
Gly Met  Glu Ser Lys Ala Ile  Ser Asp Ala Gln Ile  Thr Ala Ser
    2180                 2185                 2190

tcc tac  ttt acc aat atg ttt  gcc acc tgg tct cct  tca aaa gct      6624
Ser Tyr  Phe Thr Asn Met Phe  Ala Thr Trp Ser Pro  Ser Lys Ala
    2195                 2200                 2205

cga ctt  cac ctc caa ggg agg  agt aat gcc tgg aga  cct cag gtg      6669
Arg Leu  His Leu Gln Gly Arg  Ser Asn Ala Trp Arg  Pro Gln Val
    2210                 2215                 2220

aat aat  cca aaa gag tgg ctg  caa gtg gac ttc cag  aag aca atg      6714
Asn Asn  Pro Lys Glu Trp Leu  Gln Val Asp Phe Gln  Lys Thr Met
    2225                 2230                 2235

aaa gtc  aca gga gta act act  cag gga gta aaa tct  ctg ctt acc      6759
Lys Val  Thr Gly Val Thr Thr  Gln Gly Val Lys Ser  Leu Leu Thr
    2240                 2245                 2250

agc atg  tat gtg aag gag ttc  ctc atc tcc agc agt  caa gat ggc      6804
Ser Met  Tyr Val Lys Glu Phe  Leu Ile Ser Ser Ser  Gln Asp Gly
    2255                 2260                 2265

cat cag  tgg act ctc ttt ttt  cag aat ggc aaa gta  aag gtt ttt      6849
His Gln  Trp Thr Leu Phe Phe  Gln Asn Gly Lys Val  Lys Val Phe
    2270                 2275                 2280

cag gga  aat caa gac tcc ttc  aca cct gtg gtg aac  tct cta gac      6894
Gln Gly  Asn Gln Asp Ser Phe  Thr Pro Val Val Asn  Ser Leu Asp
    2285                 2290                 2295

cca ccg  tta ctg act cgc tac  ctt cga att cac ccc  cag agt tgg      6939
Pro Pro  Leu Leu Thr Arg Tyr  Leu Arg Ile His Pro  Gln Ser Trp
    2300                 2305                 2310

gtg cac  cag att gcc ctg agg  atg gag gtt ctg ggc  tgc gag gca      6984
Val His  Gln Ile Ala Leu Arg  Met Glu Val Leu Gly  Cys Glu Ala
    2315                 2320                 2325

cag gac  ctc tac                                                    6996
Gln Asp  Leu Tyr
    2330


<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140
```

```
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

-continued

```
Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
```

-continued

```
            980                 985                 990

Val Ser Ile Ser Leu Leu Lys Thr  Asn Lys Thr Ser Asn  Asn Ser Ala
        995                 1000                 1005

Thr Asn  Arg Lys Thr His Ile  Asp Gly Pro Ser Leu  Leu Ile Glu
    1010                 1015                 1020

Asn Ser  Pro Ser Val Trp Gln  Asn Ile Leu Glu Ser  Asp Thr Glu
    1025                 1030                 1035

Phe Lys  Lys Val Thr Pro Leu  Ile His Asp Arg Met  Leu Met Asp
    1040                 1045                 1050

Lys Asn  Ala Thr Ala Leu Arg  Leu Asn His Met Ser  Asn Lys Thr
    1055                 1060                 1065

Thr Ser  Ser Lys Asn Met Glu  Met Val Gln Gln Lys  Lys Glu Gly
    1070                 1075                 1080

Pro Ile  Pro Pro Asp Ala Gln  Asn Pro Asp Met Ser  Phe Phe Lys
    1085                 1090                 1095

Met Leu  Phe Leu Pro Glu Ser  Ala Arg Trp Ile Gln  Arg Thr His
    1100                 1105                 1110

Gly Lys  Asn Ser Leu Asn Ser  Gly Gln Gly Pro Ser  Pro Lys Gln
    1115                 1120                 1125

Leu Val  Ser Leu Gly Pro Glu  Lys Ser Val Glu Gly  Gln Asn Phe
    1130                 1135                 1140

Leu Ser  Glu Lys Asn Lys Val  Val Val Gly Lys Gly  Glu Phe Thr
    1145                 1150                 1155

Lys Asp  Val Gly Leu Lys Glu  Met Val Phe Pro Ser  Ser Arg Asn
    1160                 1165                 1170

Leu Phe  Leu Thr Asn Leu Asp  Asn Leu His Glu Asn  Asn Thr His
    1175                 1180                 1185

Asn Gln  Glu Lys Lys Ile Gln  Glu Glu Ile Glu Lys  Lys Glu Thr
    1190                 1195                 1200

Leu Ile  Gln Glu Asn Val Val  Leu Pro Gln Ile His  Thr Val Thr
    1205                 1210                 1215

Gly Thr  Lys Asn Phe Met Lys  Asn Leu Phe Leu Leu  Ser Thr Arg
    1220                 1225                 1230

Gln Asn  Val Glu Gly Ser Tyr  Glu Gly Ala Tyr Ala  Pro Val Leu
    1235                 1240                 1245

Gln Asp  Phe Arg Ser Leu Asn  Asp Ser Thr Asn Arg  Thr Lys Lys
    1250                 1255                 1260

His Thr  Ala His Phe Ser Lys  Lys Gly Glu Glu Glu  Asn Leu Glu
    1265                 1270                 1275

Gly Leu  Gly Asn Gln Thr Lys  Gln Ile Val Glu Lys  Tyr Ala Cys
    1280                 1285                 1290

Thr Thr  Arg Ile Ser Pro Asn  Thr Ser Gln Gln Asn  Phe Val Thr
    1295                 1300                 1305

Gln Arg  Ser Lys Arg Ala Leu  Lys Gln Phe Arg Leu  Pro Leu Glu
    1310                 1315                 1320

Glu Thr  Glu Leu Glu Lys Arg  Ile Ile Val Asp Asp  Thr Ser Thr
    1325                 1330                 1335

Gln Trp  Ser Lys Asn Met Lys  His Leu Thr Pro Ser  Thr Leu Thr
    1340                 1345                 1350

Gln Ile  Asp Tyr Asn Glu Lys  Glu Lys Gly Ala Ile  Thr Gln Ser
    1355                 1360                 1365

Pro Leu  Ser Asp Cys Leu Thr  Arg Ser His Ser Ile  Pro Gln Ala
    1370                 1375                 1380
```

```
Asn Arg  Ser Pro Leu Pro Ile  Ala Lys Val Ser Ser  Phe Pro Ser
    1385                 1390                 1395

Ile Arg  Pro Ile Tyr Leu Thr  Arg Val Leu Phe Gln  Asp Asn Ser
    1400                 1405                 1410

Ser His  Leu Pro Ala Ala Ser  Tyr Arg Lys Lys Asp  Ser Gly Val
    1415                 1420                 1425

Gln Glu  Ser Ser His Phe Leu  Gln Gly Ala Lys Lys  Asn Asn Leu
    1430                 1435                 1440

Ser Leu  Ala Ile Leu Thr Leu  Glu Met Thr Gly Asp  Gln Arg Glu
    1445                 1450                 1455

Val Gly  Ser Leu Gly Thr Ser  Ala Thr Asn Ser Val  Thr Tyr Lys
    1460                 1465                 1470

Lys Val  Glu Asn Thr Val Leu  Pro Lys Pro Asp Leu  Pro Lys Thr
    1475                 1480                 1485

Ser Gly  Lys Val Glu Leu Leu  Pro Lys Val His Ile  Tyr Gln Lys
    1490                 1495                 1500

Asp Leu  Phe Pro Thr Glu Thr  Ser Asn Gly Ser Pro  Gly His Leu
    1505                 1510                 1515

Asp Leu  Val Glu Gly Ser Leu  Leu Gln Gly Thr Glu  Gly Ala Ile
    1520                 1525                 1530

Lys Trp  Asn Glu Ala Asn Arg  Pro Gly Lys Val Pro  Phe Leu Arg
    1535                 1540                 1545

Val Ala  Thr Glu Ser Ser Ala  Lys Thr Pro Ser Lys  Leu Leu Asp
    1550                 1555                 1560

Pro Leu  Ala Trp Asp Asn His  Tyr Gly Thr Gln Ile  Pro Lys Glu
    1565                 1570                 1575

Glu Trp  Lys Ser Gln Glu Lys  Ser Pro Glu Lys Thr  Ala Phe Lys
    1580                 1585                 1590

Lys Lys  Asp Thr Ile Leu Ser  Leu Asn Ala Cys Glu  Ser Asn His
    1595                 1600                 1605

Ala Ile  Ala Ala Ile Asn Glu  Gly Gln Asn Lys Pro  Glu Ile Glu
    1610                 1615                 1620

Val Thr  Trp Ala Lys Gln Gly  Arg Thr Glu Arg Leu  Cys Ser Gln
    1625                 1630                 1635

Asn Pro  Pro Val Leu Lys Arg  His Gln Arg Glu Ile  Thr Arg Thr
    1640                 1645                 1650

Thr Leu  Gln Ser Asp Gln Glu  Glu Ile Asp Tyr Asp  Asp Thr Ile
    1655                 1660                 1665

Ser Val  Glu Met Lys Lys Glu  Asp Phe Asp Ile Tyr  Asp Glu Asp
    1670                 1675                 1680

Glu Asn  Gln Ser Pro Arg Ser  Phe Gln Lys Lys Thr  Arg His Tyr
    1685                 1690                 1695

Phe Ile  Ala Ala Val Glu Arg  Leu Trp Asp Tyr Gly  Met Ser Ser
    1700                 1705                 1710

Ser Pro  His Val Leu Arg Asn  Arg Ala Gln Ser Gly  Ser Val Pro
    1715                 1720                 1725

Gln Phe  Lys Lys Val Val Phe  Gln Glu Phe Thr Asp  Gly Ser Phe
    1730                 1735                 1740

Thr Gln  Pro Leu Tyr Arg Gly  Glu Leu Asn Glu His  Leu Gly Leu
    1745                 1750                 1755

Leu Gly  Pro Tyr Ile Arg Ala  Glu Val Glu Asp Asn  Ile Met Val
    1760                 1765                 1770
```

```
Thr Phe  Arg Asn Gln Ala Ser  Arg Pro Tyr Ser Phe  Tyr Ser Ser
    1775                 1780                 1785

Leu Ile  Ser Tyr Glu Glu Asp  Gln Arg Gln Gly Ala  Glu Pro Arg
    1790                 1795                 1800

Lys Asn  Phe Val Lys Pro Asn  Glu Thr Lys Thr Tyr  Phe Trp Lys
    1805                 1810                 1815

Val Gln  His His Met Ala Pro  Thr Lys Asp Glu Phe  Asp Cys Lys
    1820                 1825                 1830

Ala Trp  Ala Tyr Phe Ser Asp  Val Asp Leu Glu Lys  Asp Val His
    1835                 1840                 1845

Ser Gly  Leu Ile Gly Pro Leu  Leu Val Cys His Thr  Asn Thr Leu
    1850                 1855                 1860

Asn Pro  Ala His Gly Arg Gln  Val Thr Val Gln Glu  Phe Ala Leu
    1865                 1870                 1875

Phe Phe  Thr Ile Phe Asp Glu  Thr Lys Ser Trp Tyr  Phe Thr Glu
    1880                 1885                 1890

Asn Met  Glu Arg Asn Cys Arg  Ala Pro Cys Asn Ile  Gln Met Glu
    1895                 1900                 1905

Asp Pro  Thr Phe Lys Glu Asn  Tyr Arg Phe His Ala  Ile Asn Gly
    1910                 1915                 1920

Tyr Ile  Met Asp Thr Leu Pro  Gly Leu Val Met Ala  Gln Asp Gln
    1925                 1930                 1935

Arg Ile  Arg Trp Tyr Leu Leu  Ser Met Gly Ser Asn  Glu Asn Ile
    1940                 1945                 1950

His Ser  Ile His Phe Ser Gly  His Val Phe Thr Val  Arg Lys Lys
    1955                 1960                 1965

Glu Glu  Tyr Lys Met Ala Leu  Tyr Asn Leu Tyr Pro  Gly Val Phe
    1970                 1975                 1980

Glu Thr  Val Glu Met Leu Pro  Ser Lys Ala Gly Ile  Trp Arg Val
    1985                 1990                 1995

Glu Cys  Leu Ile Gly Glu His  Leu His Ala Gly Met  Ser Thr Leu
    2000                 2005                 2010

Phe Leu  Val Tyr Ser Asn Lys  Cys Gln Thr Pro Leu  Gly Met Ala
    2015                 2020                 2025

Ser Gly  His Ile Arg Asp Phe  Gln Ile Thr Ala Ser  Gly Gln Tyr
    2030                 2035                 2040

Gly Gln  Trp Ala Pro Lys Leu  Ala Arg Leu His Tyr  Ser Gly Ser
    2045                 2050                 2055

Ile Asn  Ala Trp Ser Thr Lys  Glu Pro Phe Ser Trp  Ile Lys Val
    2060                 2065                 2070

Asp Leu  Leu Ala Pro Met Ile  Ile His Gly Ile Lys  Thr Gln Gly
    2075                 2080                 2085

Ala Arg  Gln Lys Phe Ser Ser  Leu Tyr Ile Ser Gln  Phe Ile Ile
    2090                 2095                 2100

Met Tyr  Ser Leu Asp Gly Lys  Lys Trp Gln Thr Tyr  Arg Gly Asn
    2105                 2110                 2115

Ser Thr  Gly Thr Leu Met Val  Phe Phe Gly Asn Val  Asp Ser Ser
    2120                 2125                 2130

Gly Ile  Lys His Asn Ile Phe  Asn Pro Pro Ile Ile  Ala Arg Tyr
    2135                 2140                 2145

Ile Arg  Leu His Pro Thr His  Tyr Ser Ile Arg Ser  Thr Leu Arg
    2150                 2155                 2160

Met Glu  Leu Met Gly Cys Asp  Leu Asn Ser Cys Ser  Met Pro Leu
```

```
    2165                2170                2175

Gly Met  Glu Ser Lys Ala Ile  Ser Asp Ala Gln Ile  Thr Ala Ser
    2180                2185                2190

Ser Tyr  Phe Thr Asn Met Phe  Ala Thr Trp Ser Pro  Ser Lys Ala
    2195                2200                2205

Arg Leu  His Leu Gln Gly Arg  Ser Asn Ala Trp Arg  Pro Gln Val
    2210                2215                2220

Asn Asn  Pro Lys Glu Trp Leu  Gln Val Asp Phe Gln  Lys Thr Met
    2225                2230                2235

Lys Val  Thr Gly Val Thr Thr  Gln Gly Val Lys Ser  Leu Leu Thr
    2240                2245                2250

Ser Met  Tyr Val Lys Glu Phe  Leu Ile Ser Ser Ser  Gln Asp Gly
    2255                2260                2265

His Gln  Trp Thr Leu Phe Phe  Gln Asn Gly Lys Val  Lys Val Phe
    2270                2275                2280

Gln Gly  Asn Gln Asp Ser Phe  Thr Pro Val Val Asn  Ser Leu Asp
    2285                2290                2295

Pro Pro  Leu Leu Thr Arg Tyr  Leu Arg Ile His Pro  Gln Ser Trp
    2300                2305                2310

Val His  Gln Ile Ala Leu Arg  Met Glu Val Leu Gly  Cys Glu Ala
    2315                2320                2325

Gln Asp  Leu Tyr
    2330


<210> SEQ ID NO 3
<211> LENGTH: 10698
<212> TYPE: DNA
<213> ORGANISM: Artificial Sequence
<220> FEATURE:
<223> OTHER INFORMATION: Description of Artificial Sequence:  pTGF8-3
<220> FEATURE:
<221> NAME/KEY: CDS
<222> LOCATION: (676)..(5052)
<220> FEATURE:
<221> NAME/KEY: mat_peptide
<222> LOCATION: (733)..(5052)

<400> SEQUENCE: 3

cgcgttgaca ttgattattg actagttatt aatagtaatc aattacgggg tcattagttc     60

atagcccata tatggagttc cgcgttacat aacttacggt aaatggcccg cctggctgac    120

cgcccaacga cccccgccca ttgacgtcaa taatgacgta tgttcccata gtaacgccaa    180

tagggacttt ccattgacgt caatgggtgg agtatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360

acgtattagt catcgctatt accatggtga tgcggttttg gcagtacatc aatgggcgtg    420

gatagcggtt tgactcacgg ggatttccaa gtctccaccc cattgacgtc aatgggagtt    480

tgttttggca ccaaaatcaa cgggactttc caaaatgtcg taacaactcc gccccattga    540

cgcaaatggg cggtaggcgt gtacggtggg aggtctatat aagcagagct ctctggctaa    600

ctagagaacc cactgcttac tggcttatcg aaattaatac gactcactat agggagaccc    660

aagcttgacc tcgag atg caa ata gag ctc tcc acc tgc ttc ttt ctg tgc     711
                 Met Gln Ile Glu Leu Ser Thr Cys Phe Phe Leu Cys
                                 -15                 -10

ctt ttg cga ttc tgc ttt agt gcc acc aga aga tac tac ctg ggt gca      759
Leu Leu Arg Phe Cys Phe Ser Ala Thr Arg Arg Tyr Tyr Leu Gly Ala
```

```
        -5              -1  1               5

gtg gaa ctg tca tgg gac tat atg caa agt gat ctc ggt gag ctg cct      807
Val Glu Leu Ser Trp Asp Tyr Met Gln Ser Asp Leu Gly Glu Leu Pro
10                  15                  20                  25

gtg gac gca aga ttt cct cct aga gtg cca aaa tct ttt cca ttc aac      855
Val Asp Ala Arg Phe Pro Pro Arg Val Pro Lys Ser Phe Pro Phe Asn
                30                  35                  40

acc tca gtc gtg tac aaa aag act ctg ttt gta gaa ttc acg gat cac      903
Thr Ser Val Val Tyr Lys Lys Thr Leu Phe Val Glu Phe Thr Asp His
            45                  50                  55

ctt ttc aac atc gct aag cca agg cca ccc tgg atg ggt ctg cta ggt      951
Leu Phe Asn Ile Ala Lys Pro Arg Pro Pro Trp Met Gly Leu Leu Gly
        60                  65                  70

cct acc atc cag gct gag gtt tat gat aca gtg gtc att aca ctt aag      999
Pro Thr Ile Gln Ala Glu Val Tyr Asp Thr Val Val Ile Thr Leu Lys
    75                  80                  85

aac atg gct tcc cat cct gtc agt ctt cat gct gtt ggt gta tcc tac     1047
Asn Met Ala Ser His Pro Val Ser Leu His Ala Val Gly Val Ser Tyr
90                  95                  100                 105

tgg aaa gct tct gag gga gct gaa tat gat gat cag acc agt caa agg     1095
Trp Lys Ala Ser Glu Gly Ala Glu Tyr Asp Asp Gln Thr Ser Gln Arg
                110                 115                 120

gag aaa gaa gat gat aaa gtc ttc cct ggt gga agc cat aca tat gtc     1143
Glu Lys Glu Asp Asp Lys Val Phe Pro Gly Gly Ser His Thr Tyr Val
            125                 130                 135

tgg cag gtc ctg aaa gag aat ggt cca atg gcc tct gac cca ctg tgc     1191
Trp Gln Val Leu Lys Glu Asn Gly Pro Met Ala Ser Asp Pro Leu Cys
        140                 145                 150

ctt acc tac tca tat ctt tct cat gcg gac ctg gta aaa gac ttg aat     1239
Leu Thr Tyr Ser Tyr Leu Ser His Ala Asp Leu Val Lys Asp Leu Asn
    155                 160                 165

tca ggc ctc att gga gcc cta cta gta tgt aga gaa ggg agt ctg gcc     1287
Ser Gly Leu Ile Gly Ala Leu Leu Val Cys Arg Glu Gly Ser Leu Ala
170                 175                 180                 185

aag gaa aag aca cag acc ttg cac aaa ttt ata cta ctt ttt gct gta     1335
Lys Glu Lys Thr Gln Thr Leu His Lys Phe Ile Leu Leu Phe Ala Val
                190                 195                 200

ttt gat gaa ggg aaa agt tgg cac tca gaa aca aag aac tcc ttg atg     1383
Phe Asp Glu Gly Lys Ser Trp His Ser Glu Thr Lys Asn Ser Leu Met
            205                 210                 215

cag gat agg gat gct gca tct gct cgg gcc tgg cct aaa atg cac aca     1431
Gln Asp Arg Asp Ala Ala Ser Ala Arg Ala Trp Pro Lys Met His Thr
        220                 225                 230

gtc aat ggt tat gta aac agg tct ctg cca ggt ctg att gga tgc cac     1479
Val Asn Gly Tyr Val Asn Arg Ser Leu Pro Gly Leu Ile Gly Cys His
    235                 240                 245

agg aaa tca gtc tat tgg cat gtg att gga atg ggc acc act cct gaa     1527
Arg Lys Ser Val Tyr Trp His Val Ile Gly Met Gly Thr Thr Pro Glu
250                 255                 260                 265

gtg cac tca ata ttc ctc gaa ggt cac aca ttt ctt gtg agg aac cat     1575
Val His Ser Ile Phe Leu Glu Gly His Thr Phe Leu Val Arg Asn His
                270                 275                 280

cgc cag gcg tcc ttg gaa atc tcg cca ata act ttc ctt act gct caa     1623
Arg Gln Ala Ser Leu Glu Ile Ser Pro Ile Thr Phe Leu Thr Ala Gln
            285                 290                 295

aca ctc ttg atg gac ctt gga cag ttt cta ctg ttt tgt cat atc tct     1671
Thr Leu Leu Met Asp Leu Gly Gln Phe Leu Leu Phe Cys His Ile Ser
        300                 305                 310

tcc cac caa cat gat ggc atg gaa gct tat gtc aaa gta gac agc tgt     1719
```

```
Ser His Gln His Asp Gly Met Glu Ala Tyr Val Lys Val Asp Ser Cys
    315                 320                 325

cca gag gaa ccc caa cta cga atg aaa aat aat gaa gaa gcg gaa gac      1767
Pro Glu Glu Pro Gln Leu Arg Met Lys Asn Asn Glu Glu Ala Glu Asp
330                 335                 340                 345

tat gat gat gat ctt act gat tct gaa atg gat gtg gtc agg ttt gat      1815
Tyr Asp Asp Asp Leu Thr Asp Ser Glu Met Asp Val Val Arg Phe Asp
                350                 355                 360

gat gac aac tct cct tcc ttt atc caa att cgc tca gtt gcc aag aag      1863
Asp Asp Asn Ser Pro Ser Phe Ile Gln Ile Arg Ser Val Ala Lys Lys
            365                 370                 375

cat cct aaa act tgg gta cat tac att gct gct gaa gag gag gac tgg      1911
His Pro Lys Thr Trp Val His Tyr Ile Ala Ala Glu Glu Glu Asp Trp
        380                 385                 390

gac tat gct ccc tta gtc ctc gcc ccc gat gac aga agt tat aaa agt      1959
Asp Tyr Ala Pro Leu Val Leu Ala Pro Asp Asp Arg Ser Tyr Lys Ser
    395                 400                 405

caa tat ttg aac aat ggc cct cag cgg att ggt agg aag tac aaa aaa      2007
Gln Tyr Leu Asn Asn Gly Pro Gln Arg Ile Gly Arg Lys Tyr Lys Lys
410                 415                 420                 425

gtc cga ttt atg gca tac aca gat gaa acc ttt aag act cgt gaa gct      2055
Val Arg Phe Met Ala Tyr Thr Asp Glu Thr Phe Lys Thr Arg Glu Ala
                430                 435                 440

att cag cat gaa tca gga atc ttg gga cct tta ctt tat ggg gaa gtt      2103
Ile Gln His Glu Ser Gly Ile Leu Gly Pro Leu Leu Tyr Gly Glu Val
            445                 450                 455

gga gac aca ctg ttg att ata ttt aag aat caa gca agc aga cca tat      2151
Gly Asp Thr Leu Leu Ile Ile Phe Lys Asn Gln Ala Ser Arg Pro Tyr
        460                 465                 470

aac atc tac cct cac gga atc act gat gtc cgt cct ttg tat tca agg      2199
Asn Ile Tyr Pro His Gly Ile Thr Asp Val Arg Pro Leu Tyr Ser Arg
    475                 480                 485

aga tta cca aaa ggt gta aaa cat ttg aag gat ttt cca att ctg cca      2247
Arg Leu Pro Lys Gly Val Lys His Leu Lys Asp Phe Pro Ile Leu Pro
490                 495                 500                 505

gga gaa ata ttc aaa tat aaa tgg aca gtg act gta gaa gat ggg cca      2295
Gly Glu Ile Phe Lys Tyr Lys Trp Thr Val Thr Val Glu Asp Gly Pro
                510                 515                 520

act aaa tca gat cct cgg tgc ctg acc cgc tat tac tct agt ttc gtt      2343
Thr Lys Ser Asp Pro Arg Cys Leu Thr Arg Tyr Tyr Ser Ser Phe Val
            525                 530                 535

aat atg gag aga gat cta gct tca gga ctc att ggc cct ctc ctc atc      2391
Asn Met Glu Arg Asp Leu Ala Ser Gly Leu Ile Gly Pro Leu Leu Ile
        540                 545                 550

tgc tac aaa gaa tct gta gat caa aga gga aac cag ata atg tca gac      2439
Cys Tyr Lys Glu Ser Val Asp Gln Arg Gly Asn Gln Ile Met Ser Asp
    555                 560                 565

aag agg aat gtc atc ctg ttt tct gta ttt gat gag aac cga agc tgg      2487
Lys Arg Asn Val Ile Leu Phe Ser Val Phe Asp Glu Asn Arg Ser Trp
570                 575                 580                 585

tac ctc aca gag aat ata caa cgc ttt ctc ccc aat cca gct gga gtg      2535
Tyr Leu Thr Glu Asn Ile Gln Arg Phe Leu Pro Asn Pro Ala Gly Val
                590                 595                 600

cag ctt gag gat cca gag ttc caa gcc tcc aac atc atg cac agc atc      2583
Gln Leu Glu Asp Pro Glu Phe Gln Ala Ser Asn Ile Met His Ser Ile
            605                 610                 615

aat ggc tat gtt ttt gat agt ttg cag ttg tca gtt tgt ttg cat gag      2631
Asn Gly Tyr Val Phe Asp Ser Leu Gln Leu Ser Val Cys Leu His Glu
        620                 625                 630
```

-continued

```
gtg gca tac tgg tac att cta agc att gga gca cag act gac ttc ctt      2679
Val Ala Tyr Trp Tyr Ile Leu Ser Ile Gly Ala Gln Thr Asp Phe Leu
    635                 640                 645

tct gtc ttc ttc tct gga tat acc ttc aaa cac aaa atg gtc tat gaa      2727
Ser Val Phe Phe Ser Gly Tyr Thr Phe Lys His Lys Met Val Tyr Glu
650                 655                 660                 665

gac aca ctc acc cta ttc cca ttc tca gga gaa act gtc ttc atg tcg      2775
Asp Thr Leu Thr Leu Phe Pro Phe Ser Gly Glu Thr Val Phe Met Ser
                670                 675                 680

atg gaa aac cca ggt cta tgg att ctg ggg tgc cac aac tca gac ttt      2823
Met Glu Asn Pro Gly Leu Trp Ile Leu Gly Cys His Asn Ser Asp Phe
            685                 690                 695

cgg aac aga ggc atg acc gcc tta ctg aag gtt tct agt tgt gac aag      2871
Arg Asn Arg Gly Met Thr Ala Leu Leu Lys Val Ser Ser Cys Asp Lys
        700                 705                 710

aac act ggt gat tat tac gag gac agt tat gaa gat att tca gca tac      2919
Asn Thr Gly Asp Tyr Tyr Glu Asp Ser Tyr Glu Asp Ile Ser Ala Tyr
    715                 720                 725

ttg ctg agt aaa aac aat gcc att gaa cca aga agc ttc tcc cag aat      2967
Leu Leu Ser Lys Asn Asn Ala Ile Glu Pro Arg Ser Phe Ser Gln Asn
730                 735                 740                 745

tca aga cat caa gct tat cga tac cgt cga ggg gaa ata act cgt act      3015
Ser Arg His Gln Ala Tyr Arg Tyr Arg Arg Gly Glu Ile Thr Arg Thr
                750                 755                 760

act ctt cag tca gat caa gag gaa att gac tat gat gat acc ata tca      3063
Thr Leu Gln Ser Asp Gln Glu Glu Ile Asp Tyr Asp Asp Thr Ile Ser
            765                 770                 775

gtt gaa atg aag aag gaa gat ttt gac att tat gat gag gat gaa aat      3111
Val Glu Met Lys Lys Glu Asp Phe Asp Ile Tyr Asp Glu Asp Glu Asn
        780                 785                 790

cag agc ccc cgc agc ttt caa aag aaa aca cga cac tat ttt att gct      3159
Gln Ser Pro Arg Ser Phe Gln Lys Lys Thr Arg His Tyr Phe Ile Ala
    795                 800                 805

gca gtg gag agg ctc tgg gat tat ggg atg agt agc tcc cca cat gtt      3207
Ala Val Glu Arg Leu Trp Asp Tyr Gly Met Ser Ser Ser Pro His Val
810                 815                 820                 825

cta aga aac agg gct cag agt ggc agt gtc cct cag ttc aag aaa gtt      3255
Leu Arg Asn Arg Ala Gln Ser Gly Ser Val Pro Gln Phe Lys Lys Val
                830                 835                 840

gtt ttc cag gaa ttt act gat ggc tcc ttt act cag ccc tta tac cgt      3303
Val Phe Gln Glu Phe Thr Asp Gly Ser Phe Thr Gln Pro Leu Tyr Arg
            845                 850                 855

gga gaa cta aat gaa cat ttg gga ctc ctg ggg cca tat ata aga gca      3351
Gly Glu Leu Asn Glu His Leu Gly Leu Leu Gly Pro Tyr Ile Arg Ala
        860                 865                 870

gaa gtt gaa gat aat atc atg gta act ttc aga aat cag gcc tct cgt      3399
Glu Val Glu Asp Asn Ile Met Val Thr Phe Arg Asn Gln Ala Ser Arg
    875                 880                 885

ccc tat tcc ttc tat tct agc ctt att tct tat gag gaa gat cag agg      3447
Pro Tyr Ser Phe Tyr Ser Ser Leu Ile Ser Tyr Glu Glu Asp Gln Arg
890                 895                 900                 905

caa gga gca gaa cct aga aaa aac ttt gtc aag cct aat gaa acc aaa      3495
Gln Gly Ala Glu Pro Arg Lys Asn Phe Val Lys Pro Asn Glu Thr Lys
                910                 915                 920

act tac ttt tgg aaa gtg caa cat cat atg gca ccc act aaa gat gag      3543
Thr Tyr Phe Trp Lys Val Gln His His Met Ala Pro Thr Lys Asp Glu
            925                 930                 935

ttt gac tgc aaa gcc tgg gct tat ttc tct gat gtt gac ctg gaa aaa      3591
Phe Asp Cys Lys Ala Trp Ala Tyr Phe Ser Asp Val Asp Leu Glu Lys
        940                 945                 950
```

```
gat gtg cac tca ggc ctg att gga ccc ctt ctg gtc tgc cac act aac      3639
Asp Val His Ser Gly Leu Ile Gly Pro Leu Leu Val Cys His Thr Asn
    955                 960                 965

aca ctg aac cct gct cat ggg aga caa gtg aca gta cag gaa ttt gct      3687
Thr Leu Asn Pro Ala His Gly Arg Gln Val Thr Val Gln Glu Phe Ala
970                 975                 980                 985

ctg ttt ttc acc atc ttt gat gag acc aaa agc tgg tac ttc act  gaa     3735
Leu Phe Phe Thr Ile Phe Asp Glu Thr Lys Ser Trp Tyr Phe Thr  Glu
                990                 995                1000

aat atg gaa aga  aac tgc agg gct ccc  tgc aat atc cag atg  gaa       3780
Asn Met Glu Arg  Asn Cys Arg Ala Pro  Cys Asn Ile Gln Met  Glu
            1005                 1010                 1015

gat ccc act ttt  aaa gag aat tat cgc  ttc cat gca atc aat  ggc       3825
Asp Pro Thr Phe  Lys Glu Asn Tyr Arg  Phe His Ala Ile Asn  Gly
            1020                 1025                 1030

tac ata atg gat  aca cta cct ggc tta  gta atg gct cag gat  caa       3870
Tyr Ile Met Asp  Thr Leu Pro Gly Leu  Val Met Ala Gln Asp  Gln
            1035                 1040                 1045

agg att cga tgg  tat ctg ctc agc atg  ggc agc aat gaa aac  atc       3915
Arg Ile Arg Trp  Tyr Leu Leu Ser Met  Gly Ser Asn Glu Asn  Ile
            1050                 1055                 1060

cat tct att cat  ttc agt gga cat gtg  ttc act gta cga aaa  aaa       3960
His Ser Ile His  Phe Ser Gly His Val  Phe Thr Val Arg Lys  Lys
            1065                 1070                 1075

gag gag tat aaa  atg gca ctg tac aat  ctc tat cca ggt gtt  ttt       4005
Glu Glu Tyr Lys  Met Ala Leu Tyr Asn  Leu Tyr Pro Gly Val  Phe
            1080                 1085                 1090

gag aca gtg gaa  atg tta cca tcc aaa  gct gga att tgg cgg  gtg       4050
Glu Thr Val Glu  Met Leu Pro Ser Lys  Ala Gly Ile Trp Arg  Val
            1095                 1100                 1105

gaa tgc ctt att  ggc gag cat cta cat  gct ggg atg agc aca  ctt       4095
Glu Cys Leu Ile  Gly Glu His Leu His  Ala Gly Met Ser Thr  Leu
            1110                 1115                 1120

ttt ctg gtg tac  agc aat aag tgt cag  act ccc ctg gga atg  gct       4140
Phe Leu Val Tyr  Ser Asn Lys Cys Gln  Thr Pro Leu Gly Met  Ala
            1125                 1130                 1135

tct gga cac att  aga gat ttt cag att  aca gct tca gga caa  tat       4185
Ser Gly His Ile  Arg Asp Phe Gln Ile  Thr Ala Ser Gly Gln  Tyr
            1140                 1145                 1150

gga cag tgg gcc  cca aag ctg gcc aga  ctt cat tat tcc gga  tca       4230
Gly Gln Trp Ala  Pro Lys Leu Ala Arg  Leu His Tyr Ser Gly  Ser
            1155                 1160                 1165

atc aat gcc tgg  agc acc aag gag ccc  ttt tct tgg atc aag  gtg       4275
Ile Asn Ala Trp  Ser Thr Lys Glu Pro  Phe Ser Trp Ile Lys  Val
            1170                 1175                 1180

gat ctg ttg gca  cca atg att att cac  ggc atc aag acc cag  ggt       4320
Asp Leu Leu Ala  Pro Met Ile Ile His  Gly Ile Lys Thr Gln  Gly
            1185                 1190                 1195

gcc cgt cag aag  ttc tcc agc ctc tac  atc tct cag ttt atc  atc       4365
Ala Arg Gln Lys  Phe Ser Ser Leu Tyr  Ile Ser Gln Phe Ile  Ile
            1200                 1205                 1210

atg tat agt ctt  gat ggg aag aag tgg  cag act tat cga gga  aat       4410
Met Tyr Ser Leu  Asp Gly Lys Lys Trp  Gln Thr Tyr Arg Gly  Asn
            1215                 1220                 1225

tcc act gga acc  tta atg gtc ttc ttt  ggc aat gtg gat tca  tct       4455
Ser Thr Gly Thr  Leu Met Val Phe Phe  Gly Asn Val Asp Ser  Ser
            1230                 1235                 1240

ggg ata aaa cac  aat att ttt aac cct  cca att att gct cga  tac       4500
Gly Ile Lys His  Asn Ile Phe Asn Pro  Pro Ile Ile Ala Arg  Tyr
```

```
            1245                1250                1255

atc cgt ttg cac  cca act cat tat agc  att cgc agc act ctt  cgc      4545
Ile Arg Leu His  Pro Thr His Tyr Ser  Ile Arg Ser Thr Leu  Arg
            1260                1265                1270

atg gag ttg atg  ggc tgt gat tta aat  agt tgc agc atg cca  ttg      4590
Met Glu Leu Met  Gly Cys Asp Leu Asn  Ser Cys Ser Met Pro  Leu
            1275                1280                1285

gga atg gag agt  aaa gca ata tca gat  gca cag att act gct  tca      4635
Gly Met Glu Ser  Lys Ala Ile Ser Asp  Ala Gln Ile Thr Ala  Ser
            1290                1295                1300

tcc tac ttt acc  aat atg ttt gcc acc  tgg tct cct tca aaa  gct      4680
Ser Tyr Phe Thr  Asn Met Phe Ala Thr  Trp Ser Pro Ser Lys  Ala
            1305                1310                1315

cga ctt cac ctc  caa ggg agg agt aat  gcc tgg aga cct cag  gag      4725
Arg Leu His Leu  Gln Gly Arg Ser Asn  Ala Trp Arg Pro Gln  Glu
            1320                1325                1330

aat aat cca aaa  gag tgg ctg caa gtg  gac ttc cag aag aca  atg      4770
Asn Asn Pro Lys  Glu Trp Leu Gln Val  Asp Phe Gln Lys Thr  Met
            1335                1340                1345

aaa gtc aca gga  gta act act cag gga  gta aaa tct ctg ctt  acc      4815
Lys Val Thr Gly  Val Thr Thr Gln Gly  Val Lys Ser Leu Leu  Thr
            1350                1355                1360

agc atg tat gtg  aag gag ttc ctc atc  tcc agc agt caa gat  ggc      4860
Ser Met Tyr Val  Lys Glu Phe Leu Ile  Ser Ser Ser Gln Asp  Gly
            1365                1370                1375

cat cag tgg acc  ctc ttt ttt cag aat  ggc aaa gta aag gtt  ttt      4905
His Gln Trp Thr  Leu Phe Phe Gln Asn  Gly Lys Val Lys Val  Phe
            1380                1385                1390

cag gga aat caa  gac tcc ttc aca cct  gtg gtg aac tct cta  gac      4950
Gln Gly Asn Gln  Asp Ser Phe Thr Pro  Val Val Asn Ser Leu  Asp
            1395                1400                1405

cca ccg tta ctg  act cgc tac ctt cga  att cac ccc cag agt  tgg      4995
Pro Pro Leu Leu  Thr Arg Tyr Leu Arg  Ile His Pro Gln Ser  Trp
            1410                1415                1420

gtg cac cag att  gcc ctg agg atg gag  gtt ctg ggc tgc gag  gca      5040
Val His Gln Ile  Ala Leu Arg Met Glu  Val Leu Gly Cys Glu  Ala
            1425                1430                1435

cag gac ctc tac  tgagcggccg cgactctact agaggatctt tgtgaaggaa        5092
Gln Asp Leu Tyr
            1440

ccttacttct gtggtgtgac ataattggac aaactaccta cagagattta aagctctaag   5152

gtaaatataa aatttttaag tgtataatgt gttaaactac tgattctaat tgtttgtgta   5212

ttttagattc caacctatgg aactgatgaa tgggagcagt ggtggaatgc ctttaatgag   5272

gaaaacctgt tttgctcaga agaaatgcca tctagtgatg atgaggctac tgctgactct   5332

caacattcta ctcctccaaa aaagaagaga aaggtagaag accccaagga ctttccttca   5392

gaattgctaa gttttttgag tcatgctgtg tttagtaata gaactcttgc ttgctttgct   5452

atttacacca caaaggaaaa agctgcactg ctatacaaga aaattatgga aaaatattct   5512

gtaaccttta taagtaggca taacagttat aatcataaca tactgttttt tcttactcca   5572

cacaggcata gagtgtctgc tattaataac tatgctcaaa aattgtgtac ctttagcttt   5632

ttaatttgta aaggggttaa taaggaatat ttgatgtata gtgccttgac tagagatcat   5692

aatcagccat accacatttg tagaggtttt acttgcttta aaaaacctcc cacacctccc   5752

cctgaacctg aaacataaaa tgaatgcaat tgttgttgtt aacttgttta ttgcagctta   5812

taatggttac aaataaagca atagcatcac aaatttcaca aataaagcat ttttttcact   5872
```

```
gcattctagt tgtggtttgt ccaaactcat caatgtatct tatcatgtct ggatccccg   5932
aacgccagca agacgtagcc cagcgcgtcg gccccgagat gcgccgcgtg cggctgctgg   5992
agatggcgga cgcgatggat atgttctgcc aagggttggt ttgcgcattc acagttctcc   6052
gcaagaattg attggctcca attcttggag tggtgaatcc gttagcgagg tgccgccctg   6112
cttcatcccc gtggcccgtt gctcgcgttt gctggcggtg tccccggaag aaatatattt   6172
gcatgtcttt agttctatga tgacacaaac cccgcccagc gtcttgtcat tggcgaattc   6232
gaacacgcag atgcagtcgg ggcggcgcgg tccgaggtcc acttcgcata ttaaggtgac   6292
gcgtgtggcc tcgaacaccg agcgaccctg cagcgacccg cttaacagcg tcaacagcgt   6352
gccgcagatc agcttgatat gaaaaagcct gaactcaccg cgacgtctgt cgagaagttt   6412
ctgatcgaaa agttcgacag cgtctccgac ctgatgcagc tctcggaggg cgaagaatct   6472
cgtgctttca gcttcgatgt aggagggcgt ggatatgtcc tgcgggtaaa tagctgcgcc   6532
gatggtttct acaaagatcg ttatgtttat cggcactttg catcggccgc gctcccgatt   6592
ccggaagtgc ttgacattgg ggaattcagc gagagcctga cctattgcat ctcccgccgt   6652
gcacagggtg tcacgttgca agacctgcct gaaaccgaac tgcccgctgt tctgcagccg   6712
gtcgcggagg ccatggatgc gatcgctgcg gccgatctta gccagacgag cgggttcggc   6772
ccattcggac cgcaaggaat cggtcaatac actacatggc gtgatttcat atgcgcgatt   6832
gctgatcccc atgtgtatca ctggcaaact gtgatggacg acaccgtcag tgcgtccgtc   6892
gcgcaggctc tcgatgagct gatgctttgg gccgaggact gccccgaagt ccggcacctc   6952
gtgcacgcgg atttcggctc caacaatgtc ctgacggaca atggccgcat aacagcggtc   7012
attgactgga gcgaggcgat gttcggggat tcccaatacg aggtcgccaa catcttcttc   7072
tggaggccgt ggttggcttg tatggagcag cagacgcgct acttcgagcg gaggcatccg   7132
gagcttgcag gatcgccgcg gctccgggcg tatatgctcc gcattggtct tgaccaactc   7192
tatcagagct tggttgacgg caatttcgat gatgcagctt gggcgcaggg tcgatgcgac   7252
gcaatcgtcc gatccggagc cgggactgtc gggcgtacac aaatcgcccg cagaagcgcg   7312
gccgtctgga ccgatggctg tgtagaagta ctcgccgata gtggaaaccg acgccccagc   7372
actcgtccgg atcgggagat gggggaggct aactgaaaca cggaaggaga caataccgga   7432
aggaacccgc gctatgacgg caataaaaag acagaataaa acgcacgggt gttgggtcgt   7492
ttgttcataa acgcggggtt cggtcccagg gctggcactc tgtcgatacc ccaccgagac   7552
cccattgggg ccaatacgcc cgcgtttctt ccttttcccc accccacccc ccaagttcgg   7612
gtgaaggccc agggctcgca gccaacgtcg gggcggcagg ccctgccata gccactggcc   7672
ccgtgggtta gggacggggt cccccatggg gaatggttta tggttcgtgg gggttattat   7732
tttgggcgtt gcgtggggtc aggtccacga ctggactgag cagacagacc catggttttt   7792
ggatggcctg ggcatggacc gcatgtactg gcgcgacacg aacaccgggc gtctgtggct   7852
gccaaacacc cccgaccccc aaaaaccacc gcgcggattt ctggcgtgcc aagctgggta   7912
ccctctagag cgaattaatt cactggccgt cgttttacaa cgtcgtgact gggaaaaccc   7972
tggcgttacc caacttaatc gccttgcagc acatccccct ttcgccagct ggcgtaatag   8032
cgaagaggcc cgcaccgatc gcccttccca acagttgcgc agcctgaatg gcgaatggcg   8092
cctgatgcgg tattttctcc ttacgcatct gtgcggtatt tcacaccgca tatggtgcac   8152
tctcagtaca atctgctctg atgccgcata gttaagccag ccccgacacc cgccaacacc   8212
```

```
cgctgacgcg ccctgacggg cttgtctgct cccggcatcc gcttacagac aagctgtgac   8272

cgtctccggg agctgcatgt gtcagaggtt ttcaccgtca tcaccgaaac gcgcgagacg   8332

aaagggggggg taccagcttc gtagctagaa catcatgttc tgggatatca gcttcgtagc   8392

tagaacatca tgttctggta ccccccctcgt gatacgccta tttttatagg ttaatgtcat   8452

gataataatg gtttcttaga cgtcaggtgg cacttttcgg ggaaatgtgc gcggaacccc   8512

tatttgttta tttttctaaa tacattcaaa tatgtatccg ctcatgagac aataaccctg   8572

ataaatgctt caataatatt gaaaaaggaa gagtatgagt attcaacatt tccgtgtcgc   8632

ccttattccc ttttttgcgg cattttgcct tcctgttttt gctcacccag aaacgctggt   8692

gaaagtaaaa gatgctgaag atcagttggg tgcacgagtg ggttacatcg aactggatct   8752

caacagcggt aagatccttg agagttttcg ccccgaagaa cgttttccaa tgatgagcac   8812

ttttaaagtt ctgctatgtg gcgcggtatt atcccgtatt gacgccgggc aagagcaact   8872

cggtcgccgc atacactatt ctcagaatga cttggttgag tactcaccag tcacagaaaa   8932

gcatcttacg gatggcatga cagtaagaga attatgcagt gctgccataa ccatgagtga   8992

taacactgcg gccaacttac ttctgacaac gatcggagga ccgaaggagc taaccgcttt   9052

tttgcacaac atgggggatc atgtaactcg ccttgatcgt tgggaaccgg agctgaatga   9112

agccatacca aacgacgagc gtgacaccac gatgcctgta gcaatggcaa caacgttgcg   9172

caaactatta actggcgaac tacttactct agcttcccgg caacaattaa tagactggat   9232

ggaggcggat aaagttgcag gaccacttct gcgctcggcc cttccggctg gctggtttat   9292

tgctgataaa tctggagccg gtgagcgtgg gtctcgcggt atcattgcag cactggggcc   9352

agatggtaag ccctcccgta tcgtagttat ctacacgacg gggagtcagg caactatgga   9412

tgaacgaaat agacagatcg ctgagatagg tgcctcactg attaagcatt ggtaactgtc   9472

agaccaagtt tactcatata tactttagat tgatttaaaa cttcattttt aatttaaaag   9532

gatctaggtg aagatccttt ttgataatct catgaccaaa atcccttaac gtgagttttc   9592

gttccactga gcgtcagacc ccgtagaaaa gatcaaagga tcttcttgag atcctttttt   9652

tctgcgcgta atctgctgct tgcaaacaaa aaaaccaccg ctaccagcgg tggtttgttt   9712

gccggatcaa gagctaccaa ctctttttcc gaaggtaact ggcttcagca gagcgcagat   9772

accaaatact gttcttctag tgtagccgta gttaggccac cacttcaaga actctgtagc   9832

accgcctaca tacctcgctc tgctaatcct gttaccagtg gctgctgcca gtggcgataa   9892

gtcgtgtctt accgggttgg actcaagacg atagttaccg gataaggcgc agcggtcggg   9952

ctgaacgggg ggttcgtgca cacagcccag cttggagcga acgacctaca ccgaactgag  10012

atacctacag cgtgagctat gagaaagcgc cacgcttccc gaagggagaa aggcggacag  10072

gtatccggta agcggcaggg tcggaacagg agagcgcacg agggagcttc caggggggaaa  10132

cgcctggtat ctttatagtc ctgtcgggtt tcgccacctc tgacttgagc gtcgattttt  10192

gtgatgctcg tcaggggggc ggagcctatg gaaaaacgcc agcaacgcgg cctttttacg  10252

gttcctggcc ttttgctggc cttttgctca catgttcttt cctgcgttat cccctgattc  10312

tgtggataac cgtattaccg cctttgagtg agctgatacc gctcgccgca gccgaacgac  10372

cgagcgcagc gagtcagtga gcgaggaagc ggaagagcgc ccaatacgca aaccgcctct  10432

ccccgcgcgt tggccgattc attaatgcag ctggcacgac aggtttcccg actggaaagc  10492

gggcagtgag cgcaacgcaa ttaatgtgag ttagctcact cattaggcac cccaggcttt  10552

acactttatg cttccggctc gtatgttgtg tggaattgtg agcggataac aatttcacac  10612
```

```
aggaaacagc tatgaccatg attacgccaa gctctctaga gctctagagc tctagagctc  10672

tagagagctt gcatgcctgc aggtcg                                       10698


<210> SEQ ID NO 4
<211> LENGTH: 1459
<212> TYPE: PRT
<213> ORGANISM: Artificial Sequence
<220> FEATURE:
<223> OTHER INFORMATION: Description of Artificial Sequence: pTGF8-3

<400> SEQUENCE: 4

Met Gln Ile Glu Leu Ser Thr Cys Phe Phe Leu Cys Leu Leu Arg Phe
                -15                 -10                 -5

Cys Phe Ser Ala Thr Arg Arg Tyr Tyr Leu Gly Ala Val Glu Leu Ser
        -1  1               5                   10

Trp Asp Tyr Met Gln Ser Asp Leu Gly Glu Leu Pro Val Asp Ala Arg
    15                  20                  25

Phe Pro Pro Arg Val Pro Lys Ser Phe Pro Phe Asn Thr Ser Val Val
30                  35                  40                  45

Tyr Lys Lys Thr Leu Phe Val Glu Phe Thr Asp His Leu Phe Asn Ile
                50                  55                  60

Ala Lys Pro Arg Pro Pro Trp Met Gly Leu Leu Gly Pro Thr Ile Gln
            65                  70                  75

Ala Glu Val Tyr Asp Thr Val Val Ile Thr Leu Lys Asn Met Ala Ser
        80                  85                  90

His Pro Val Ser Leu His Ala Val Gly Val Ser Tyr Trp Lys Ala Ser
    95                  100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
            145                 150                 155

Tyr Leu Ser His Ala Asp Leu Val Lys Asp Leu Asn Ser Gly Leu Ile
        160                 165                 170

Gly Ala Leu Leu Val Cys Arg Glu Gly Ser Leu Ala Lys Glu Lys Thr
    175                 180                 185

Gln Thr Leu His Lys Phe Ile Leu Leu Phe Ala Val Phe Asp Glu Gly
190                 195                 200                 205

Lys Ser Trp His Ser Glu Thr Lys Asn Ser Leu Met Gln Asp Arg Asp
                210                 215                 220

Ala Ala Ser Ala Arg Ala Trp Pro Lys Met His Thr Val Asn Gly Tyr
            225                 230                 235

Val Asn Arg Ser Leu Pro Gly Leu Ile Gly Cys His Arg Lys Ser Val
        240                 245                 250

Tyr Trp His Val Ile Gly Met Gly Thr Thr Pro Glu Val His Ser Ile
    255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
                290                 295                 300

Asp Leu Gly Gln Phe Leu Leu Phe Cys His Ile Ser Ser His Gln His
            305                 310                 315

Asp Gly Met Glu Ala Tyr Val Lys Val Asp Ser Cys Pro Glu Glu Pro
```

-continued

```
        320                 325                 330

Gln Leu Arg Met Lys Asn Asn Glu Glu Ala Glu Asp Tyr Asp Asp Asp
    335                 340                 345

Leu Thr Asp Ser Glu Met Asp Val Val Arg Phe Asp Asp Asp Asn Ser
350                 355                 360                 365

Pro Ser Phe Ile Gln Ile Arg Ser Val Ala Lys Lys His Pro Lys Thr
                370                 375                 380

Trp Val His Tyr Ile Ala Ala Glu Glu Glu Asp Trp Asp Tyr Ala Pro
            385                 390                 395

Leu Val Leu Ala Pro Asp Asp Arg Ser Tyr Lys Ser Gln Tyr Leu Asn
        400                 405                 410

Asn Gly Pro Gln Arg Ile Gly Arg Lys Tyr Lys Lys Val Arg Phe Met
    415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Gln Ala Ser Arg Pro Tyr Asn Ile Tyr Pro
            465                 470                 475

His Gly Ile Thr Asp Val Arg Pro Leu Tyr Ser Arg Arg Leu Pro Lys
        480                 485                 490

Gly Val Lys His Leu Lys Asp Phe Pro Ile Leu Pro Gly Glu Ile Phe
    495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
                530                 535                 540

Asp Leu Ala Ser Gly Leu Ile Gly Pro Leu Leu Ile Cys Tyr Lys Glu
            545                 550                 555

Ser Val Asp Gln Arg Gly Asn Gln Ile Met Ser Asp Lys Arg Asn Val
        560                 565                 570

Ile Leu Phe Ser Val Phe Asp Glu Asn Arg Ser Trp Tyr Leu Thr Glu
    575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
            625                 630                 635

Tyr Ile Leu Ser Ile Gly Ala Gln Thr Asp Phe Leu Ser Val Phe Phe
        640                 645                 650

Ser Gly Tyr Thr Phe Lys His Lys Met Val Tyr Glu Asp Thr Leu Thr
    655                 660                 665

Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
                690                 695                 700

Met Thr Ala Leu Leu Lys Val Ser Ser Cys Asp Lys Asn Thr Gly Asp
            705                 710                 715

Tyr Tyr Glu Asp Ser Tyr Glu Asp Ile Ser Ala Tyr Leu Leu Ser Lys
        720                 725                 730

Asn Asn Ala Ile Glu Pro Arg Ser Phe Ser Gln Asn Ser Arg His Gln
    735                 740                 745
```

```
Ala Tyr Arg Tyr Arg Arg Gly Glu Ile Thr Arg Thr Thr Leu Gln Ser
750                 755                 760                 765

Asp Gln Glu Glu Ile Asp Tyr Asp Asp Thr Ile Ser Val Glu Met Lys
                770                 775                 780

Lys Glu Asp Phe Asp Ile Tyr Asp Glu Asp Glu Asn Gln Ser Pro Arg
            785                 790                 795

Ser Phe Gln Lys Lys Thr Arg His Tyr Phe Ile Ala Ala Val Glu Arg
        800                 805                 810

Leu Trp Asp Tyr Gly Met Ser Ser Ser Pro His Val Leu Arg Asn Arg
    815                 820                 825

Ala Gln Ser Gly Ser Val Pro Gln Phe Lys Lys Val Val Phe Gln Glu
830                 835                 840                 845

Phe Thr Asp Gly Ser Phe Thr Gln Pro Leu Tyr Arg Gly Glu Leu Asn
                850                 855                 860

Glu His Leu Gly Leu Leu Gly Pro Tyr Ile Arg Ala Glu Val Glu Asp
            865                 870                 875

Asn Ile Met Val Thr Phe Arg Asn Gln Ala Ser Arg Pro Tyr Ser Phe
        880                 885                 890

Tyr Ser Ser Leu Ile Ser Tyr Glu Glu Asp Gln Arg Gln Gly Ala Glu
    895                 900                 905

Pro Arg Lys Asn Phe Val Lys Pro Asn Glu Thr Lys Thr Tyr Phe Trp
910                 915                 920                 925

Lys Val Gln His His Met Ala Pro Thr Lys Asp Glu Phe Asp Cys Lys
                930                 935                 940

Ala Trp Ala Tyr Phe Ser Asp Val Asp Leu Glu Lys Asp Val His Ser
            945                 950                 955

Gly Leu Ile Gly Pro Leu Leu Val Cys His Thr Asn Thr Leu Asn Pro
        960                 965                 970

Ala His Gly Arg Gln Val Thr Val Gln Glu Phe Ala Leu Phe Phe Thr
    975                 980                 985

Ile Phe Asp Glu Thr Lys Ser Trp Tyr Phe Thr  Glu Asn Met Glu Arg
990                 995                 1000                1005

Asn Cys Arg Ala Pro  Cys Asn Ile Gln Met  Glu Asp Pro Thr Phe
                1010                1015                1020

Lys Glu Asn Tyr Arg  Phe His Ala Ile Asn  Gly Tyr Ile Met Asp
                1025                1030                1035

Thr Leu Pro Gly Leu  Val Met Ala Gln Asp  Gln Arg Ile Arg Trp
                1040                1045                1050

Tyr Leu Leu Ser Met  Gly Ser Asn Glu Asn  Ile His Ser Ile His
                1055                1060                1065

Phe Ser Gly His Val  Phe Thr Val Arg Lys  Lys Glu Glu Tyr Lys
                1070                1075                1080

Met Ala Leu Tyr Asn  Leu Tyr Pro Gly Val  Phe Glu Thr Val Glu
                1085                1090                1095

Met Leu Pro Ser Lys  Ala Gly Ile Trp Arg  Val Glu Cys Leu Ile
                1100                1105                1110

Gly Glu His Leu His  Ala Gly Met Ser Thr  Leu Phe Leu Val Tyr
                1115                1120                1125

Ser Asn Lys Cys Gln  Thr Pro Leu Gly Met  Ala Ser Gly His Ile
                1130                1135                1140

Arg Asp Phe Gln Ile  Thr Ala Ser Gly Gln  Tyr Gly Gln Trp Ala
                1145                1150                1155
```

```
Pro Lys Leu Ala Arg  Leu His Tyr Ser Gly  Ser Ile Asn Ala Trp
                1160                1165                1170

Ser Thr Lys Glu Pro  Phe Ser Trp Ile Lys  Val Asp Leu Leu Ala
                1175                1180                1185

Pro Met Ile Ile His  Gly Ile Lys Thr Gln  Gly Ala Arg Gln Lys
                1190                1195                1200

Phe Ser Ser Leu Tyr  Ile Ser Gln Phe Ile  Ile Met Tyr Ser Leu
                1205                1210                1215

Asp Gly Lys Lys Trp  Gln Thr Tyr Arg Gly  Asn Ser Thr Gly Thr
                1220                1225                1230

Leu Met Val Phe Phe  Gly Asn Val Asp Ser  Ser Gly Ile Lys His
                1235                1240                1245

Asn Ile Phe Asn Pro  Pro Ile Ile Ala Arg  Tyr Ile Arg Leu His
                1250                1255                1260

Pro Thr His Tyr Ser  Ile Arg Ser Thr Leu  Arg Met Glu Leu Met
                1265                1270                1275

Gly Cys Asp Leu Asn  Ser Cys Ser Met Pro  Leu Gly Met Glu Ser
                1280                1285                1290

Lys Ala Ile Ser Asp  Ala Gln Ile Thr Ala  Ser Ser Tyr Phe Thr
                1295                1300                1305

Asn Met Phe Ala Thr  Trp Ser Pro Ser Lys  Ala Arg Leu His Leu
                1310                1315                1320

Gln Gly Arg Ser Asn  Ala Trp Arg Pro Gln  Glu Asn Asn Pro Lys
                1325                1330                1335

Glu Trp Leu Gln Val  Asp Phe Gln Lys Thr  Met Lys Val Thr Gly
                1340                1345                1350

Val Thr Thr Gln Gly  Val Lys Ser Leu Leu  Thr Ser Met Tyr Val
                1355                1360                1365

Lys Glu Phe Leu Ile  Ser Ser Ser Gln Asp  Gly His Gln Trp Thr
                1370                1375                1380

Leu Phe Phe Gln Asn  Gly Lys Val Lys Val  Phe Gln Gly Asn Gln
                1385                1390                1395

Asp Ser Phe Thr Pro  Val Val Asn Ser Leu  Asp Pro Pro Leu Leu
                1400                1405                1410

Thr Arg Tyr Leu Arg  Ile His Pro Gln Ser  Trp Val His Gln Ile
                1415                1420                1425

Ala Leu Arg Met Glu  Val Leu Gly Cys Glu  Ala Gln Asp Leu Tyr
                1430                1435                1440
```

```
<210> SEQ ID NO 5
<211> LENGTH: 10698
<212> TYPE: DNA
<213> ORGANISM: Artificial Sequence
<220> FEATURE:
<223> OTHER INFORMATION: Description of Artificial Sequence:
      pTGF8-2hyg-s
<220> FEATURE:
<221> NAME/KEY: CDS
<222> LOCATION: (676)..(5052)
<220> FEATURE:
<221> NAME/KEY: mat_peptide
<222> LOCATION: (733)..(5052)

<400> SEQUENCE: 5

cgcgttgaca ttgattattg actagttatt aatagtaatc aattacgggg tcattagttc     60

atagcccata tatggagttc cgcgttacat aacttacggt aaatggcccg cctggctgac    120

cgcccaacga cccccgccca ttgacgtcaa taatgacgta tgttcccata gtaacgccaa    180
```

```
tagggacttt ccattgacgt caatgggtgg agtatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360

acgtattagt catcgctatt accatggtga tgcggttttg gcagtacatc aatgggcgtg    420

gatagcggtt tgactcacgg ggatttccaa gtctccaccc cattgacgtc aatgggagtt    480

tgttttggca ccaaaatcaa cgggactttc caaaatgtcg taacaactcc gccccattga    540

cgcaaatggg cggtaggcgt gtacggtggg aggtctatat aagcagagct ctctggctaa    600

ctagagaacc cactgcttac tggcttatcg aaattaatac gactcactat agggagaccc    660

aagcttgacc tcgag atg caa ata gag ctc tcc acc tgc ttc ttt ctg tgc     711
                 Met Gln Ile Glu Leu Ser Thr Cys Phe Phe Leu Cys
                                 -15                 -10

ctt ttg cga ttc tgc ttt agt gcc acc aga aga tac tac ctg ggt gca      759
Leu Leu Arg Phe Cys Phe Ser Ala Thr Arg Arg Tyr Tyr Leu Gly Ala
        -5              -1  1               5

gtg gaa ctg tca tgg gac tat atg caa agt gat ctc ggt gag ctg cct      807
Val Glu Leu Ser Trp Asp Tyr Met Gln Ser Asp Leu Gly Glu Leu Pro
10                  15                  20                  25

gtg gac gca aga ttt cct cct aga gtg cca aaa tct ttt cca ttc aac      855
Val Asp Ala Arg Phe Pro Pro Arg Val Pro Lys Ser Phe Pro Phe Asn
                30                  35                  40

acc tca gtc gtg tac aaa aag act ctg ttt gta gaa ttc acg gat cac      903
Thr Ser Val Val Tyr Lys Lys Thr Leu Phe Val Glu Phe Thr Asp His
            45                  50                  55

ctt ttc aac atc gct aag cca agg cca ccc tgg atg ggt ctg cta ggt      951
Leu Phe Asn Ile Ala Lys Pro Arg Pro Pro Trp Met Gly Leu Leu Gly
        60                  65                  70

cct acc atc cag gct gag gtt tat gat aca gtg gtc att aca ctt aag      999
Pro Thr Ile Gln Ala Glu Val Tyr Asp Thr Val Val Ile Thr Leu Lys
    75                  80                  85

aac atg gct tcc cat cct gtc agt ctt cat gct gtt ggt gta tcc tac     1047
Asn Met Ala Ser His Pro Val Ser Leu His Ala Val Gly Val Ser Tyr
90                  95                  100                 105

tgg aaa gct tct gag gga gct gaa tat gat gat cag acc agt caa agg     1095
Trp Lys Ala Ser Glu Gly Ala Glu Tyr Asp Asp Gln Thr Ser Gln Arg
                110                 115                 120

gag aaa gaa gat gat aaa gtc ttc cct ggt gga agc cat aca tat gtc     1143
Glu Lys Glu Asp Asp Lys Val Phe Pro Gly Gly Ser His Thr Tyr Val
            125                 130                 135

tgg cag gtc ctg aaa gag aat ggt cca atg gcc tct gac cca ctg tgc     1191
Trp Gln Val Leu Lys Glu Asn Gly Pro Met Ala Ser Asp Pro Leu Cys
        140                 145                 150

ctt acc tac tca tat ctt tct cat gtg gac ctg gta aaa gac ttg aat     1239
Leu Thr Tyr Ser Tyr Leu Ser His Val Asp Leu Val Lys Asp Leu Asn
    155                 160                 165

tca ggc ctc att gga gcc cta cta gta tgt aga gaa ggg agt ctg gcc     1287
Ser Gly Leu Ile Gly Ala Leu Leu Val Cys Arg Glu Gly Ser Leu Ala
170                 175                 180                 185

aag gaa aag aca cag acc ttg cac aaa ttt ata cta ctt ttt gct gta     1335
Lys Glu Lys Thr Gln Thr Leu His Lys Phe Ile Leu Leu Phe Ala Val
                190                 195                 200

ttt gat gaa ggg aaa agt tgg cac tca gaa aca aag aac tcc ttg atg     1383
Phe Asp Glu Gly Lys Ser Trp His Ser Glu Thr Lys Asn Ser Leu Met
            205                 210                 215

cag gat agg gat gct gca tct gct cgg gcc tgg cct aaa atg cac aca     1431
Gln Asp Arg Asp Ala Ala Ser Ala Arg Ala Trp Pro Lys Met His Thr
```

```
        220                 225                 230

gtc aat ggt tat gta aac agg tct ctg cca ggt ctg att gga tgc cac      1479
Val Asn Gly Tyr Val Asn Arg Ser Leu Pro Gly Leu Ile Gly Cys His
    235                 240                 245

agg aaa tca gtc tat tgg cat gtg att gga atg ggc acc act cct gaa      1527
Arg Lys Ser Val Tyr Trp His Val Ile Gly Met Gly Thr Thr Pro Glu
250                 255                 260                 265

gtg cac tca ata ttc ctc gaa ggt cac aca ttt ctt gtg agg aac cat      1575
Val His Ser Ile Phe Leu Glu Gly His Thr Phe Leu Val Arg Asn His
                270                 275                 280

cgc cag gcg tcc ttg gaa atc tcg cca ata act ttc ctt act gct caa      1623
Arg Gln Ala Ser Leu Glu Ile Ser Pro Ile Thr Phe Leu Thr Ala Gln
            285                 290                 295

aca ctc ttg atg gac ctt gga cag ttt cta ctg ttt tgt cat atc tct      1671
Thr Leu Leu Met Asp Leu Gly Gln Phe Leu Leu Phe Cys His Ile Ser
        300                 305                 310

tcc cac caa cat gat ggc atg gaa gct tat gtc aaa gta gac agc tgt      1719
Ser His Gln His Asp Gly Met Glu Ala Tyr Val Lys Val Asp Ser Cys
    315                 320                 325

cca gag gaa ccc caa cta cga atg aaa aat aat gaa gaa gcg gaa gac      1767
Pro Glu Glu Pro Gln Leu Arg Met Lys Asn Asn Glu Glu Ala Glu Asp
330                 335                 340                 345

tat gat gat gat ctt act gat tct gaa atg gat gtg gtc agg ttt gat      1815
Tyr Asp Asp Asp Leu Thr Asp Ser Glu Met Asp Val Val Arg Phe Asp
                350                 355                 360

gat gac aac tct cct tcc ttt atc caa att cgc tca gtt gcc aag aag      1863
Asp Asp Asn Ser Pro Ser Phe Ile Gln Ile Arg Ser Val Ala Lys Lys
            365                 370                 375

cat cct aaa act tgg gta cat tac att gct gct gaa gag gag gac tgg      1911
His Pro Lys Thr Trp Val His Tyr Ile Ala Ala Glu Glu Glu Asp Trp
        380                 385                 390

gac tat gct ccc tta gtc ctc gcc ccc gat gac aga agt tat aaa agt      1959
Asp Tyr Ala Pro Leu Val Leu Ala Pro Asp Asp Arg Ser Tyr Lys Ser
    395                 400                 405

caa tat ttg aac aat ggc cct cag cgg att ggt agg aag tac aaa aaa      2007
Gln Tyr Leu Asn Asn Gly Pro Gln Arg Ile Gly Arg Lys Tyr Lys Lys
410                 415                 420                 425

gtc cga ttt atg gca tac aca gat gaa acc ttt aag act cgt gaa gct      2055
Val Arg Phe Met Ala Tyr Thr Asp Glu Thr Phe Lys Thr Arg Glu Ala
                430                 435                 440

att cag cat gaa tca gga atc ttg gga cct tta ctt tat ggg gaa gtt      2103
Ile Gln His Glu Ser Gly Ile Leu Gly Pro Leu Leu Tyr Gly Glu Val
            445                 450                 455

gga gac aca ctg ttg att ata ttt aag aat caa gca agc aga cca tat      2151
Gly Asp Thr Leu Leu Ile Ile Phe Lys Asn Gln Ala Ser Arg Pro Tyr
        460                 465                 470

aac atc tac cct cac gga atc act gat gtc cgt cct ttg tat tca agg      2199
Asn Ile Tyr Pro His Gly Ile Thr Asp Val Arg Pro Leu Tyr Ser Arg
    475                 480                 485

aga tta cca aaa ggt gta aaa cat ttg aag gat ttt cca att ctg cca      2247
Arg Leu Pro Lys Gly Val Lys His Leu Lys Asp Phe Pro Ile Leu Pro
490                 495                 500                 505

gga gaa ata ttc aaa tat aaa tgg aca gtg act gta gaa gat ggg cca      2295
Gly Glu Ile Phe Lys Tyr Lys Trp Thr Val Thr Val Glu Asp Gly Pro
                510                 515                 520

act aaa tca gat cct cgg tgc ctg acc cgc tat tac tct agt ttc gtt      2343
Thr Lys Ser Asp Pro Arg Cys Leu Thr Arg Tyr Tyr Ser Ser Phe Val
            525                 530                 535

aat atg gag aga gat cta gct tca gga ctc att ggc cct ctc ctc atc      2391
```

-continued

```
Asn Met Glu Arg Asp Leu Ala Ser Gly Leu Ile Gly Pro Leu Leu Ile
        540                 545                 550

tgc tac aaa gaa tct gta gat caa aga gga aac cag ata atg tca gac     2439
Cys Tyr Lys Glu Ser Val Asp Gln Arg Gly Asn Gln Ile Met Ser Asp
    555                 560                 565

aag agg aat gtc atc ctg ttt tct gta ttt gat gag aac cga agc tgg     2487
Lys Arg Asn Val Ile Leu Phe Ser Val Phe Asp Glu Asn Arg Ser Trp
570                 575                 580                 585

tac ctc aca gag aat ata caa cgc ttt ctc ccc aat cca gct gga gtg     2535
Tyr Leu Thr Glu Asn Ile Gln Arg Phe Leu Pro Asn Pro Ala Gly Val
                590                 595                 600

cag ctt gag gat cca gag ttc caa gcc tcc aac atc atg cac agc atc     2583
Gln Leu Glu Asp Pro Glu Phe Gln Ala Ser Asn Ile Met His Ser Ile
            605                 610                 615

aat ggc tat gtt ttt gat agt ttg cag ttg tca gtt tgt ttg cat gag     2631
Asn Gly Tyr Val Phe Asp Ser Leu Gln Leu Ser Val Cys Leu His Glu
        620                 625                 630

gtg gca tac tgg tac att cta agc att gga gca cag act gac ttc ctt     2679
Val Ala Tyr Trp Tyr Ile Leu Ser Ile Gly Ala Gln Thr Asp Phe Leu
    635                 640                 645

tct gtc ttc ttc tct gga tat acc ttc aaa cac aaa atg gtc tat gaa     2727
Ser Val Phe Phe Ser Gly Tyr Thr Phe Lys His Lys Met Val Tyr Glu
650                 655                 660                 665

gac aca ctc acc cta ttc cca ttc tca gga gaa act gtc ttc atg tcg     2775
Asp Thr Leu Thr Leu Phe Pro Phe Ser Gly Glu Thr Val Phe Met Ser
                670                 675                 680

atg gaa aac cca ggt cta tgg att ctg ggg tgc cac aac tca gac ttt     2823
Met Glu Asn Pro Gly Leu Trp Ile Leu Gly Cys His Asn Ser Asp Phe
            685                 690                 695

cgg aac aga ggc atg acc gcc tta ctg aag gtt tct agt tgt gac aag     2871
Arg Asn Arg Gly Met Thr Ala Leu Leu Lys Val Ser Ser Cys Asp Lys
        700                 705                 710

aac act ggt gat tat tac gag gac agt tat gaa gat att tca gca tac     2919
Asn Thr Gly Asp Tyr Tyr Glu Asp Ser Tyr Glu Asp Ile Ser Ala Tyr
    715                 720                 725

ttg ctg agt aaa aac aat gcc att gaa cca aga agc ttc tcc cag aat     2967
Leu Leu Ser Lys Asn Asn Ala Ile Glu Pro Arg Ser Phe Ser Gln Asn
730                 735                 740                 745

tca aga cat caa gct tat cga tac cgt cga ggg gaa ata act cgt act     3015
Ser Arg His Gln Ala Tyr Arg Tyr Arg Arg Gly Glu Ile Thr Arg Thr
                750                 755                 760

act ctt cag tca gat caa gag gaa att gac tat gat gat acc ata tca     3063
Thr Leu Gln Ser Asp Gln Glu Glu Ile Asp Tyr Asp Asp Thr Ile Ser
            765                 770                 775

gtt gaa atg aag aag gaa gat ttt gac att tat gat gag gat gaa aat     3111
Val Glu Met Lys Lys Glu Asp Phe Asp Ile Tyr Asp Glu Asp Glu Asn
        780                 785                 790

cag agc ccc cgc agc ttt caa aag aaa aca cga cac tat ttt att gct     3159
Gln Ser Pro Arg Ser Phe Gln Lys Lys Thr Arg His Tyr Phe Ile Ala
    795                 800                 805

gca gtg gag agg ctc tgg gat tat ggg atg agt agc tcc cca cat gtt     3207
Ala Val Glu Arg Leu Trp Asp Tyr Gly Met Ser Ser Ser Pro His Val
810                 815                 820                 825

cta aga aac agg gct cag agt ggc agt gtc cct cag ttc aag aaa gtt     3255
Leu Arg Asn Arg Ala Gln Ser Gly Ser Val Pro Gln Phe Lys Lys Val
                830                 835                 840

gtt ttc cag gaa ttt act gat ggc tcc ttt act cag ccc tta tac cgt     3303
Val Phe Gln Glu Phe Thr Asp Gly Ser Phe Thr Gln Pro Leu Tyr Arg
            845                 850                 855
```

```
gga gaa cta aat gaa cat ttg gga ctc ctg ggg cca tat ata aga gca     3351
Gly Glu Leu Asn Glu His Leu Gly Leu Leu Gly Pro Tyr Ile Arg Ala
        860                 865                 870

gaa gtt gaa gat aat atc atg gta act ttc aga aat cag gcc tct cgt     3399
Glu Val Glu Asp Asn Ile Met Val Thr Phe Arg Asn Gln Ala Ser Arg
    875                 880                 885

ccc tat tcc ttc tat tct agc ctt att tct tat gag gaa gat cag agg     3447
Pro Tyr Ser Phe Tyr Ser Ser Leu Ile Ser Tyr Glu Glu Asp Gln Arg
890                 895                 900                 905

caa gga gca gaa cct aga aaa aac ttt gtc aag cct aat gaa acc aaa     3495
Gln Gly Ala Glu Pro Arg Lys Asn Phe Val Lys Pro Asn Glu Thr Lys
                910                 915                 920

act tac ttt tgg aaa gtg caa cat cat atg gca ccc act aaa gat gag     3543
Thr Tyr Phe Trp Lys Val Gln His His Met Ala Pro Thr Lys Asp Glu
            925                 930                 935

ttt gac tgc aaa gcc tgg gct tat ttc tct gat gtt gac ctg gaa aaa     3591
Phe Asp Cys Lys Ala Trp Ala Tyr Phe Ser Asp Val Asp Leu Glu Lys
        940                 945                 950

gat gtg cac tca ggc ctg att gga ccc ctt ctg gtc tgc cac act aac     3639
Asp Val His Ser Gly Leu Ile Gly Pro Leu Leu Val Cys His Thr Asn
    955                 960                 965

aca ctg aac cct gct cat ggg aga caa gtg aca gta cag gaa ttt gct     3687
Thr Leu Asn Pro Ala His Gly Arg Gln Val Thr Val Gln Glu Phe Ala
970                 975                 980                 985

ctg ttt ttc acc atc ttt gat gag acc aaa agc tgg tac ttc act  gaa    3735
Leu Phe Phe Thr Ile Phe Asp Glu Thr Lys Ser Trp Tyr Phe Thr  Glu
                990                 995                 1000

aat atg gaa aga  aac tgc agg gct ccc  tgc aat atc cag atg  gaa      3780
Asn Met Glu Arg  Asn Cys Arg Ala Pro  Cys Asn Ile Gln Met  Glu
            1005                 1010                 1015

gat ccc act ttt  aaa gag aat tat cgc  ttc cat gca atc aat  ggc      3825
Asp Pro Thr Phe  Lys Glu Asn Tyr Arg  Phe His Ala Ile Asn  Gly
            1020                 1025                 1030

tac ata atg gat  aca cta cct ggc tta  gta atg gct cag gat  caa      3870
Tyr Ile Met Asp  Thr Leu Pro Gly Leu  Val Met Ala Gln Asp  Gln
            1035                 1040                 1045

agg att cga tgg  tat ctg ctc agc atg  ggc agc aat gaa aac  atc      3915
Arg Ile Arg Trp  Tyr Leu Leu Ser Met  Gly Ser Asn Glu Asn  Ile
            1050                 1055                 1060

cat tct att cat  ttc agt gga cat gtg  ttc act gta cga aaa  aaa      3960
His Ser Ile His  Phe Ser Gly His Val  Phe Thr Val Arg Lys  Lys
            1065                 1070                 1075

gag gag tat aaa  atg gca ctg tac aat  ctc tat cca ggt gtt  ttt      4005
Glu Glu Tyr Lys  Met Ala Leu Tyr Asn  Leu Tyr Pro Gly Val  Phe
            1080                 1085                 1090

gag aca gtg gaa  atg tta cca tcc aaa  gct gga att tgg cgg  gtg      4050
Glu Thr Val Glu  Met Leu Pro Ser Lys  Ala Gly Ile Trp Arg  Val
            1095                 1100                 1105

gaa tgc ctt att  ggc gag cat cta cat  gct ggg atg agc aca  ctt      4095
Glu Cys Leu Ile  Gly Glu His Leu His  Ala Gly Met Ser Thr  Leu
            1110                 1115                 1120

ttt ctg gtg tac  agc aat aag tgt cag  act ccc ctg gga atg  gct      4140
Phe Leu Val Tyr  Ser Asn Lys Cys Gln  Thr Pro Leu Gly Met  Ala
            1125                 1130                 1135

tct gga cac att  aga gat ttt cag att  aca gct tca gga caa  tat      4185
Ser Gly His Ile  Arg Asp Phe Gln Ile  Thr Ala Ser Gly Gln  Tyr
            1140                 1145                 1150

gga cag tgg gcc  cca aag ctg gcc aga  ctt cat tat tcc gga  tca      4230
Gly Gln Trp Ala  Pro Lys Leu Ala Arg  Leu His Tyr Ser Gly  Ser
            1155                 1160                 1165
```

```
atc aat gcc tgg  agc acc aag gag ccc  ttt tct tgg atc aag  gtg      4275
Ile Asn Ala Trp  Ser Thr Lys Glu Pro  Phe Ser Trp Ile Lys  Val
            1170                 1175                 1180

gat ctg ttg gca  cca atg att att cac  ggc atc aag acc cag  ggt      4320
Asp Leu Leu Ala  Pro Met Ile Ile His  Gly Ile Lys Thr Gln  Gly
            1185                 1190                 1195

gcc cgt cag aag  ttc tcc agc ctc tac  atc tct cag ttt atc  atc      4365
Ala Arg Gln Lys  Phe Ser Ser Leu Tyr  Ile Ser Gln Phe Ile  Ile
            1200                 1205                 1210

atg tat agt ctt  gat ggg aag aag tgg  cag act tat cga gga  aat      4410
Met Tyr Ser Leu  Asp Gly Lys Lys Trp  Gln Thr Tyr Arg Gly  Asn
            1215                 1220                 1225

tcc act gga acc  tta atg gtc ttc ttt  ggc aat gtg gat tca  tct      4455
Ser Thr Gly Thr  Leu Met Val Phe Phe  Gly Asn Val Asp Ser  Ser
            1230                 1235                 1240

ggg ata aaa cac  aat att ttt aac cct  cca att att gct cga  tac      4500
Gly Ile Lys His  Asn Ile Phe Asn Pro  Pro Ile Ile Ala Arg  Tyr
            1245                 1250                 1255

atc cgt ttg cac  cca act cat tat agc  att cgc agc act ctt  cgc      4545
Ile Arg Leu His  Pro Thr His Tyr Ser  Ile Arg Ser Thr Leu  Arg
            1260                 1265                 1270

atg gag ttg atg  ggc tgt gat tta aat  agt tgc agc atg cca  ttg      4590
Met Glu Leu Met  Gly Cys Asp Leu Asn  Ser Cys Ser Met Pro  Leu
            1275                 1280                 1285

gga atg gag agt  aaa gca ata tca gat  gca cag att act gct  tca      4635
Gly Met Glu Ser  Lys Ala Ile Ser Asp  Ala Gln Ile Thr Ala  Ser
            1290                 1295                 1300

tcc tac ttt acc  aat atg ttt gcc acc  tgg tct cct tca aaa  gct      4680
Ser Tyr Phe Thr  Asn Met Phe Ala Thr  Trp Ser Pro Ser Lys  Ala
            1305                 1310                 1315

cga ctt cac ctc  caa ggg agg agt aat  gcc tgg aga cct cag  gtg      4725
Arg Leu His Leu  Gln Gly Arg Ser Asn  Ala Trp Arg Pro Gln  Val
            1320                 1325                 1330

aat aat cca aaa  gag tgg ctg caa gtg  gac ttc cag aag aca  atg      4770
Asn Asn Pro Lys  Glu Trp Leu Gln Val  Asp Phe Gln Lys Thr  Met
            1335                 1340                 1345

aaa gtc aca gga  gta act act cag gga  gta aaa tct ctg ctt  acc      4815
Lys Val Thr Gly  Val Thr Thr Gln Gly  Val Lys Ser Leu Leu  Thr
            1350                 1355                 1360

agc atg tat gtg  aag gag ttc ctc atc  tcc agc agt caa gat  ggc      4860
Ser Met Tyr Val  Lys Glu Phe Leu Ile  Ser Ser Ser Gln Asp  Gly
            1365                 1370                 1375

cat cag tgg acc  ctc ttt ttt cag aat  ggc aaa gta aag gtt  ttt      4905
His Gln Trp Thr  Leu Phe Phe Gln Asn  Gly Lys Val Lys Val  Phe
            1380                 1385                 1390

cag gga aat caa  gac tcc ttc aca cct  gtg gtg aac tct cta  gac      4950
Gln Gly Asn Gln  Asp Ser Phe Thr Pro  Val Val Asn Ser Leu  Asp
            1395                 1400                 1405

cca ccg tta ctg  act cgc tac ctt cga  att cac ccc cag agt  tgg      4995
Pro Pro Leu Leu  Thr Arg Tyr Leu Arg  Ile His Pro Gln Ser  Trp
            1410                 1415                 1420

gtg cac cag att  gcc ctg agg atg gag  gtt ctg ggc tgc gag  gca      5040
Val His Gln Ile  Ala Leu Arg Met Glu  Val Leu Gly Cys Glu  Ala
            1425                 1430                 1435

cag gac ctc tac  tgagcggccg cgactctact agaggatctt tgtgaaggaa       5092
Gln Asp Leu Tyr
            1440

ccttacttct gtggtgtgac ataattggac aaactaccta cagagattta aagctctaag   5152
```

-continued

```
gtaaatataa aatttttaag tgtataatgt gttaaactac tgattctaat tgtttgtgta   5212
ttttagattc caacctatgg aactgatgaa tgggagcagt ggtggaatgc ctttaatgag   5272
gaaaacctgt tttgctcaga agaaatgcca tctagtgatg atgaggctac tgctgactct   5332
caacattcta ctcctccaaa aaagaagaga aaggtagaag accccaagga ctttccttca   5392
gaattgctaa gtttttgag tcatgctgtg tttagtaata gaactcttgc ttgctttgct   5452
atttacacca caaaggaaaa agctgcactg ctatacaaga aaattatgga aaaatattct   5512
gtaaccttta taagtaggca taacagttat aatcataaca tactgttttt tcttactcca   5572
cacaggcata gagtgtctgc tattaataac tatgctcaaa aattgtgtac ctttagcttt   5632
ttaatttgta aaggggttaa taaggaatat ttgatgtata gtgccttgac tagagatcat   5692
aatcagccat accacatttg tagaggtttt acttgcttta aaaaacctcc cacacctccc   5752
cctgaacctg aaacataaaa tgaatgcaat tgttgttgtt aacttgttta ttgcagctta   5812
taatggttac aaataaagca atagcatcac aaatttcaca aataaagcat ttttttcact   5872
gcattctagt tgtggtttgt ccaaactcat caatgtatct tatcatgtct ggatcccccg   5932
aacgccagca agacgtagcc cagcgcgtcg gccccgagat gcgccgcgtg cggctgctgg   5992
agatggcgga cgcgatggat atgttctgcc aagggttggt ttgcgcattc acagttctcc   6052
gcaagaattg attggctcca attcttggag tggtgaatcc gttagcgagg tgccgccctg   6112
cttcatcccc gtggcccgtt gctcgcgttt gctggcggtg tccccggaag aaatatattt   6172
gcatgtcttt agttctatga tgacacaaac cccgcccagc gtcttgtcat tggcgaattc   6232
gaacacgcag atgcagtcgg ggcggcgcgg tccgaggtcc acttcgcata ttaaggtgac   6292
gcgtgtggcc tcgaacaccg agcgaccctg cagcgacccg cttaacagcg tcaacagcgt   6352
gccgcagatc agcttgatat gaaaaagcct gaactcaccg cgacgtctgt cgagaagttt   6412
ctgatcgaaa agttcgacag cgtctccgac ctgatgcagc tctcggaggg cgaagaatct   6472
cgtgctttca gcttcgatgt aggagggcgt ggatatgtcc tgcgggtaaa tagctgcgcc   6532
gatggtttct acaaagatcg ttatgtttat cggcactttg catcggccgc gctcccgatt   6592
ccggaagtgc ttgacattgg ggaattcagc gagagcctga cctattgcat ctcccgccgt   6652
gcacagggtg tcacgttgca agacctgcct gaaaccgaac tgcccgctgt tctgcagccg   6712
gtcgcggagg ccatggatgc gatcgctgcg gccgatctta gccagacgag cgggttcggc   6772
ccattcggac cgcaaggaat cggtcaatac actacatggc gtgatttcat atgcgcgatt   6832
gctgatcccc atgtgtatca ctggcaaact gtgatggacg acaccgtcag tgcgtccgtc   6892
gcgcaggctc tcgatgagct gatgctttgg gccgaggact gccccgaagt ccggcacctc   6952
gtgcacgcgg atttcggctc caacaatgtc ctgacggaca atggccgcat aacagcggtc   7012
attgactgga gcgaggcgat gttcggggat tcccaatacg aggtcgccaa catcttcttc   7072
tggaggccgt ggttggcttg tatggagcag cagacgcgct acttcgagcg gaggcatccg   7132
gagcttgcag gatcgccgcg gctccgggcg tatatgctcc gcattggtct tgaccaactc   7192
tatcagagct tggttgacgg caatttcgat gatgcagctt gggcgcaggg tcgatgcgac   7252
gcaatcgtcc gatccggagc cgggactgtc gggcgtacac aaatcgcccg cagaagcgcg   7312
gccgtctgga ccgatggctg tgtagaagta ctcgccgata gtggaaaccg acgccccagc   7372
actcgtccgg atcgggagat gggggaggct aactgaaaca cggaaggaga caataccgga   7432
aggaacccgc gctatgacgg caataaaaag acagaataaa acgcacgggt gttgggtcgt   7492
ttgttcataa acgcggggtt cggtcccagg gctggcactc tgtcgatacc ccaccgagac   7552
```

```
cccattgggg ccaatacgcc cgcgtttctt ccttttcccc accccacccc ccaagttcgg   7612
gtgaaggccc agggctcgca gccaacgtcg gggcggcagg ccctgccata gccactggcc   7672
ccgtgggtta gggacggggt cccccatggg gaatggttta tggttcgtgg gggttattat   7732
tttgggcgtt gcgtggggtc aggtccacga ctggactgag cagacagacc catggttttt   7792
ggatggcctg ggcatggacc gcatgtactg gcgcgacacg aacaccgggc gtctgtggct   7852
gccaaacacc cccgaccccc aaaaaccacc gcgcggattt ctggcgtgcc aagctgggta   7912
ccctctagag cgaattaatt cactggccgt cgttttacaa cgtcgtgact gggaaaaccc   7972
tggcgttacc caacttaatc gccttgcagc acatcccect ttcgccagct ggcataatag   8032
cgaagaggcc cgcaccgatc gcccttccca acagttgcgc agcctgaatg gcgaatggcg   8092
cctgatgcgg tattttctcc ttacgcatct gtgcggtatt tcacaccgca tatggtgcac   8152
tctcagtaca atctgctctg atgccgcata gttaagccag ccccgacacc cgccaacacc   8212
cgctgacgcg ccctgacggg cttgtctgct cccggcatcc gcttacagac aagctgtgac   8272
cgtctccggg agctgcatgt gtcagaggtt ttcaccgtca tcaccgaaac gcgcgagacg   8332
aaagggggggg taccagcttc gtagctagaa catcatgttc tgggatatca gcttcgtagc  8392
tagaacatca tgttctggta cccccctcgt gatacgccta tttttatagg ttaatgtcat   8452
gataataatg gtttcttaga cgtcaggtgg cacttttcgg ggaaatgtgc gcggaacccc   8512
tatttgttta tttttctaaa tacattcaaa tatgtatccg ctcatgagac aataaccctg   8572
ataaatgctt caataatatt gaaaaaggaa gagtatgagt attcaacatt tccgtgtcgc   8632
ccttattccc ttttttgcgg cattttgcct tcctgttttt gctcacccag aaacgctggt   8692
gaaagtaaaa gatgctgaag atcagttggg tgcacgagtg ggttacatcg aactggatct   8752
caacagcggt aagatccttg agagttttcg ccccgaagaa cgttttccaa tgatgagcac   8812
ttttaaagtt ctgctatgtg gcgcggtatt atcccgtatt gacgccgggc aagagcaact   8872
cggtcgccgc atacactatt ctcagaatga cttggttgag tactcaccag tcacagaaaa   8932
gcatcttacg gatggcatga cagtaagaga attatgcagt gctgccataa ccatgagtga   8992
taacactgcg gccaacttac ttctgacaac gatcggagga ccgaaggagc taaccgcttt   9052
tttgcacaac atgggggatc atgtaactcg ccttgatcgt tgggaaccgg agctgaatga   9112
agccatacca aacgacgagc gtgacaccac gatgcctgta gcaatggcaa caacgttgcg   9172
caaactatta actggcgaac tacttactct agcttcccgg caacaattaa tagactggat   9232
ggaggcggat aaagttgcag gaccacttct gcgctcggcc cttccggctg gctggtttat   9292
tgctgataaa tctggagccg gtgagcgtgg gtctcgcggt atcattgcag cactggggcc   9352
agatggtaag ccctcccgta tcgtagttat ctacacgacg gggagtcagg caactatgga   9412
tgaacgaaat agacagatcg ctgagatagg tgcctcactg attaagcatt ggtaactgtc   9472
agaccaagtt tactcatata tactttagat tgatttaaaa cttcattttt aatttaaaag   9532
gatctaggtg aagatccttt ttgataatct catgaccaaa atcccttaac gtgagttttc   9592
gttccactga gcgtcagacc ccgtagaaaa gatcaaagga tcttcttgag atcctttttt   9652
tctgcgcgta atctgctgct tgcaaacaaa aaaaccaccg ctaccagcgg tggtttgttt   9712
gccggatcaa gagctaccaa ctctttttcc gaaggtaact ggcttcagca gagcgcagat   9772
accaaatact gttcttctag tgtagccgta gttaggccac cacttcaaga actctgtagc   9832
accgcctaca tacctcgctc tgctaatcct gttaccagtg gctgctgcca gtggcgataa   9892
```

```
gtcgtgtctt accgggttgg actcaagacg atagttaccg gataaggcgc agcggtcggg   9952

ctgaacgggg ggttcgtgca cacagcccag cttggagcga acgacctaca ccgaactgag  10012

atacctacag cgtgagctat gagaaagcgc cacgcttccc gaagggagaa aggcggacag  10072

gtatccggta agcggcaggg tcggaacagg agagcgcacg agggagcttc cagggggaaa  10132

cgcctggtat ctttatagtc ctgtcgggtt tcgccacctc tgacttgagc gtcgattttt  10192

gtgatgctcg tcaggggggc ggagcctatg gaaaaacgcc agcaacgcgg cctttttacg  10252

gttcctggcc ttttgctggc cttttgctca catgttcttt cctgcgttat cccctgattc  10312

tgtggataac cgtattaccg cctttgagtg agctgatacc gctcgccgca gccgaacgac  10372

cgagcgcagc gagtcagtga gcgaggaagc ggaagagcgc ccaatacgca aaccgcctct  10432

ccccgcgcgt tggccgattc attaatgcag ctggcacgac aggtttcccg actggaaagc  10492

gggcagtgag cgcaacgcaa ttaatgtgag ttagctcact cattaggcac cccaggcttt  10552

acactttatg cttccggctc gtatgttgtg tggaattgtg agcggataac aatttcacac  10612

aggaaacagc tatgaccatg attacgccaa gctctctaga gctctagagc tctagagctc  10672

tagagagctt gcatgcctgc aggtcg                                       10698
```

```
<210> SEQ ID NO 6
<211> LENGTH: 1459
<212> TYPE: PRT
<213> ORGANISM: Artificial Sequence
<220> FEATURE:
<223> OTHER INFORMATION: Description of Artificial Sequence:
      pTGF8-2hyg-s

<400> SEQUENCE: 6

Met Gln Ile Glu Leu Ser Thr Cys Phe Phe Leu Cys Leu Leu Arg Phe
                -15                 -10                 -5

Cys Phe Ser Ala Thr Arg Arg Tyr Tyr Leu Gly Ala Val Glu Leu Ser
        -1  1               5                   10

Trp Asp Tyr Met Gln Ser Asp Leu Gly Glu Leu Pro Val Asp Ala Arg
    15                  20                  25

Phe Pro Pro Arg Val Pro Lys Ser Phe Pro Phe Asn Thr Ser Val Val
30                  35                  40                  45

Tyr Lys Lys Thr Leu Phe Val Glu Phe Thr Asp His Leu Phe Asn Ile
                50                  55                  60

Ala Lys Pro Arg Pro Pro Trp Met Gly Leu Leu Gly Pro Thr Ile Gln
            65                  70                  75

Ala Glu Val Tyr Asp Thr Val Val Ile Thr Leu Lys Asn Met Ala Ser
        80                  85                  90

His Pro Val Ser Leu His Ala Val Gly Val Ser Tyr Trp Lys Ala Ser
    95                  100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
            145                 150                 155

Tyr Leu Ser His Val Asp Leu Val Lys Asp Leu Asn Ser Gly Leu Ile
        160                 165                 170

Gly Ala Leu Leu Val Cys Arg Glu Gly Ser Leu Ala Lys Glu Lys Thr
    175                 180                 185

Gln Thr Leu His Lys Phe Ile Leu Leu Phe Ala Val Phe Asp Glu Gly
```

-continued

```
190                 195                 200                 205

Lys Ser Trp His Ser Glu Thr Lys Asn Ser Leu Met Gln Asp Arg Asp
                210                 215                 220

Ala Ala Ser Ala Arg Ala Trp Pro Lys Met His Thr Val Asn Gly Tyr
            225                 230                 235

Val Asn Arg Ser Leu Pro Gly Leu Ile Gly Cys His Arg Lys Ser Val
        240                 245                 250

Tyr Trp His Val Ile Gly Met Gly Thr Thr Pro Glu Val His Ser Ile
    255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
                290                 295                 300

Asp Leu Gly Gln Phe Leu Leu Phe Cys His Ile Ser Ser His Gln His
            305                 310                 315

Asp Gly Met Glu Ala Tyr Val Lys Val Asp Ser Cys Pro Glu Glu Pro
        320                 325                 330

Gln Leu Arg Met Lys Asn Asn Glu Glu Ala Glu Asp Tyr Asp Asp Asp
    335                 340                 345

Leu Thr Asp Ser Glu Met Asp Val Val Arg Phe Asp Asp Asp Asn Ser
350                 355                 360                 365

Pro Ser Phe Ile Gln Ile Arg Ser Val Ala Lys Lys His Pro Lys Thr
                370                 375                 380

Trp Val His Tyr Ile Ala Ala Glu Glu Glu Asp Trp Asp Tyr Ala Pro
            385                 390                 395

Leu Val Leu Ala Pro Asp Asp Arg Ser Tyr Lys Ser Gln Tyr Leu Asn
        400                 405                 410

Asn Gly Pro Gln Arg Ile Gly Arg Lys Tyr Lys Lys Val Arg Phe Met
    415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Gln Ala Ser Arg Pro Tyr Asn Ile Tyr Pro
            465                 470                 475

His Gly Ile Thr Asp Val Arg Pro Leu Tyr Ser Arg Arg Leu Pro Lys
        480                 485                 490

Gly Val Lys His Leu Lys Asp Phe Pro Ile Leu Pro Gly Glu Ile Phe
    495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
                530                 535                 540

Asp Leu Ala Ser Gly Leu Ile Gly Pro Leu Leu Ile Cys Tyr Lys Glu
            545                 550                 555

Ser Val Asp Gln Arg Gly Asn Gln Ile Met Ser Asp Lys Arg Asn Val
        560                 565                 570

Ile Leu Phe Ser Val Phe Asp Glu Asn Arg Ser Trp Tyr Leu Thr Glu
    575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620
```

```
Phe Asp Ser Leu Gln Leu Ser Val Cys Leu His Glu Val Ala Tyr Trp
            625                 630                 635

Tyr Ile Leu Ser Ile Gly Ala Gln Thr Asp Phe Leu Ser Val Phe Phe
        640                 645                 650

Ser Gly Tyr Thr Phe Lys His Lys Met Val Tyr Glu Asp Thr Leu Thr
    655                 660                 665

Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
                690                 695                 700

Met Thr Ala Leu Leu Lys Val Ser Ser Cys Asp Lys Asn Thr Gly Asp
            705                 710                 715

Tyr Tyr Glu Asp Ser Tyr Glu Asp Ile Ser Ala Tyr Leu Leu Ser Lys
        720                 725                 730

Asn Asn Ala Ile Glu Pro Arg Ser Phe Ser Gln Asn Ser Arg His Gln
    735                 740                 745

Ala Tyr Arg Tyr Arg Arg Gly Glu Ile Thr Arg Thr Thr Leu Gln Ser
750                 755                 760                 765

Asp Gln Glu Glu Ile Asp Tyr Asp Asp Thr Ile Ser Val Glu Met Lys
                770                 775                 780

Lys Glu Asp Phe Asp Ile Tyr Asp Glu Asp Glu Asn Gln Ser Pro Arg
            785                 790                 795

Ser Phe Gln Lys Lys Thr Arg His Tyr Phe Ile Ala Ala Val Glu Arg
        800                 805                 810

Leu Trp Asp Tyr Gly Met Ser Ser Ser Pro His Val Leu Arg Asn Arg
    815                 820                 825

Ala Gln Ser Gly Ser Val Pro Gln Phe Lys Lys Val Val Phe Gln Glu
830                 835                 840                 845

Phe Thr Asp Gly Ser Phe Thr Gln Pro Leu Tyr Arg Gly Glu Leu Asn
                850                 855                 860

Glu His Leu Gly Leu Leu Gly Pro Tyr Ile Arg Ala Glu Val Glu Asp
            865                 870                 875

Asn Ile Met Val Thr Phe Arg Asn Gln Ala Ser Arg Pro Tyr Ser Phe
        880                 885                 890

Tyr Ser Ser Leu Ile Ser Tyr Glu Glu Asp Gln Arg Gln Gly Ala Glu
    895                 900                 905

Pro Arg Lys Asn Phe Val Lys Pro Asn Glu Thr Lys Thr Tyr Phe Trp
910                 915                 920                 925

Lys Val Gln His His Met Ala Pro Thr Lys Asp Glu Phe Asp Cys Lys
                930                 935                 940

Ala Trp Ala Tyr Phe Ser Asp Val Asp Leu Glu Lys Asp Val His Ser
            945                 950                 955

Gly Leu Ile Gly Pro Leu Leu Val Cys His Thr Asn Thr Leu Asn Pro
        960                 965                 970

Ala His Gly Arg Gln Val Thr Val Gln Glu Phe Ala Leu Phe Phe Thr
    975                 980                 985

Ile Phe Asp Glu Thr Lys Ser Trp Tyr Phe Thr  Glu Asn Met Glu Arg
990                 995                 1000                1005

Asn Cys Arg Ala Pro  Cys Asn Ile Gln Met  Glu Asp Pro Thr Phe
                1010                1015                1020

Lys Glu Asn Tyr Arg  Phe His Ala Ile Asn  Gly Tyr Ile Met Asp
                1025                1030                1035
```

-continued

```
Thr Leu Pro Gly Leu  Val Met Ala Gln Asp  Gln Arg Ile Arg Trp
                1040                 1045                 1050

Tyr Leu Leu Ser Met  Gly Ser Asn Glu Asn  Ile His Ser Ile His
                1055                 1060                 1065

Phe Ser Gly His Val  Phe Thr Val Arg Lys  Lys Glu Glu Tyr Lys
                1070                 1075                 1080

Met Ala Leu Tyr Asn  Leu Tyr Pro Gly Val  Phe Glu Thr Val Glu
                1085                 1090                 1095

Met Leu Pro Ser Lys  Ala Gly Ile Trp Arg  Val Glu Cys Leu Ile
                1100                 1105                 1110

Gly Glu His Leu His  Ala Gly Met Ser Thr  Leu Phe Leu Val Tyr
                1115                 1120                 1125

Ser Asn Lys Cys Gln  Thr Pro Leu Gly Met  Ala Ser Gly His Ile
                1130                 1135                 1140

Arg Asp Phe Gln Ile  Thr Ala Ser Gly Gln  Tyr Gly Gln Trp Ala
                1145                 1150                 1155

Pro Lys Leu Ala Arg  Leu His Tyr Ser Gly  Ser Ile Asn Ala Trp
                1160                 1165                 1170

Ser Thr Lys Glu Pro  Phe Ser Trp Ile Lys  Val Asp Leu Leu Ala
                1175                 1180                 1185

Pro Met Ile Ile His  Gly Ile Lys Thr Gln  Gly Ala Arg Gln Lys
                1190                 1195                 1200

Phe Ser Ser Leu Tyr  Ile Ser Gln Phe Ile  Ile Met Tyr Ser Leu
                1205                 1210                 1215

Asp Gly Lys Lys Trp  Gln Thr Tyr Arg Gly  Asn Ser Thr Gly Thr
                1220                 1225                 1230

Leu Met Val Phe Phe  Gly Asn Val Asp Ser  Ser Gly Ile Lys His
                1235                 1240                 1245

Asn Ile Phe Asn Pro  Pro Ile Ile Ala Arg  Tyr Ile Arg Leu His
                1250                 1255                 1260

Pro Thr His Tyr Ser  Ile Arg Ser Thr Leu  Arg Met Glu Leu Met
                1265                 1270                 1275

Gly Cys Asp Leu Asn  Ser Cys Ser Met Pro  Leu Gly Met Glu Ser
                1280                 1285                 1290

Lys Ala Ile Ser Asp  Ala Gln Ile Thr Ala  Ser Ser Tyr Phe Thr
                1295                 1300                 1305

Asn Met Phe Ala Thr  Trp Ser Pro Ser Lys  Ala Arg Leu His Leu
                1310                 1315                 1320

Gln Gly Arg Ser Asn  Ala Trp Arg Pro Gln  Val Asn Asn Pro Lys
                1325                 1330                 1335

Glu Trp Leu Gln Val  Asp Phe Gln Lys Thr  Met Lys Val Thr Gly
                1340                 1345                 1350

Val Thr Thr Gln Gly  Val Lys Ser Leu Leu  Thr Ser Met Tyr Val
                1355                 1360                 1365

Lys Glu Phe Leu Ile  Ser Ser Ser Gln Asp  Gly His Gln Trp Thr
                1370                 1375                 1380

Leu Phe Phe Gln Asn  Gly Lys Val Lys Val  Phe Gln Gly Asn Gln
                1385                 1390                 1395

Asp Ser Phe Thr Pro  Val Val Asn Ser Leu  Asp Pro Pro Leu Leu
                1400                 1405                 1410

Thr Arg Tyr Leu Arg  Ile His Pro Gln Ser  Trp Val His Gln Ile
                1415                 1420                 1425

Ala Leu Arg Met Glu  Val Leu Gly Cys Glu  Ala Gln Asp Leu Tyr
```

1430 1435 1440

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: B-domain linker peptide

<400> SEQUENCE: 7

Ser Phe Ser Gln Asn Ser Arg His
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: B-domain linker peptide

<400> SEQUENCE: 8

Gln Ala Tyr Arg Tyr Arg Arg Gly
1 5

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: B-domain linker peptide

<400> SEQUENCE: 9

Ser Phe Ser Gln Asn Ser Arg His Gln Ala Tyr Arg Tyr Arg Arg Gly
1 5 10 15

<210> SEQ ID NO 10
<211> LENGTH: 5753
<212> TYPE: DNA
<213> ORGANISM: Artificial Sequence
<220> FEATURE:
<223> OTHER INFORMATION: Description of Artificial Sequence: pTGFG36
<220> FEATURE:
<221> NAME/KEY: CDS
<222> LOCATION: (689)..(2071)

<400> SEQUENCE: 10
cgcgttgaca ttgattattg actagttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatggtga tgcggttttg gcagtacatc aatgggcgtg 420
gatagcggtt tgactcacgg ggatttccaa gtctccaccc cattgacgtc aatgggagtt 480
tgttttggca ccaaaatcaa cgggactttc caaaatgtcg taacaactcc gccccattga 540
cgcaaatggg cggtaggcgt gtacggtggg aggtctatat aagcagagct ctctggctaa 600
ctagagaacc cactgcttac tggcttatcg aaattaatac gactcactat agggagaccc 660

-continued

```
aagcttgcat gccaattccg caaaggtt atg cag cgc gtg aac atg atc atg       712
                               Met Gln Arg Val Asn Met Ile Met
                               1               5

gca gaa tca cca ggc ctc atc acc atc tgc ctt tta gga tat cta ctc      760
Ala Glu Ser Pro Gly Leu Ile Thr Ile Cys Leu Leu Gly Tyr Leu Leu
    10                  15                  20

agt gct gaa tgt aca gtt ttt ctt gat cat gaa aac gcc aac aaa att      808
Ser Ala Glu Cys Thr Val Phe Leu Asp His Glu Asn Ala Asn Lys Ile
25                  30                  35                  40

ctg aat cgg cca aag agg tat aat tca ggt aaa ttg gaa gag ttt gtt      856
Leu Asn Arg Pro Lys Arg Tyr Asn Ser Gly Lys Leu Glu Glu Phe Val
                45                  50                  55

caa ggg aac ctt gag aga gaa tgt atg gaa gaa aag tgt agt ttt gaa      904
Gln Gly Asn Leu Glu Arg Glu Cys Met Glu Glu Lys Cys Ser Phe Glu
            60                  65                  70

gaa gca cga gaa gtt ttt gaa aac act gaa aga aca act gaa ttt tgg      952
Glu Ala Arg Glu Val Phe Glu Asn Thr Glu Arg Thr Thr Glu Phe Trp
        75                  80                  85

aag cag tat gtt gat gga gat cag tgt gag tcc aat cca tgt tta aat     1000
Lys Gln Tyr Val Asp Gly Asp Gln Cys Glu Ser Asn Pro Cys Leu Asn
    90                  95                  100

ggc ggc agt tgc aag gat gac att aat tcc tat gaa tgt tgg tgt ccc     1048
Gly Gly Ser Cys Lys Asp Asp Ile Asn Ser Tyr Glu Cys Trp Cys Pro
105                 110                 115                 120

ttt gga ttt gaa gga aag aac tgt gaa tta gat gta aca tgt aac att     1096
Phe Gly Phe Glu Gly Lys Asn Cys Glu Leu Asp Val Thr Cys Asn Ile
                125                 130                 135

aag aat ggc aga tgc gag cag ttt tgt aaa aat agt gct gat aac aag     1144
Lys Asn Gly Arg Cys Glu Gln Phe Cys Lys Asn Ser Ala Asp Asn Lys
            140                 145                 150

gtg gtt tgc tcc tgt act gag gga tat cga ctt gca gaa aac cag aag     1192
Val Val Cys Ser Cys Thr Glu Gly Tyr Arg Leu Ala Glu Asn Gln Lys
        155                 160                 165

tcc tgt gaa cca gca gtg cca ttt cca tgt gga aga gtt tct gtt tca     1240
Ser Cys Glu Pro Ala Val Pro Phe Pro Cys Gly Arg Val Ser Val Ser
    170                 175                 180

caa act tct aag ctc acc cgt gct gag act gtt ttt cct gat gtg gac     1288
Gln Thr Ser Lys Leu Thr Arg Ala Glu Thr Val Phe Pro Asp Val Asp
185                 190                 195                 200

tat gta aat tct act gaa gct gaa acc att ttg gat aac atc act caa     1336
Tyr Val Asn Ser Thr Glu Ala Glu Thr Ile Leu Asp Asn Ile Thr Gln
                205                 210                 215

agc acc caa tca ttt aat gac ttc act cgg gtt gtt ggt gga gaa gat     1384
Ser Thr Gln Ser Phe Asn Asp Phe Thr Arg Val Val Gly Gly Glu Asp
            220                 225                 230

gcc aaa cca ggt caa ttc cct tgg cag gtt gtt ttg aat ggt aaa gtt     1432
Ala Lys Pro Gly Gln Phe Pro Trp Gln Val Val Leu Asn Gly Lys Val
        235                 240                 245

gat gca ttc tgt gga ggc tct atc gtt aat gaa aaa tgg att gta act     1480
Asp Ala Phe Cys Gly Gly Ser Ile Val Asn Glu Lys Trp Ile Val Thr
    250                 255                 260

gct gcc cac tgt gtt gaa act ggt gtt aaa att aca gtt gtc gca ggt     1528
Ala Ala His Cys Val Glu Thr Gly Val Lys Ile Thr Val Val Ala Gly
265                 270                 275                 280

gaa cat aat att gag gag aca gaa cat aca gag caa aag cga aat gtg     1576
Glu His Asn Ile Glu Glu Thr Glu His Thr Glu Gln Lys Arg Asn Val
                285                 290                 295

att cga att att cct cac cac aac tac aat gca gct att aat aag tac     1624
Ile Arg Ile Ile Pro His His Asn Tyr Asn Ala Ala Ile Asn Lys Tyr
            300                 305                 310
```

-continued

```
aac cat gac att gcc ctt ctg gaa ctg gac gaa ccc tta gtg cta aac     1672
Asn His Asp Ile Ala Leu Leu Glu Leu Asp Glu Pro Leu Val Leu Asn
        315                 320                 325

agc tac gtt aca cct att tgc att gct gac aag gaa tac acg aac atc     1720
Ser Tyr Val Thr Pro Ile Cys Ile Ala Asp Lys Glu Tyr Thr Asn Ile
    330                 335                 340

ttc ctc aaa ttt gga tct ggc tat gta agt ggc tgg gga aga gtc ttc     1768
Phe Leu Lys Phe Gly Ser Gly Tyr Val Ser Gly Trp Gly Arg Val Phe
345                 350                 355                 360

cac aaa ggg aga tca gct tta gtt ctt cag tac ctt aga gtt cca ctt     1816
His Lys Gly Arg Ser Ala Leu Val Leu Gln Tyr Leu Arg Val Pro Leu
                365                 370                 375

gtt gac cga gcc aca tgt ctt cga tct aca aag ttc acc atc tat aac     1864
Val Asp Arg Ala Thr Cys Leu Arg Ser Thr Lys Phe Thr Ile Tyr Asn
            380                 385                 390

aac atg ttc tgt gct ggc ttc cat gaa gga ggt aga gat tca tgt caa     1912
Asn Met Phe Cys Ala Gly Phe His Glu Gly Gly Arg Asp Ser Cys Gln
        395                 400                 405

gga gat agt ggg gga ccc cat gtt act gaa gtg gaa ggg acc agt ttc     1960
Gly Asp Ser Gly Gly Pro His Val Thr Glu Val Glu Gly Thr Ser Phe
    410                 415                 420

tta act gga att att agc tgg ggt gaa gag tgt gca atg aaa ggc aaa     2008
Leu Thr Gly Ile Ile Ser Trp Gly Glu Glu Cys Ala Met Lys Gly Lys
425                 430                 435                 440

tat gga ata tat acc aag gta tcc cgg tat gtc aac tgg att aag gaa     2056
Tyr Gly Ile Tyr Thr Lys Val Ser Arg Tyr Val Asn Trp Ile Lys Glu
                445                 450                 455

aaa aca aag ctc act taatgggatc ggtcgagcgg ccgcgactct actagaggat     2111
Lys Thr Lys Leu Thr
            460

ctttgtgaag gaaccttact tctgtggtgt gacataattg gacaaactac ctacagagat   2171

ttaaagctct aaggtaaata taaaattttt aagtgtataa tgtgttaaac tactgattct   2231

aattgtttgt gtattttaga ttccaaccta tggaactgat gaatgggagc agtggtggaa   2291

tgcctttaat gaggaaaacc tgttttgctc agaagaaatg ccatctagtg atgatgaggc   2351

tactgctgac tctcaacatt ctactcctcc aaaaaagaag agaaaggtag aagaccccaa   2411

ggactttcct tcagaattgc taagtttttt gagtcatgct gtgtttagta atagaactct   2471

tgcttgcttt gctatttaca ccacaaagga aaaagctgca ctgctataca agaaaattat   2531

ggaaaaatat tctgtaacct ttataagtag gcataacagt tataatcata acatactgtt   2591

ttttcttact ccacacaggc atagagtgtc tgctattaat aactatgctc aaaaattgtg   2651

tacctttagc tttttaattt gtaaaggggt taataaggaa tatttgatgt atagtgcctt   2711

gactagagat cataatcagc cataccacat ttgtagaggt tttacttgct ttaaaaaacc   2771

tcccacacct cccccctgaac ctgaaacata aaatgaatgc aattgttgtt gttaacttgt  2831

ttattgcagc ttataatggt tacaaataaa gcaatagcat cacaaatttc acaaataaag   2891

catttttttc actgcattct agttgtggtt tgtccaaact catcaatgta tcttatcatg   2951

tctggatccc cgggtaccct ctagagcgaa ttaattcact ggccgtcgtt ttacaacgtc   3011

gtgactggga aaaccctggc gttacccaac ttaatcgcct tgcagcacat ccccctttcg   3071

ccagctggcg taatagcgaa gaggcccgca ccgatcgccc ttcccaacag ttgcgcagcc   3131

tgaatggcga atggcgcctg atgcggtatt ttctccttac gcatctgtgc ggtatttcac   3191

accgcatatg gtgcactctc agtacaatct gctctgatgc cgcatagtta agccagcccc   3251
```

-continued

```
gacacccgcc aacacccgct gacgcgccct gacgggcttg tctgctcccg gcatccgctt   3311
acagacaagc tgtgaccgtc tccgggagct gcatgtgtca gaggttttca ccgtcatcac   3371
cgaaacgcgc gagacgaaag ggggggtacc agcttcgtag ctagaacatc atgttctggg   3431
atatcagctt cgtagctaga acatcatgtt ctggtacccc cctcgtgata cgcctatttt   3491
tataggttaa tgtcatgata ataatggttt cttagacgtc aggtggcact tttcggggaa   3551
atgtgcgcgg aacccctatt tgtttatttt tctaaataca ttcaaatatg tatccgctca   3611
tgagacaata accctgataa atgcttcaat aatattgaaa aaggaagagt atgagtattc   3671
aacatttccg tgtcgccctt attccctttt ttgcggcatt ttgccttcct gtttttgctc   3731
acccagaaac gctggtgaaa gtaaaagatg ctgaagatca gttgggtgca cgagtgggtt   3791
acatcgaact ggatctcaac agcggtaaga tccttgagag ttttcgcccc gaagaacgtt   3851
ttccaatgat gagcactttt aaagttctgc tatgtggcgc ggtattatcc cgtattgacg   3911
ccgggcaaga gcaactcggt cgccgcatac actattctca gaatgacttg gttgagtact   3971
caccagtcac agaaaagcat cttacggatg gcatgacagt aagagaatta tgcagtgctg   4031
ccataaccat gagtgataac actgcggcca acttacttct gacaacgatc ggaggaccga   4091
aggagctaac cgcttttttg cacaacatgg gggatcatgt aactcgcctt gatcgttggg   4151
aaccggagct gaatgaagcc ataccaaacg acgagcgtga caccacgatg cctgtagcaa   4211
tggcaacaac gttgcgcaaa ctattaactg gcgaactact tactctagct tcccggcaac   4271
aattaataga ctggatggag gcggataaag ttgcaggacc acttctgcgc tcggcccttc   4331
cggctggctg gtttattgct gataaatctg gagccggtga gcgtgggtct cgcggtatca   4391
ttgcagcact ggggccagat ggtaagccct cccgtatcgt agttatctac acgacgggga   4451
gtcaggcaac tatggatgaa cgaaatagac agatcgctga gataggtgcc tcactgatta   4511
agcattggta actgtcagac caagtttact catatatact ttagattgat ttaaaacttc   4571
atttttaatt taaaaggatc taggtgaaga tcctttttga taatctcatg accaaaatcc   4631
cttaacgtga gttttcgttc cactgagcgt cagaccccgt agaaaagatc aaaggatctt   4691
cttgagatcc tttttttctg cgcgtaatct gctgcttgca aacaaaaaaa ccaccgctac   4751
cagcggtggt ttgtttgccg gatcaagagc taccaactct ttttccgaag gtaactggct   4811
tcagcagagc gcagatacca aatactgttc ttctagtgta gccgtagtta ggccaccact   4871
tcaagaactc tgtagcaccg cctacatacc tcgctctgct aatcctgtta ccagtggctg   4931
ctgccagtgg cgataagtcg tgtcttaccg ggttggactc aagacgatag ttaccggata   4991
aggcgcagcg gtcgggctga acggggggtt cgtgcacaca gcccagcttg gagcgaacga   5051
cctacaccga actgagatac ctacagcgtg agctatgaga aagcgccacg cttcccgaag   5111
ggagaaaggc ggacaggtat ccggtaagcg gcagggtcgg aacaggagag cgcacgaggg   5171
agcttccagg gggaaacgcc tggtatcttt atagtcctgt cgggtttcgc cacctctgac   5231
ttgagcgtcg atttttgtga tgctcgtcag gggggcggag cctatggaaa aacgccagca   5291
acgcggcctt tttacggttc ctggcctttt gctggccttt tgctcacatg ttctttcctg   5351
cgttatcccc tgattctgtg gataaccgta ttaccgcctt tgagtgagct gataccgctc   5411
gccgcagccg aacgaccgag cgcagcgagt cagtgagcga ggaagcggaa gagcgcccaa   5471
tacgcaaacc gcctctcccc gcgcgttggc cgattcatta atgcagctgg cacgacaggt   5531
ttcccgactg gaaagcgggc agtgagcgca acgcaattaa tgtgagttag ctcactcatt   5591
aggcacccca ggctttacac tttatgcttc cggctcgtat gttgtgtgga attgtgagcg   5651
```

```
gataacaatt tcacacagga aacagctatg accatgatta cgccaagctc tctagagctc   5711

tagagctcta gagctctaga gagcttgcat gcctgcaggt cg                      5753


<210> SEQ ID NO 11
<211> LENGTH: 461
<212> TYPE: PRT
<213> ORGANISM: Artificial Sequence
<220> FEATURE:
<223> OTHER INFORMATION: Description of Artificial Sequence: pTGFG36

<400> SEQUENCE: 11

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
```

```
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460
```

METHOD FOR IMPROVED ISOLATION OF RECOMBINANTLY PRODUCED PROTEINS

CROSS-REFERENCE TO RELATED PATENT APPLICATIONS

This application is a continuation of U.S. application Ser. No. 11/887,677, filed Feb. 4, 2008 (U.S. Pat. No. 9,388,402), which is a national phase application of International Application No. PCT/EP2006/061148, which was filed Mar. 29, 2006, and which claims the benefit of the filing date of European Patent Application 05102475.0, which was filed on Mar. 29, 2005. The content of these earlier filed applications is hereby incorporated by reference in its entirety.

SEQUENCE LISTING

The present application contains a Sequence Listing that has been submitted in ASCII format via EFS-Web on Oct. 21, 2016, containing the file name 37693.0001U2_Revised_SL which is 159,744 bytes in size, created on Oct. 20, 2016, and is hereby incorporated by reference in its entirety.

FIELD OF INVENTION

The present invention provides a method for increasing the yield of a protein produced by cultivating eukaryotic cells under serum-free conditions and adding an ionic substance to the culture medium prior to harvest of the protein. Suitable ionic substances are the salts of the Hofmeister series, amino acids and peptone.

BACKGROUND

Most proteins for medical, cosmetic or industrial applications are produced as recombinant proteins in cultivated microbial or eukaryotic cells. For that a gene encoding the protein of interest is inserted into the organism/cells of choice, the organism/cells carrying said gene is cultivated in a medium comprising all essential nutrients to allow for growth and expression of said gene, resulting in the production of the protein of interest. If the protein of interest is secreted by the cells into the medium, the cells and the medium are separated from each other using centrifugation or filter membranes. The recovered cell-free protein containing medium is then further processed through purification steps to remove host cell proteins, DNA and other contaminants.

In general, there are two different production alternatives for the harvest of recombinantly produced proteins, continuous and batch harvest. When applying continuous harvest, the cultivation media is continuously slowly removed from the cell cultivation vessel during the production phase and fresh medium is simultaneously added. Continuous harvest is chosen when the cells are slowly growing and/or the process facilitates a high cell concentration or if the product must be removed fast from the cultivation to protect it from degradation. Batch harvesting is performed at one defined point, where the cells are removed in one step and thereafter they are normally discarded. It is technically easier to run a batch harvesting compared to a continuous one, but the optimal harvest procedure must be determined in each specific case depending on product and cell type. In some cases, where the product is not secreted, the cell membrane must be destroyed in order to recover the product. It is, however, preferred to keep the cell membrane intact, if possible, in order to avoid contamination of the product with DNA and host cell proteins. Continuous harvest normally gives a higher total productivity compared to batch harvest as the cells can produce for a longer period of time. To minimize the contamination of the product, it is preferable to choose the harvest method which releases the lowest amount of DNA and host cell proteins. In a special mode of batch harvesting, where the cell membranes are kept intact, a considerable improvement in productivity can be achieved, if the cell can be reused. This cyclic batch harvest method is particularly applicable for slowly growing (valuable) production cells.

To obtain high yields of the protein, it is important to optimize the process to achieve a high productivity of the product. The main efforts so far to improve the yield of a recombinantly produced protein have focused on the molecular insert (vectors, enhancers, promoters, etc.) to optimize the expression system, the conditions under which the cells are cultured and the actual purification steps. For example stabilizers such as protease inhibitors are added into the medium and the purification procedures are set up in the presence of protease inhibitors to reduce the loss of the product protein. However, it is often very difficult to find a protease inhibitor which can be used during cultivation, as protease inhibitors also tend to inhibit cell growth and protein production. As soon as the cells have been removed, it is easier to find a suitable protease inhibitor. This is described, for example, in U.S. Pat. No. 5,831,026, where EDTA is added to inhibit metallo-proteases. Moreover, it is to be noted that any stabilizing agents added need to be removed again at some point of the production process to obtain a pure recombinant protein product. Thus there is still a need to improve the existing methods of recombinant protein production to gain higher yields of the recombinant protein.

Another problem encountered especially when utilizing mammalian cells as production hosts is that the secretion of the produced proteins is rather low. It is apparent that secreted products often adhere to the cell membrane and that this has an influence on the product release. In some cases, the retardation can be inhibited by physiological conditions (i.e. the environment in which the cells are cultivated), whereas in some cases non-physiological conditions must be applied. The total disruption of cells should be avoided, if possible, as this releases DNA and host cell proteins, which need to be removed later in the purification process.

It is known in the art that an increase in salt concentrations (for instance, NaCl), accompanied by the addition of detergent and/or by adjusting a specific pH can in some cases release the bound proteins. For instance, K. Berman et al., Mol. Cell Biol. Res. Com. 4, 337-344 (2001) emphasizes that in the production of p38 homologs in HEK293 cells, the cells could be stimulated with sorbitol or 0.7 M NaCl for 10 minutes prior to harvest. A. B. Vaandrager et al., J. Biol. Chem., Vol. 271, No. 12, pp. 7025-7029 (1996) discloses that the cultivation of HEK293 cells expressing rat cGKII resulted in recovery of 90-95% of the expressed cGKII, and that the enzyme could be released from membranes by a combination of detergent (1% Triton® X-100) and high salt (0.5 M NaCl) but not by detergent or high salt alone. A. Denys et al., Biochem J., 336, 689-697 (1998) disclose that a protein was released from human T-lymphocyte cells using a washing procedure including 0.6 M NaCl. However, not all (70%) protein could be released even if NaCl concentration was raised to 1 M. Moreover, low pH, such as pH 4 did not release all of the bound protein (34%), while a combination of low pH and increased salt concentration (0.5 M NaCl, 0.2

M glycine, pH 4) released all bound protein. G. Grass et. al., Infection and Immunity, p. 213-228 (2004) discloses that in the bacterial expression of metalloproteinases, the washing procedure with high ionic strength buffer (3 M NaCl) did not release the protein. The protein could, however be released by butanol or a detergent. C. M. Mounier et al., J. Biol. Chem. 279, No. 24, pp. 25024-25038 (2004) reports for HEK293 and CHO cells that proteins expressed by said cells bind to the cell surface. This could be inhibited by increased salt concentration (NaCl) in the range of 0.12 to 1 M. At 1 M all proteins seemed to be released. In one example with HEK293 the cells were treated with 1M NaCl and the released protein increased three times. M. Fannon et al., Biochemistry 39, 1434-1445 (2000) reports on the binding of proteins to fibroblasts. Three different washing procedures were compared, high salt (2 M NaCl, pH 7.4), low pH (20 mM sodium acetate, pH 4) and high salt, low pH (2 M NaCl, pH 4). All buffers do under certain circumstances release the protein. High salt and low pH is effective in all experiments. M. E. Zuber et al., J. Cell Physiology, 170: 217-227 (1997) reports that the protein binding to the surface of CHO cells could be inhibited by high salt/low pH treatment (2 M NaCl, pH 4). J. Norbeck et al., FEMS Microbiology Letters 137, p. 1-8 (1996) reports about yeast cells which were subjected for 0.4 M NaCl for a period of 1.5 h during growing and about the effects thereof on the expression rate of various proteins. Finally, P. M. Dey et al., Planta 202:179-187 reports on the isolation of hydoxyprolinerich glycoproteins from suspension-cultured potato cells by washing the potato cells with a solution containing 50 mM $CaCl_2$ and 2 mM ascorbic acid.

In view of the above it is apparent that a general method to increase the recovery of recombinant proteins in eukaryotic or mammalian expression systems is still desirable. Of particular interest are methods for the serum-free production of proteins which are needed for medical applications (such as plasma proteins including blood clotting factors which are required for the treatment of hemophilic disorders) and for which the serum-free product is desirable for obvious reasons. Hemophiliacs are suffering from hemorrhagic morbidity caused by the disturbed function of protein components of the blood coagulation cascade. Depending on the affected clotting factor, the hemophilia is classified in two types, hemophilia A and B, in both of which the conversion of soluble fibrinogen to an insoluble fibrin-clot is inhibited. They are recessive X-chromosomally-linked genetic disorders affecting mainly the male population.

Hemophilia A affects 1-2 individuals per 10.000 males. This is a genetic disorder that affects the ability of the blood to form an effective clot and thereby results in prolonged bleeding. As hemophilia A is an X-chromosome linked recessive disorder, almost exclusively men are affected. It is caused by the deficiency or absence of factor VIII, a very large glycoprotein (Mr approximately 330 kDa (Furie B., Furie B. C., Cell (1988) 53, 505-518; the sequence thereof is given in SEQ ID NO:2)), which represents an important element of the blood coagulation cascade. The polypeptide sequence of FVIII can be subdivided in three regions, an N-terminal region consisting of the so-called A1 and A2-domains, a central B-domain region and a C-terminal region composed of the A3, C1 and C2 domains. In the blood coagulation factor VIII occurs as an inactive precursor. It is bound tightly and non-covalently to von Willebrand Factor (vWF), which acts as a stabilizing carrier protein. Proteolytic cleavage of factor VIII by thrombin at three specific positions (740, 1372, 1689; see SEQ ID NO:2) leads to its dissociation from vWF and releases the procoagulant function within the cascade. In its active form factor VIII functions as a cofactor for factor IXa, thereby accelerating the proteolytic activation of factor X by several orders of magnitude.

Hemophilia B occurs in about 1 of 25,000 males. It is characterized by a deficiency of the serine protease factor IX (Christmas factor; see SEQ ID NO:11). The gene encoding factor IX is localized on the X-chromosome (locus Xq27) making hemophilia B an X-chromosome linked recessive disorder. This 415 amino-acid polypeptide is synthesized in the liver as a 56 kDa glycoprotein. In order to attain its proper function a posttranslational carboxylation step is required which only occurs in the presence of vitamin K.

Treatment of these types of bleeding disorders traditionally involves infusions of human plasma-derived protein concentrates of the missing factor(s), i.e. replacement therapy. Although this method represents an efficient therapy for hemophiliacs, it carries the risk of transmission of various infectious agents, such as viruses causing hepatitis or AIDS, or thromboembolic factors. Alternatively several recombinant DNA techniques for the production of clotting factors have been described. The corresponding cDNAs of wild type factor VIII and factor IX have been isolated and cloned into suitable expression vectors (EP-A-160457; WO-A-86/01961, U.S. Pat. Nos. 4,770,999, 5,521,070 and 5,521,070).

In the case of factor VIII, recombinant expression of subunits for the production of complexes showing coagulant activity is known in the art (e.g., from EP-A150735, EP-A-232112, EP-A-0500734, WO-91/07490, WO-95/13300 U.S. Pat. Nos. 5,045,455 and 5,789,203). Moreover, the expression of truncated cDNA-versions partially or entirely lacking the sequence coding for the highly glycosylated B-domain have been described (e.g. in WO-86/06101, WO-87/04187, WO87/07144, WO-88/00381, EP-A-251843, EP-A-253455, EP-A-254076, U.S. Pat. Nos. 4,868,112 and 4,980,456, EP-A-294910, EP-A-265778, EP-A-303540, WO91/09122 and WO 01/70968.

The following passages provide details on human factor VIII because it was chosen as a model recombinant protein to illustrate the present invention.

The gene encoding the factor VIII protein is situated at the tip of the long arm of the X chromosome on locus Xq28. It spans over 186 kb, and thus is one of the largest genes known. The factor VIII gene comprises 26 exons and its transcription and subsequent processing results in a 9-kb mRNA. Translation of this mRNA leads to a polypeptide chain of 2351 amino acids, containing a signal peptide of 19 and a mature protein of 2332 amino acids (see SEQ ID NOs:1 and 2). Analysis of the primary structure determined from the cloned factor VIII cDNA revealed the organization in structural domains occurring in the order A1-a1-A2-a2-B-a3-A3-C1-C2.

The short spacers a1, a2 and a3 are so-called acidic regions containing clusters of Asp and Glu residues and are in literature often included in the A-domains resulting in the slightly simplified domain structure A1-A2-B-A3-C1-C2. Following translation and posttranslational modification, the primary translation product, having a molecular mass of approximately 300 kDa, undergoes intracellular proteolysis when leaving the Golgi apparatus processing the primary translation product into an amino terminal heavy chain of 90-210 kDa (A1-a1-A2-a2-B) and a carboxy terminal light chain of 80 kDa (a3-A3-C1-C2), giving rise to the heterodimeric molecule circulating in blood plasma. In this heterodimeric molecule the heavy and light chain of factor VIII are noncovalently linked by divalent metal ions. The span in molecular weights of the heavy chain is the result of different degrees of proteolytic cleavage of the B-domain. The more or less truncated B-domain remains attached to the A2-domain. The B-domain does not seem to have an influence on the biological activity of the FVIII molecule. This is supported by the fact that during activation of the FVIII the entire B-domain is cleaved off. Immediately after its release into the bloodstream, the FVIII heterodimer interacts with a carrier protein called "von Willebrand factor" (vWF). This interaction stabilizes the heterodimeric structure of FVIII increasing the half-life of FVIII in the blood circulation. Furthermore the complex-formation with vWF prevents the premature binding of factor VIII to cell membranes and components of the tenase complex. Also proteolytic cleavage of the FVIII molecule is to some extent prevented with the molecule being non-covalently bound to vWF. However, thrombin cleavage of FVIII is still possible and results in a loss of affinity to vWF and the conversion of FVIII to its active form.

As could be seen in the preceding paragraph, factor VIII is a complex glycoprotein resulting in a difficult production process to maintain structural integrity and stability of the protein. Especially the B-domain harboring totally 19 of the altogether 25 N-linked glycosylation sites makes manufacturing of the full length protein difficult, as incorrect glycosylation always bears the risk of immunogenic reactions against the product. The function of the B-domain is not completely elucidated yet, but it has been found that this domain is not essential for the haemostatic function of factor VIII (Sandberg et al., Seminars in Hematology 38, Suppl 4, 24-31 (2001). This observation has been made both in vitro and in vivo for human plasma-derived factor VIII that lacks the entire B-domain, as well as for multiple forms of recombinant factor VIII molecules lacking the entire B-domain. Plasma-derived B-domain deleted factor VIII can be purified from plasma-derived factor VIII concentrates as these concentrates contain multiple active forms of factor VIII ranging in size from 170 kDa to 280 kDa most likely resulting from differences in the length of the B-domain still contained in the heterodimeric protein, supporting the finding that the B-domain is not essential for the biological activity of factor VIII (Eriksson et al., Seminars in Hematology 38, Suppl. 4, 24-31 (2001). In addition to its increased structural stability, transfection of eukaryotic cells with cDNA of the B-domain deleted factor VIII also yielded improved expression levels of the protein (Herlitschka et al., Journal of Biotechnology 61, 165-173 (1998)). These features resulted in one B-domain deleted recombinant factor VIII product being available on the market, showing comparable safety and efficacy as full length recombinant and plasma-derived factor VIII.

Generally deletion of the B-domain has been done on the cDNA-level resulting in the reduction of the overall size of the full-length factor VIII molecule by approximately 40% from 2332 amino acids to 1440 amino acids. The C-terminus of the heavy chain and the N-terminus of the light chain has in some cases been joined using a short amino acid linker replacing the entire B-domain with its 908 amino acids such in WO 00/49147 and WO 01/70968). The N-terminus of the linker described in these references was derived from the N-terminus of the B-domain whereas the C-terminus consists of a specially designed linker sequence. Like the full length recombinant factor VIII and the plasma-derived factor VIII, the majority of the B-domain deleted factor VIII is secreted as a non-covalently linked heterodimer of the heavy and the light chain. Also a small amount of non-cleaved single chain B-domain deleted recombinant factor VIII with a molecular weight of 170 kDa is secreted. Extensive studies have shown that binding to von Willebrand factor and activation by thrombin cleavage as well as interaction with several other physiologically relevant molecules is comparable to that described for the natural human factor VIII.

Recombinant factor VIII products exist. As the abundance of mRNA transcripts is very low (only $10^{-5}$ of the total mRNA of the liver) it took long to obtain the complete cDNA transcript of the protein. With this major breakthrough in the 1980s and the successful transfection of CHO cells with the cDNA, the first recombinant factor VIII product was introduced to the market in 1992. Since then, the annual sales of recombinant factor VIII preparations have reached values >1 billion US$ (Schmid: Pocket Guide to biotechnology and genetic engineering; Wiley-VCH (2003)). Currently four different recombinant factor VIII preparations are available on the market. The manufacturers of these four preparations cover approximately 60% of the demand for factor VIII preparations in the developed countries. However, capacity is still not sufficient and methods to increase the yield of a production process for a recombinant protein will be particularly beneficial for the production of recombinant factor VIII.

In the production of a recombinant B-domain deleted FVIII according to WO 01/70968, HEK cells were transformed with a gene for FVIII, transformed cells were cultivated and FVIII was secreted. During the harvest of the cells, the FVIII molecule and the cells were separated using centrifugation or filter membranes. The recovered cell-free FVIII containing media was then further processed through purification steps to remove host cell proteins, DNA and other contaminants. The recovery rates of the expressed FVIII obtained so far were only moderate.

In general and specifically for the recombinant production of proteins (including plasma proteins such as FVIII), it is very important to optimize the process to achieve a high productivity of the product. This is essential for the economy of the product as the recombinant production procedure is relatively expensive and sensitive for disturbances (infections, etc.) due to its biological origin.

SUMMARY OF THE INVENTION

In view of the above, it is desirable to establish a serum-free production method providing increased yields of recombinant protein. Surprisingly it was found that by a very simple measure, the yield of a recombinant protein to be harvested from the serum-free culture medium can be increased approximately 2 to 20-fold. Thus, the present invention provides a method to improve the yield of recombinant proteins produced by cultivating eukaryotic cells under serum-free conditions. In more detail, the present invention provides:

(1) a method for the recombinant production of at least one target protein in eukaryotic cells, which comprises effecting cultivation of eukaryotic cells, being capable of expression of said at least one target protein, under serum-free conditions and subjecting a suspension of said cells, prior to separation of the protein from the cells, to a non-physiologically increased concentration of at least one ionic substance;

(2) a preferred mode of the method according to embodiment (1), wherein said at least one ionic substance is a salt, an amino acid or a mixture of peptides and/or amino acids, preferably the salt is an alkaline or alkaline earth metal salt such as a salt of the Hofmeister series, the amino acid is an amino acid with charged R-group, and the mixture of peptides and amino acids is a peptone;

(3) a preferred mode of the method according to embodiment (1) or (2), which comprises one or more of the following steps:

(a) cultivating the cells in a culture medium;
(b) separating the culture medium from the cultivated cells, resulting in two separate fractions, a fraction of cultivated cells and a fraction of liquid medium;
(c) contacting or suspending the fraction of cultivated cells with a release composition comprising a non-physiologically increased concentration of at least one ionic substance as defined in (1) or (2) above;
(d) removing the culture medium from the cells, resulting in two separate fractions, a fraction of cells and a fraction of release composition;
(e) isolating the plasma protein from the fraction of the release composition; and
(f) suspending the fraction of cells of (d) above in culture medium and reculture; and (4) a protein composition or a pharmaceutical composition obtainable by the methods (1) to (3) as defined above.

The gist of the present invention resides in the use of an ionic substance, which is added to the cell suspension (or directly the culture medium) immediately prior to harvest. The addition of the ionic substance to the cell suspension allows both disruptive isolation methods (where the cells are destroyed) and methods where the desired protein is secreted. In case of the latter the method may be adapted to a cyclic process, after subjecting the cell suspension to the increased ionic substance, separation of the suspension into cell fraction and liquid fraction and isolation of a desired protein from the liquid fraction, the cell fraction may be recultured, e.g. as specified in embodiment (3) above.

BRIEF DESCRIPTION OF THE FIGURES

FIG. 1 shows a cultivation procedure.

FIG. 3A (Western Blot method 1): lane 1: Molecular mass marker (SeeBlue); lane 2: Standard rFVIII (Refacto, Wyeth), 200 IU/ml; lane 3: rFVIII from a release procedure using 0.1 M NaCl (Example 6A), 9 IU/ml; lane 4: rFVIII from a release procedure using 0.55 M NaCl, 18 IU/ml (Example 6D); lane 5: rFVIII from a release procedure using 0.55 M NaCl, 16 IU/ml (Example 6A); lane 6: rFVIII from a release procedure using 0.55 M NaCl, 13.6 IU/ml (Example 7B). FIG. 3B (Western Blot method 2, high sensitivity): lane 1: Molecular mass marker; lane 2: Reference cell suspension FVIII 1 IU/ml; lane 3: Reference cell suspension FVIII 0.2 IU/ml; lane 4: rFVIII from a release procedure using 0.2 M $CaCl_2$, 1.6 IU/ml (Example 6A); lane 5: rFVIII from a release procedure using 0.2 M $CaCl_2$, 0.73 IU/ml (Example 6A); lane 6: rFVIII from a release procedure using 0.1 M $CaCl_2$, 1.73 IU/ml (Example 8A); lane 7: rFVIII from a release procedure using 0.1 M $CaCl_2$, 0.87 IU/ml (Example 8A); lane 8: rFVIII from a release procedure using 0.55 M NaCl, 1.81 IU/ml (Example 6A).

DETAILED DESCRIPTION OF INVENTION

Figure 2:
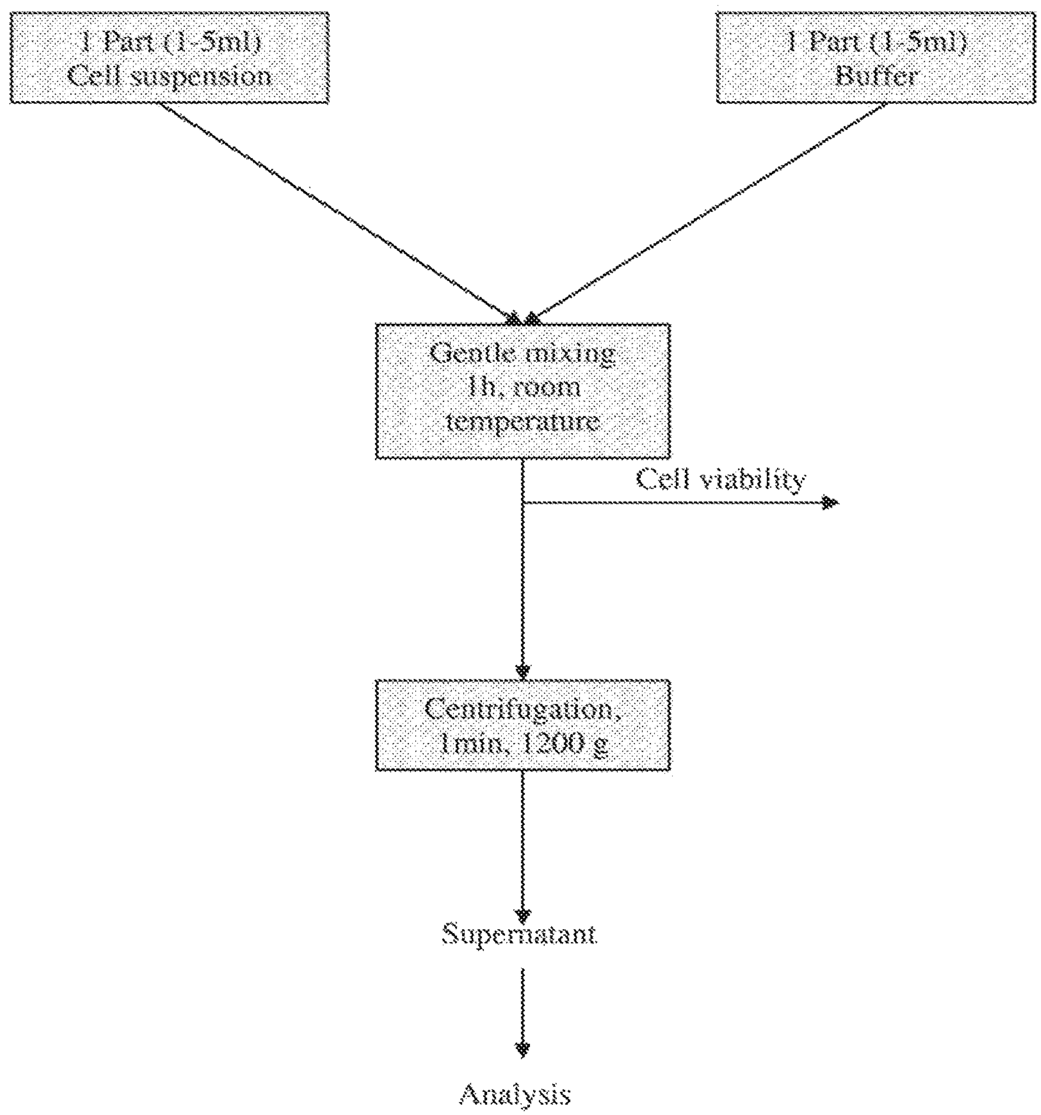
FIG. 2 is a flow chart of the experimental set up for small scale experiments. First, the cell suspension and the ionic substance in liquid form (buffer) are mixed and incubated for 1 h at room temperature. Following the incubation the viability of the cells is checked, before the cells are separated from the medium via centrifugation. The supernatant (cell free medium) is then analysed for the recombinant protein or frozen for later analysis.

The term "yield" within the meaning of the invention is defined as the change in release of FVIII compared with the yield obtained using normal harvest procedures (harvest without addition of charged substances) or compared with harvest procedures with addition of physiological salt levels or lower, typical 0.1 M NaCl was added to the cell culture medium.

The term "serum-free" refers to the transfection and culturing of cells in medium containing suitable supplements except any kind of serum. Supplements are selected from amino acids, lipids, trace elements, vitamins and other growth enhancing components. Often the "serum-free" culture conditions are even more stringent and, if no exogenous protein is added, or already included in the medium, the medium is called "protein-free".

The term "protein" includes naturally synthesized proteins which are encoded by genes of the cultivated cell as well as recombinant proteins secreted by cells. Recombinant proteins are those which are encoded by transgenes introduced into the cells by molecular biology techniques. In accordance with the invention, "protein" includes proteins of human and animal origin, but also proteins of other sources such as plants, insects, etc., and mutated, artificial, synthetic, fusion or chimeric proteins. In particular "protein" includes plasma proteins, peptide hormones, growth factors, cytokines and antibodies. In more detail, plasma proteins include human and animal blood clotting factors such as fibrinogen, prothrombin, thrombin, FX, FXa, FIX, FIXa, FVII, FVIIa, FVIII, FVIIIa, FXI, FXIa, FXII, FXIIa, FXIII, FXIIIa, von Willebrand factor etc., transport proteins such as albumin, transferrin, ceruloplasmin, haptoglobin, hemoglobin, hemopexin, etc., protease inhibitors such as ß-antithrombin, α-antithrombin, α2-macroglobulin, Cl-inhibitor, tissue factor pathway inhibitor (TFPI), heparin cofactor II, protein C inhibitor (PAI-3), Protein C, Protein S, etc., antiangionetic proteins such as latent-antithrombin, etc., highly glycosylated proteins including alfa-1-acid glycoprotein, antichymotrypsin, inter-α-trypsin inhibitor, α-2-HS glycoprotein, C-reactive protein, etc. and other proteins such as histidine-rich glycoprotein, mannan binding lectin, C4-binding protein, fibronectin, GC-globulin, plasminogen, blood factors such as erythropoietin, interferon, tumor factors, tPA, gCSF and derivatives and muteins thereof. Preferably the plasma protein is a human factor VIII protein (see SEQ ID NO:2 for the full length protein) or a human factor IX protein (see SEQ ID NO:11 for the full length protein) or muteins thereof. A mutein of the human factor VIII protein is e.g., a B-domain deleted factor VIII protein.

A particular factor VIII mutein in which the B-domain between positions Arg740 and Glu1649 has been replaced by an Arg-rich linker peptide having at least 3 Arg residues and comprising 10 to 25 amino acid residues (wherein said factor VIII numbering is relative to the mature wild-type factor VIII sequence shown in SEQ ID NO:2) is disclosed in WO 01/70968 which is herewith incorporated in its entirety. It is preferred that the Arg-rich linker peptide has 14 to 20 amino acid residues, while a linker comprising:

the amino acid sequence SFSQNSRH (SEQ ID NO:7), and/or the amino acid sequence QAYRYRRG (SEQ ID NO:8), and/or the amino acid sequence SFSQNSRHQAYRYRRG (SEQ ID NO:9)

is particularly preferred. Most preferred is a factor VIII mutein, which comprises amino acids 1 to 1440 of SEQ ID NO:4, or even more, a factor VIII mutein having SEQ ID NO:4.

The factor VIII protein or factor VIII mutein as defined hereinbefore may have one or more of the following (additional) mutations (a), (b) and (c):

(a) Val at position 162 has been replaced by a neutral amino acid residue selected from Gly, Ala, Leu, Ile, Met and Pro;
(b) Ser at position 2011 has been replaced by a hydrophilic amino acid residue selected from Asn, Thr and Gin; and
(c) Val at position 2223 has been replaced by an acidic amino acid residue selected from Glu and Asp (again said factor VIII numbering is relative to the mature wild-type factor VIII sequence shown in SEQ ID NO:2).

Preferred is a factor VIII protein or factor VIII mutein that has at least one of the mutations (a) and (b) or has all three mutations (a), (b) and (c).

Furthermore, preferred mutations in (a) to (c) are the following: (a) Val at position 162 has been replaced by Ala, (b) Ser at position 2011 has been replaced by Asn, and/or (c) Val at position 2223 has been replaced by Glu.

Particularly preferred is a factor VIII mutein, which comprises amino acids 1 to 1440 of SEQ ID NO:6, or even more, a factor VIII mutein having SEQ ID NO:6

There is no limitation on the vectors for the expression of the proteins of the invention. Suitable vectors include vectors of the pUC series, such as pUC19 (MBI Fermentas) and modifications thereof as utilized in WO 01/70968, which is herewith incorporated in its entirety. The vectors for the particularly preferred factor VIII muteins mentioned hereinbefore, are pTGF8-3 and pTGF8-2hyg-s, the structure of which being shown in FIG. 4 and the exact DNA sequences thereof being given in SEQ ID NOs:3 and 5, respectively. The preparation of said vectors is disclosed in WO 01/70968.

A further preferred plasma protein is factor IX or a mutein thereof, preferably is wild-type human factor IX shown in SEQ ID NO: 11. Suitable muteins of factor IX include point mutated and truncated forms of the factor IX. Vectors for expression of factor IX, such as pTGFG36hyg and pTGFG36 (the 5753 bps circular DNA of the latter being given in SEQ ID NO: 10; bases 689-2071 within SEQ ID NO:10 coding for the factor IX protein) are disclosed in WO 01/70968.

The terms "eukaryotic cells" and "eukaryotic cell" according to the invention include isolated cells or isolated tissue of multicellular organisms such as vertebrates (including mammals (viz. humans, rodents, etc.), fish, etc.), invertebrates (including insects, worms, etc.) and plants (higher plants, algae, fungi, etc.); or can be lower eukaryotic cells such as yeasts, etc. Particularly preferred eukaryotic cells for the present invention are mammalian cells including animal and human cells which are kept in culture medium. Particularly preferred for the production of human proteins such as human plasma proteins are human cells such as primary cells or immortalized cells such as kidney, bladder, lung, liver, cardiac muscle, smooth muscle, ovary or gastrointestinal cell. Most preferred are human foetal kidney cells such as 293 (DSM ACC 305), 293T (DSM ACC 2494), and 293F and 293H (Invitrogen 11625-019 and 11631-017, respectively) etc. Other particularly suitable cells are Cos, CHO, hybridoma, myeloma such as NSO cells and insect cells. Particularly preferred are cells out of the above, which are adapted to be cultivated under serum-free conditions.

In a preferred embodiment the mammalian cells, including those mentioned above are stably transfected with an expression cassette carrying the gene coding for the protein or plasma protein.

The increasing (adjusting) of the concentration of the ionic substance in the cell suspension is effected by adding to the cell suspension a release composition comprising said at least one ionic substance. The release composition can be added to the cell suspension in solid or liquid form. It is, however, preferred that the release composition is being added to the cell suspension up to 72 h, preferably 12-24 h and most preferable 1 to 120 min prior to the separation of the protein. In a preferred mode of the method of the invention the release composition is directly added to the culture broth or added to the cells or to a suspension of the cells isolated from the culture broth. The release composition may be added in one step or may be gradually added to reach the final concentration within 1-4300 minutes. The release composition may also be added with diafiltration technique.

"Non-physiologically increased concentration of an ionic substance" refers to a concentration of the ionic substrate which is higher than the concentration in the cell/in the optional culture medium of the cell at normal conditions (for example in vitro).

The "ionic substances" according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, KCl, KBr, $KNO_3$, $KClO_4$, KI, KSCN, $Na_3PO_4$, $Na_2HPO_4$, $NaH_2PO_4$, $Na_2SO_4$, $NaCH_3COO$, NaCl, NaBr, $NaNO_3$, $NaClO_4$, NaI, NaSCN, $ZnCl_2$ $Cs_3PO_4$, $Cs_2HPO_4$, $CsH_2PO_4$, $Cs_2SO_4$, $CsCH_3COO$, CsCl, CsBr, $CsNO_3$, $CsClO_4$, CsI, CsSCN, $Li_3PO_4$, $Li_2HPO_4$, $LiH_2PO_4$, $Li_2SO_4$, $LiCH_3COO$, LiCl, LiBr, $LiNO_3$, $LiClO_4$, LiI, LiSCN, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)_2$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are $NH_4$Acetate, $MgCl_2$, $KH_2PO_4$, $Na_2SO_4$, KCl, NaCl, and $CaCl_2$.

The preferred amino acid is an amino acid with a charged R group (side chain), such as basic amino acids including amino acids selected from arginine, histidine, lysine, etc.

The preferred peptone is a soy peptone, preferably having an average molecular weight of below 1000 g/mol, preferably between 500 and 600 g/mol.

In a preferred embodiment of the invention the ionic substance is added to reach the equilibration balance within protein and cell surface, enough to disrupt the ionic binding and release bound proteins from the cell surface without destroying the cell. According to the invention at least one ionic substance, preferably two and most preferably three or more ionic substances is/are added.

Moreover, it is preferred that no or only small amounts of non-ionic detergents are added to the suspension and/or are present in the release composition. Particularly preferred is that the release composition is free of non-ionic detergents.

The release composition as defined hereinbefore may further comprise a additional buffering substance to stabilize and keep the suspension at a certain pH. It is to be considered that some of the ionic substances defined above do possess excellent buffering properties. Thus, if ionic substances having no or only low buffering properties are utilized, such additional buffering substances are required. The choice of suitable additional buffering substances of course depends on the cell system and the pH to be kept. Such additional buffering substances include HEPES, MES, TRIS, etc. Generally, the pH of the cell suspension when subjected to the increased concentration of the at least one ionic substance is in the range of stability for the selected protein, for FVIII it is about 6.0 to 7.5.

In a preferred embodiment of the invention the ionic substance and its concentration is selected in such a manner that the cells can be continuously cultivated under simultaneous release of the protein. Preferably the protein is then removed from the culture broth using for example a continuous centrifuge or diafiltration over a micro filter membrane. This allows the protection of sensitive proteins from proteolytic degradation, etc., due to fast removal from the culture broth.

In a particularly preferred embodiment the ionic substance and its concentration is selected in such a manner that the viability of the cells is maintained. Also by harvesting of the protein the viability of the cells is maintained, after harvest the non-naturally increased concentration of the ionic substance is reduced or the cells are transferred into fresh culture medium, to enable a cyclic production process of the protein. This enables the claimed process to be run cyclically as set forth in embodiment (3) above.

Furthermore, the preferred mode of addition and the preferred concentration of the preferred ionic substance NaCl, KCl, $CaCl_2$, arginine, histidine and lysine are the following:

NaCl may be added to raise the concentration in the suspension to at least 0.2 M, preferably to a concentration ranging from 0.2 to 2 M, more preferably from 0.4 to 1 M, most preferably to a concentration of about 0.5 M. In particular, the concentration thereof in the suspension may be in the range of 0.2 M up to saturation of the solution, preferably is in the range of 0.2 to 2M, or 0.2 to 1 M, or 0.2 to 0.8 M, or 0.2 to 0.6 M, or 0.2 to 0.5 M, or 0.4 to 1 M, or 0.4 to 0.8 M, or is about 0.5 M.

KCl is added to raise its concentration in the suspension to at least 0.2 M, preferably to a concentration ranging from 0.2 to 2 M, more preferably from 0.4 to 1 M, most preferably to a concentration of about 0.5 M. In particular, the concentration thereof in the suspension may be in the range of 0.2 M up to saturation of the solution, preferably is in the range of 0.2 to 2 M; or 0.2 to 1 M, or 0.2 to 0.8 M, or 0.2 to 0.6 M, or 0.2 to 0.5 M, or 0.4 to 1 M, or 0.4 to 0.8 M, or is about 0.5 M.

$CaCl_2$ may be added to raise its concentration in the suspension to above 0.002 M, preferably >0.002 to 0.5 M, more preferably from 0.05 to 0.2 M, most preferably to a concentration of about 0.1 M. In particular, the concentration thereof in the suspension may be in the range of 0.002M up to saturation of the solution, preferably in the range of 0.002 to 0.5 M, or 0.002 to 0.2 M, or 0.002 to 0.1 M, or 0.002 to 0.05 M, or 0.002 to 0.025 M, or 0.01 to 0.1 M, or 0.05 to 0.15 M, or is about 0.1 M.

Arginine may be added to raise its concentration in the suspension to at least 0.2 M, preferably to a concentration ranging from 0.2 to 2 M, more preferably from 0.4 to 1 M, most preferably to a concentration of about 0.8 M. In particular, the concentration thereof in the suspension is in the range of 0.2 M up to saturation of the solution, preferably may be in the range of 0.2 to 2 M, or 0.4 to 1.5 M, or 0.4 to 1.2 M, or 0.4 to 1.0 M, or 0.4 to 0.8 M, or 0.6 to 0.9 M, or 0.6 to 0.8 M, or is about 0.75 M.

Lysine may be added to raise its concentration in the suspension to at least 0.2 M, preferably to a concentration ranging from 0.2 to 2 M, more preferably from 0.4 to 1 M, most preferably to a concentration of about 0.8 M. In particular, the concentration thereof in the suspension is in the range of 0.2 M up to saturation of the solution, preferably may be in the range of 0.2 to 2 M, or 0.4 to 1.5 M, or 0.4 to 1.2 M, or 0.4 to 1.0 M, or 0.4 to 0.8 M, or 0.6 to 0.9 M, or 0.6 to 0.8 M, or is about 0.75 M.

Histidine may be added to raise its concentration in the suspension to at least 0.01 M, preferably to a concentration ranging from 0.01 to 0.3 M, more preferably from 0.02 to 0.3 M. In particular, the concentration thereof in the suspension is in the range of 0.02 M up to saturation of the solution, preferably may be in the range of 0.02 to 0.3 M, or 0.03 to 0.3 M, or 0.05 to 0.3 M, or 0.1 to 0.3 M, or 0.2 to 0.3 M or is about 0.3 M.

The mixture of peptides and/or amino acids or the peptone is added to raise its concentration in the cell suspension to at least 0.01% (w/w), preferably to a concentration ranging from 0.1 to 20% (w/w) peptone. For a cyclic process it is particularly preferred to use a peptone concentration of 0.2 to 10% (w/w), preferably a peptone concentration of about 5% (w/w). For a non-cyclic (i.e., batch) process it is preferred to use a peptone concentration of 10% (w/w) or greater, preferably a peptone concentration of about 20% (w/w).

In a preferred embodiment of the method of embodiments (1) to (3) as defined above, two ore more ionic substances are mixed with each other, the concentration of each of the added ionic substances is divided with the total amount of added ionic substances, to exert the same releasing capacity as when only one ionic substance is added.

Particularly preferred in the method as defined above is that the ionic substances which are mixed with each other are selected from at least 3 different ionic substances selected from; an amino acid with charged R group (such as arginine, histidine or lysine) in a concentration ranging from 0.05 to 0.2 M; NaCl and KCl in a concentration ranging from 0.1 to 0.2 M and $CaCl_2$ in a concentration ranging from 0.01 to 0.05 M.

The concentration of a mixture of ionic substances needed to reach the desired release of proteins is mainly dependent on two factors, the number of ionic substances and the concentration of each ionic substance. Thus, if more ionic substances are mixed, less concentration of each is needed to reach the maximum product release. In principle, this can be calculated on a mathematical basis. However, in specific cases, the ionic substances can exert combinatorial effects, which lower the need of concentration of ionic substances compared with a theoretical estimation.

If a combination of NaCl and lysine is used in the release composition, the following concentrations are preferably used: NaCl at least 0.1 M, preferably at a concentration ranging from 0.1 to 1 M, more preferably from 0.2 to 0.5 M, most preferably about 0.25 M; lysine at least 0.1 M, preferably at a concentration ranging from 0.1 to 1 M, more preferably from 0.2 to 0.5 M, most preferably about 0.4 M.

If a combination of NaCl, histidine and $CaCl_2$ is used in the release composition, the following concentrations are preferably used: NaCl at least 0.05 M, preferably at a concentration ranging from 0.05 to 0.6 M, more preferably from 0.075 to 0.35 M, most preferably about 0.1 M; histidine at least 0.01 M, preferably at a concentration ranging from 0.01 to 0.3 M, more preferably from 0.025 to 0.15 M, most preferably bout 0.05 M; and $CaCl_2$ at least 0.005 M, preferably at a concentration ranging from 0.01 to 0.25 M, more preferably from 0.025 to 0.15 M, most preferably at about 0.05 M.

It was found that by a combination of ionic substances only a low concentration of each ionic substance is required and therewith the protein releasing properties of the composition is maintained and acceptable cultivation conditions for the cells are provided. In a further preferred embodiment the ionic release composition is selected so that at least one component acts as an stabilizer for the released protein being active before and/or after the separation of protein and cells.

In a further preferred embodiment of the method of embodiments (1) to (3) as defined above the cultivation of the cells may be affected in suspension culture or adherent culture.

Moreover, it is preferred that the separation of the medium from the cultivated cells in steps (b) and (d) is effected by centrifugation, filtration, diafiltration, dead end filtration or micro filtration. A method the skilled artisan may be aware of can be utilized for the isolation of the plasma protein from the medium and its purification. Particularly, this may be effected by using at least one technique selected from immuno-affinity chromatography, affinity chromatography, protein precipitation, buffer exchanges, ionic exchange chromatography, hydrophobic interaction chromatography, mixed mode hydrophobic/ion exchange chromatography media, chelating chromatography, carbohydrate affinity like lectin or heparin affinity chromatography, size-exclusion chromatography, electrophoresis, dialysis, different precipitation agents such as polyethylene glycol, ammonium sulfate, ethanol, hydroxy apatite adsorption, filter membrane adsorption, etc. For a person skilled in the art, it is easily apparent that the carrier (the part on which the active ligand is attached) within the chromatography field, may be comprised of different types of carrier like resins, particles, beads, membranes, hollow fiber, etc., and that the carrier may consist of different materials, like cross linked agarose, cellulose, polysulfon, silica, etc.

In a preferred embodiment of the method of the invention the isolation of the protein comprises a capture step, where the product is bound and cell cultivation media and washing solution is washed away, preferably the capture step utilizes a chromatography media. Furthermore steps (d) and (e) of embodiment (3) may be effected by mixing the cell suspension with a chromatographic medium which binds the product and thereafter the chromatography media is removed from the cell suspension.

It is moreover preferred that the method according to the invention is performed under sterile, in particular good manufacturing practice (GMP) conditions as the resulting product is a pharmaceutical raw material. For the same reason it is preferred that the medium and/or the purified protein is subjected to a virus inactivation step.

According to the invention the cultivation is effected under serum free conditions, which facilitates the work-up of the culture broth and the solution of the plasma protein. In some instances it is preferred to culture under protein-free conditions. Other embodiments, e.g. a process where the ionic substance is a mixture of peptides and/or amino acids (peptone), however, require the addition of functional proteins such as insulin or insulin-like growth factors, etc.

Finally, it is preferred that the cell suspension is processed with a micro filtration system where the pore in the filter has been chosen to retain the cells and the cell suspension thereafter is processed with the release solution through the diafiltration procedure where the concentration of the release solution gradually is increased and the product is recovered in the filtrate of said micro filtration system.

In particular does the invention relate to a method to increase the product recovery during the harvest of FVIII or B-domain deleted FVIII including that defined hereinbefore (hereinafter shortly referred to as FVIII) from cultivated cells. The recovery of FVIII can be significantly increased with relatively simple measures. Due to the addition of ionic substances to the medium prior to the separation of the cells from the cultivation medium,—thereby raising the concentration of those ionic substances above the physiological level found in cells—the FVIII recovery has been increased in the range of 200-2000% (2-20 times).

A suitable explanation seems to be that ionic groups on the cell membrane retard the factor VIII molecules. When the ion-concentration is increased in the medium, which is in contact with the cell surfaces, the ions counteracts the ions on the cell surface, and factor VIII is released.

In a first particularly preferred embodiment of embodiments (1) to (3) of the invention, sodium chloride is increased to 0.5 M NaCl before the removal of the cells from the cultivation media. It was shown that with such release composition the recovery of FVIII in the cell free cultivation media was increased 20 times compared to the use of 0.1 M sodium chloride, whereas the release of host cell proteins was only slightly increased. 0.5 M sodium chloride is not a normal environment for cells (physiological salt conditions is comparable with about 0.15 M sodium chloride), but the treatment did not destroy the cells. However, if the salt concentration is further increased up to 1M sodium chloride, more than 80% of the cells have been destroyed (lysis) and the amount of host cell proteins has almost been doubled, whereas the FVIII concentration is about the same as when using the lower salt concentration (0.5 M).

In a second particularly preferred embodiment of the invention, two or more ionic substances are mixed with each other to achieve the product release. For example, it was shown that if 0.25 M sodium chloride is mixed with 0.25 M of lysine it exerts the same product release properties and cell viability as 0.5 M NaCl. In another example 0.17 M NaCl, 0.17 M lysine and 0.3 M sorbitol was used as release composition. This composition gave slightly lower product release compared with 0.5 M NaCl, but illustrates the huge amount of possibilities to choose and combine ionic release substances with each other, achieving similar product release properties. As also shown, different (non-ionic) stabilizers can be added to the releasing composition, without inhibiting the releasing properties.

In a third particularly preferred embodiment $CaCl_2$ is increased to a range from 0.05 to 0.2 M, preferably 0.1M. It was shown in experimental examples that $CaCl_2$ is superior compared to most of other ionic substances, in regard of product-, host cell protein- and DNA release. In addition, the concentration needed for optimal product release, was significantly lower compared to most of the other ionic substances and this can have a considerably advantages, as an ion-exchange step is often used as capture step for further processing. Thus a lower ionic strength means in many cases less dilution before applying the proteins to the capture step. At the same product recovery, 1-2 times higher values for purity in regard of host cell proteins has been achieved and about 10 fold lower values of DNA, compared with the corresponding NaCl composition (0.55M). It was also shown that the use of $CaCl_2$ in some cases exerted stabilizing effects on the product. This was shown as maintained product activity during stability studies at room temperature during several days and that the ratio between biological activity of the product compared to the FVIII antigen content of the product, was close to one.

In a fourth particularly preferred embodiment of the invention the excellent releasing properties of $CaCl_2$ is combined with that of other releasing substances. For instance, a release composition comprising 0.05 M $CaCl_2$, 0.05 M histidine and 0.1 M NaCl showed similar releasing properties as compared to 0.1 M $CaCl_2$ alone. This further highlights the possibilities within the invention, to be able to choose an optimal release composition, depending on product and cell characteristics.

The amount and type of impurities obtained during the harvest procedure can be of importance for the further processing and purification of the product. For example, if the amount of proteases is increased, it can contribute to degradation of the product and it might be necessary to add additional purification steps to achieve the very high demand for purity for recombinantly produced products. During experiments, it has been shown that the amount of released host cell proteins and DNA is also dependent on the ionic substance chosen.

With the method of the invention it is possible to achieve the high protein recovery, in particular high FVIII recovery without destroying the cells and thus limiting the amount of impurities coming out together with the product. At present, best results have been achieved with sodium chloride, potassium chloride, calcium chloride, lysine and a combination of sodium chloride and lysine, a combination of calcium chloride and histidine and a combination of calcium chloride sodium chloride and histidine. Especially the use of calcium chloride has shown interesting results, as the concentration needed for release of FVIII is much lower (about 0.1 M) than that of the other substances (about 0.5-0.8 M). This can be very useful, as it has been shown that using calcium chloride releases lower amount of host cell proteins and DNA. Another important embodiment of the invention is the possibility to reuse the cells for further production of proteins, after the salt release procedure has been used. The salt environment is removed and the cells are dissolved in ordinary cultivation media and can continue to produce.

According to embodiment (4) the invention also relates to a protein preparation or pharmaceutical composition obtained by the method of embodiments (1) to (3), in particular to protein preparations and pharmaceutical compositions comprising a blood coagulation factor such as a FVIII or FIX protein. Such preparations possess excellent purity and due to the advantages of the method of the invention. The pharmaceutical compositions comprising a blood coagulation factor such as a FVIII or FIX protein are particularly suitable for the treatment of hemophiliacs. Such compositions may further contain pharmaceutically acceptable carriers, stabilizers, etc. known to the person skilled in the art.

The following examples are given to illustrate the invention. However, these Examples are not to be construed so as to limit the invention.

EXAMPLES

Materials and Methods

Factor VIII: C, Screening Method Based on Coatest:

The method is based on the two-stage principle, and was performed using micro plate technique. In stage one, activated factor X (Xa) is generated via the intrinsic pathway where factor VIII: C acts as a co-factor. In stage two, Factor Xa is then determined by the use of a synthetic chromogenic substrate, S-2222, in the presence of a thrombin inhibitor 1-2581 to prevent hydrolysis of the substrate by thrombin. The reaction is stopped with acid, and the VIII:C, which is proportional to the release of pNA (para-nitroaniline), is determined photometrically at 405 nm against a reagent blank. The method complies with the requirements in the European Pharmacopoeia. The unit of factor VIII: C is expressed in international units (IU) as defined in the current International Concentrate Standard (IS) established by the World Health Organization (WHO). The routine using buffer containing 1% BSA instead of severe haemophilic plasma for predilutions has been validated. See also literature references (1-4) attached under references.

Total Protein (Protein Determination by Reversed-Phase HPLC):

An HPLC system, equipped with a UV detector and a TSK-gel Octadecyl-NPR column (2.5 μm nonporous particles, 35×4.6 mm I.D., from Tosohaas, Stuttgart, Germany) is used for protein determination. The column, run at 45° C., is equilibrated with 5% acetonitrile in 0.1% trifluoroacetic acid (TFA) (mobile phase A). For elution, 90% acetonitrile in 0.1% TFA (mobile phase B) is used in the linear gradient (0-0.5 min 0% B, 0.5-4 min 0-100% B, 4-5 min 100% B, 5-7 min 0% B). The injection volume is 200 μl and the flow rate is 1.5 ml/min. Detection is carried out by measuring the UV absorbance at 280 nm. Bovine serum albumin (BSA) 10-100 μg/ml (10-20-50-100 μg/ml, n=4) is used for the standard curve. The BSA standard is diluted in 200 mM ammonium acetate and 0.01% Tween® 80, and also the samples, if necessary, is diluted in this solution. The protein concentration in the unknown samples is calculated from the BSA standard curve, which always gives a linear correlation coefficient (r) of >0.99.

Purity (FVIII:C/Total Protein):

The purity for a sample, is calculated taking the value achieved from the FVIII:C analysis and dividing it with the value achieved from the analysis of total protein.

Factor VIII Antigen Analysis (FVIII:Ag):

A microtiter plate is coated with a monoclonal antibody specific for one type of antigenic determinant of the light chain of factor VIII protein in the sample. After incubation with samples a monoclonal peroxidase conjugated antibody is added. This antibody binds to another antigenic determinant of the light chain of factor VIII protein, thus forming a sandwich complex. The enzyme activity, which is proportional to the factor VIII:Ag content in the sample, is then determined through the action of 3,3',5,5'-Tetramethylbenzidine substrate. The reaction is stopped with acid and the colour is read photometrically at 450 nm against a reagent blank.

Specific Activity (Quotient FVIII:C/FVIII:Ag):

The specific activity of a FVIII sample is calculated taking the value achieved from the FVIII:C analysis and divide it with the value achieved from the analysis of FVIII:Ag. The resulting value shows the relationship between biologically active FVIII and total FVIII protein (including both active and inactive forms). For a fully active protein the quotient, FVIII:c/FVIII:Ag, is 1.

Viability (Living Cells/Dead Cells+Living Cells, %):

Cell suspension is diluted with a 0.4% trypan blue staining solution and the cells are thereafter counted in an inverted phase contrast microscope, thus making it possible to determine the cell concentration. Due to the appearance of the cells, it is also possible to make a distinction between living and dead cells. The viability is calculated by dividing the amount of living cells with the total amount of cells and multiplying the results with 100 to receive the viability percentage value. The viability method is further described in R. I. Freshney, Culture of animal cells, $4^{th}$ ed., p. 183-189, Wiley-Liss (2000).

Western Blot Method 1, FVIII Molecular Mass Distribution:

Proteins and peptides in factor VIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane, which is subsequently incubated with a blocking agent. Polyclonal sheep antibodies directed to the whole factor VIII molecule is then added followed by a secondary antibody, which is specific for the Fc part of goat/sheep antibodies. As a third step soluble complexes of goat antibody to horseradish peroxidase (HRP) and HRP are added. FVIII polypeptides are then detected by occurrence of blue bands after incubation with the substrate 4-chloro-1-naphtol.

Western Blot Method 2, Sensitivity 0.5 IU/Ml:

Proteins and peptides in factor VIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane, which is subsequently incubated with a blocking agent. Polyclonal sheep antibody directed to the whole factor VIII molecule is then added followed by a secondary antibody, which is conjugated with horseradish peroxidase and reacts with the heavy and light chains of sheep immunoglobulins. FVIII polypeptides are detected after incubation with the chemiluminescent substrate luminol by exposure to a sensitive X-ray film.

Protease Activity:

Protease activity was determined by a method based on FRET (fluorescence resonance energy transfer) of a fluorescein-casein conjugate. Hydrolysis of casein by proteases release small fluorescein-labelled peptide fragments and an increase in fluorescence is observed. For a quantitative estimate of protease activity, trypsin was used to construct a standard curve. Sample and substrate were incubated on a microplate and the resulting fluorescence was detected with use of a fluorimeter with 485/538 nm excitation/emission wavelengths. The limit of quantification of protease activity corresponded to the proteolytic activity of 500 pg of trypsin/ml when an incubation time of 24 hours was used.

DNA Analysis:

Total DNA is determined using the Threshold Total DNA Assay, which is an enzyme linked assay for single stranded DNA. In the first step the sample is heat denatured to convert all DNA to the single stranded form. Samples are then incubated with a DNA labelling reagent, which contains conjugates of two binding proteins that have high affinities for DNA independent of base sequence. One conjugate is an anti-DNA monoclonal antibody coupled to urease. The other conjugate is a single stranded DNA binding protein coupled to biotin. After incubation, the labelled DNA complex is transferred to a filtration unit on the work station, where it is captured under vacuum control onto a stick which carries a biotinylated nitrocellulose membrane. An excess of streptavidin in the DNA labelling reagent binds specifically to biotin in the DNA complex, and also to biotin attached to the nitrocellulose membrane of the stick. A subsequent wash removes any non-specifically retained enzyme from the membrane and the stick is then placed in a reader, where it is brought into contact with the sensor surface in a very small volume of fluid which contains the enzyme substrate urea. The enzyme reaction changes the local pH at each measurement site, which changes the surface potential on the sensor. The rate of change in surface potential is proportional to the amount of DNA at each site. The surface potential is monitored kinetically and the samples are then quantitated against a standard curve.

The Product:

The product produced in the cell cultivation is a recombinant form of FVIII that has been genetically engineered to contain the active sites of natural FVIII and to exclude the B-domain dispensable for FVIII activity. It is a full-length 170 KDa FVIII polypeptide of which the major portion is processed to give a heavy chain (HCh, 90 KDa) and a light chain (LCh, 80 KDa) polypeptide. The deletion of the B-domain reduces structural complexity while retaining the biological activity similar to that of plasma-derived FVIII. The amino acid sequence of the FVIII mutein isolated in the following examples is given in SEQ ID NOs:4 and 6.

Example 1: Production of Expression Cell Line

Cell Line:

The expression cell line is based on the cell line HEK 293T (or shortly 293T). This cell line was originally generated by transformation of human foetal kidney cells with sheared adenovirus type 5 DNA (F. L. Graham et al., J. Gen. Virol. 36(1), 59-74 (1974)). Into the resulting cell line HEK 293 (shortly 293) the temperature sensitive gene for SV40 T-antigen was inserted. Features of the expression cell line: Name: HEK 293T tsA201; Source: European Collection of Cell Cultures, ECACC cell line #9612 1229, tsA 201 (redeposited according to the Budapest Treaty by Octagene Biomedical Laboratories GmbH, Am Klopferspitz 19, 82152 Martinsried, Germany with the DSMZ—Deutsche Sammlung von Mikroorganismen und Zellkulturen GmbH, Maschenroder Weg 1B, 38124 Braunschweig, Germany, on Feb. 3, 2001, under the deposition # DSM ACC 2494; permission to refer to this deposit was granted by Octagene Biomedical Laboratories GmbH on Mar. 17, 2005); Species: Human; Tissue: foetal kidney; Morphology: Epithelial like; Karyotype: The karyotype of 293T cells (ECACC #96121229) is not specified; the karyotype of 293 cells (ECACC #85120602), however, is known and described as 2n=46, hypotriploid, model chromosome number: 64.

Figure 4:
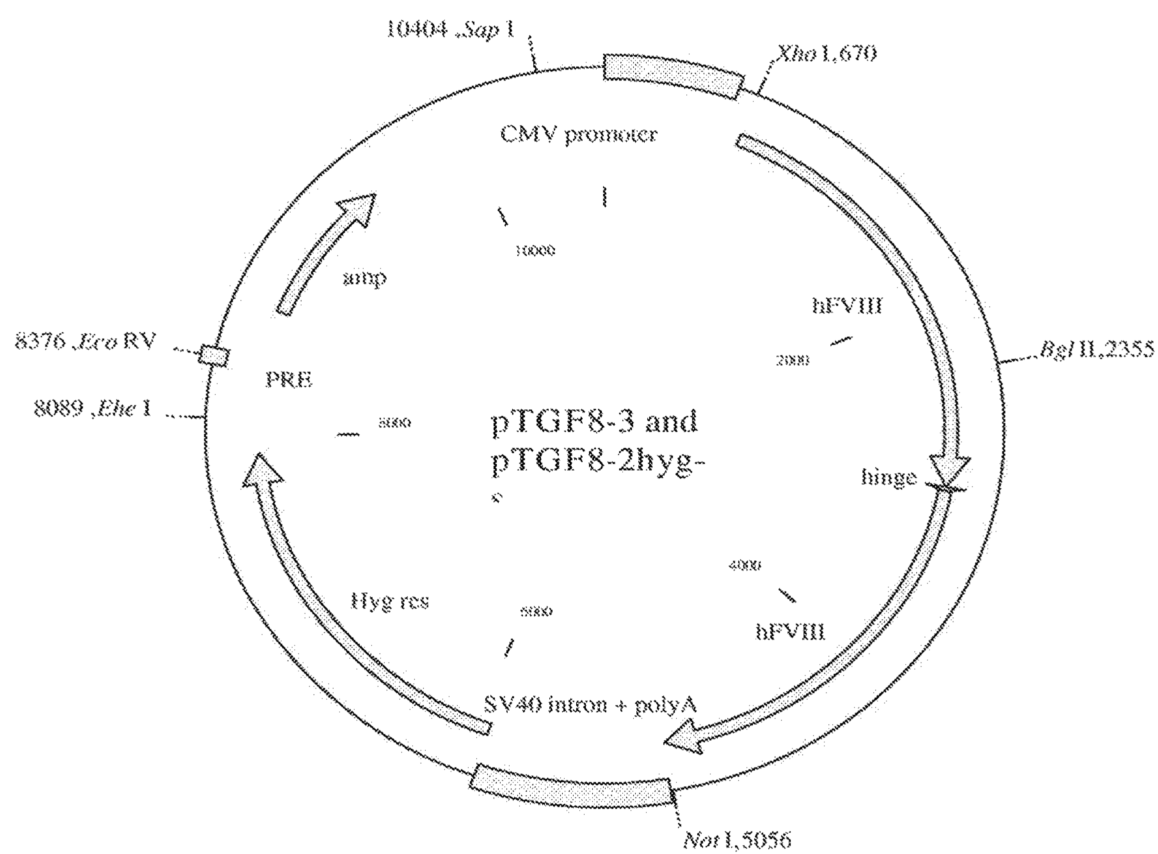
FIG. 4 shows the common molecular structure of pTGF8-3 and pTGF8-2hyg-s, 10698 bps circular DNA, the exact DNA sequences thereof are given in SEQ ID NOs:3 and 5, respectively (for the factor VIII protein encoded by said DNA sequence see SEQ ID NOs:4 and 6, respectively).

Expression Plasmids:

As expression plasmids vectors of the pTGF8 family were used as it can be seen in FIG. 4. The vectors pTGF8-3 and pTGF8-2hyg-s contain the expression cassette for B-domain deleted human clotting factor VIII with the linker peptide of SEQ ID NO:9 (SEQ ID NOs:4 and 6, respectively). pTGF8-2hyg-s further has three amino acid residue exchanges at positions 162, 2011 and 2223 (relative to the full length sequence shown in SEQ ID NO:2). The vectors further contain a cassette for hygromycin resistance (encoding hygromycin-B-phosphotransferase) and a cassette for ampicillin resistance (encoding p-lactamase). Furthermore, a progesterone responsive element (PRE) is contained. The expression of the BDDrFVIII is controlled by a CMV promoter. This promoter in connection with the SV40 intron and the poly-adenylation site provide high level recombinant protein production. The resistance against two antibiotics provides an efficient tool for clone selection after transfection.

Transfection:

Immediately following revitalization of the ECACC stock, adherent 293T cells were transfected with pTGF8-3 or pTGF8-2hyg-s using the calcium phosphate method (C. Chen et al., Mol. Cell Biol. 7(8), 2745-2752 (1987)). Selection with hygromycin (200 ng/ml) started 72 hours after transfection. After 10 days under selection, individual hygromycin-resistant clones were isolated, expanded and subcloned through two consecutive rounds of single cell cloning. Recombinant FVIII production was quantified in the supernatant of hygromycin-resistant clones using ELISA and aPTT assays. This procedure led to the selection of clones no. 293T 48/9 H5 and 293T 12/24E4.

Adaptation to Serum Free Culture Medium:

Clones no. 293T 48/9H5 and 293T 12/24E4 were adapted to growth in serum-free medium over a period of 6 weeks resulting in non-adherent suspension growing cells. After the adaptation process, the cells where expanded using spinner flasks. From these cells, a pre-MCB was established by freezing them in serum-free cryopreservation medium containing 7.5% DMSO. The cryovials, each containing $1\text{-}10^7$ cells, were stored in liquid nitrogen. GMP compliant testing of this pre-MCB concerning in-vitro virus assays, mycoplasma- and sterility-testing was carried out.

Cultivation:

Static cultivation of cells was done in TC-flasks of different size. Bottles and 10 l disposable bioreactors were used for dynamic cultivation. For agitation purpose the bottles where placed on a horizontal shaker situated within the incubator. All incubators were set to 5% carbon dioxide, 37° C. and 95% relative humidity.

Cell Suspension:

(Hereinafter shortly referred to as "CS".) As can be seen in the following examples, cell suspensions used for different experiments exert different amounts of FVIII and host cell proteins. This reflects that the initial material has been taken out at different times in the production cycle (see FIG. 1) and thus some CS have faced more optimal production conditions than others.

Example 2: FVIII Release Using Different Concentration of NaCl and Lysine as Releasing Substances 5 ml of CS1 ($1.6\times10^6$ cells/ml, clone HEK 293T 48/9H5, vector pTGF8-3)) was added to 5 ml of a release solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analyzed for FVIII:C, etc. For a general schematic description of the experiment, see also FIG. 2. The release composition added and the corresponding results are shown in Tables 1 and 2, respectively.

TABLE 1

| Release component | Buffer substances |
|---|---|
| Reference (CS1) | No addition |
| 0.10M NaCl | 20 mM MES, 10 mM CaCl2, 0.01% Tween ® 80, pH 6.5 |
| 0.50M NaCl | 20 mM Histidine, pH 6.0 |
| 1.0M NaCl | 20 mM Histidine, pH 6.0 |
| 2.0M NaCl | 20 mM Histidine, pH 6.0 |
| 1.0M Lysine | 0.10M NaCl, 20 mM MES, 10 mM $CaCl_2$, 0.01% Tween ® 80, pH 7.5 |

TABLE 2

| Release conc.* | FVIII:C, (IU/ml) | Recovery (%) | FVIII:C × $10^{-6}$/cell (IU) | Proteases** (a.u.) |
|---|---|---|---|---|
| Reference | 1.7 | 100 | 1.2 | <1 |
| 0.10M NaCl | 7.0 | 412 | 4.6 | <1 |
| 0.30M NaCl | 8.0 | 470 | 5.4 | 14 |
| 0.55M NaCl | 33.2 | 1953 | 22.2 | 19 |
| 1.0M NaCl | 36.4 | 2141 | 24.2 | 19 |
| 0.50M lysine | 31.8 | 1871 | 21.2 | <1 |

*The final release concentration is half of the added release solution due to the mixing with the CS. The conductivity in the CS is calculated to correspond to about 0.1M NaCl.

**Definition of protease activity: 1 arbitary unit (a.u.) of protease activity is defined as the activity corresponding to the activity of 1 μg of trypsin/l.

Conclusion:

Increase of sodium chloride or lysine concentration before the harvest significant increase the recovered FVIII.

Example 3

5 ml of CS2 ($2.84\times10^6$ cells/ml, clone HEK 293T 12/24E4, vector pTGF8-2hyg-s)) was added to 5 ml of a releasing solution. The cells had been cultivated as described in Example 1 and were withdrawn before harvest (see FIG. 1). The suspension was gently mixed (using a wave mixer) for 1 h at room temperature (21° C.) using 15 ml tubes. The tubes were then centrifuged at 1200×g for 1 minute to remove the cells, where after the cell supernatant was analyzed (FVIII:C, FVIII:Ag, cell viability and total protein). For a schematic description of the experiment, see also FIG. 2. Examples 3A-3C are experiments performed with the same cell suspension in parallel experiments and are thus directly comparable to each other.

Example 3A: Release with Different Concentration of Sodium Chloride

Different concentrations of NaCl were prepared and added to CS2 according to the above-described procedure, to study in which range of sodium chloride concentration the release of FVIII occurs. The results are summarized in Table 3.

TABLE 3

| Release conc.* | FVIII: C (IU/ml) ** | FVIII: C (%) | FVIII: C × $10^{-6}$/cell (IU) | Cell Viability (%) | Purity FVIII (IU/μg prot.) | ratio FVIII: C/ FVIII: ag |
|---|---|---|---|---|---|---|
| Ref.(CS2) | 0.50 | 100 | 0.36 | 36 | 3.4 | 0.57 |
| 0.10M NaCl | 1.42 | 248 | 0.90 | 40 | 4.6 | NA |
| 0.15M NaCl | 1.28 | 256 | 0.94 | 44 | 5.2 | NA |
| 0.25M NaCl | 2.00 | 400 | 1.46 | 50 | 7.7 | NA |
| 0.45M NaCl | 3.56 | 712 | 5.20 | 48 | 26.6 | NA |
| 0.55M NaCl | 4.16 | 832 | 6.08 | 36 | 28.1 | 0.62 |
| 1.0M NaCl | 4.28 | 856 | 6.28 | 8 | 17.8 | 0.50 |
| 2.0M NaCl | 4.42 | 884 | 6.46 | 3 | 15.7 | 0.60 |

*The final wash concentration and the conductivity in the CS are calculated to correspond to about 0.1M NaCl.

** FVIII: C concentration compensated for dilution factors.

NA: not analysed.

Conclusion:

Increased sodium chloride concentration increases the FVIII:C and a plateau is reached at 0.55 M NaCl. The release of FVIII is to a smaller degree achieved by a dilution effect (CS compared with 0.1 M NaCl in table 3). The cell membrane is destroyed if the sodium chloride concentration is increased too much (1.05 M and 2.00 M), whereas the cell viability seems to be approximately unchanged in the interval of 0.1-0.55 M NaCl. The purity of released FVIII reaches a maximum in the 0.45 and 0.55 M NaCl samples, whereas it decreases at the higher salt concentrations due to the release of intracellular host cell proteins caused by cell membrane destruction and/or release of proteins located on the membrane/membrane fragments. Thus, an optimal choice of conditions is to use the highest sodium chloride concentration, which does not destroy the cell membrane. The quotient FVIII:C/FVIII:ag indicates an unchanged biological activity of the released FVIII molecules. The results indicate that the main part of FVIII that is released during the increase of the sodium chloride concentration, mainly is located outside the cell, bound through ionic interactions on the cell surface. This is based on the fact that FVIII recovery does not significantly increase when the cell membrane is disrupted.

Example 3B: Study of Different pH within Different NaCl Concentrations

The pH was adjusted in the range of 6.0-7.5 (pH range in which FVIII is known to be stable) both in the CS2 (0.1 M NaCl) and in the CS2 diluted with the wash substance (final concentration 0.55 M NaCl). To study how different pH affects the release of FVIII. The results are summarized in Table 4.

TABLE 4

| Release concentration* | pH | FVIII:C (IU/ml)** | FVIII:C (%) |
|---|---|---|---|
| CS2 (0.10M NaCl) | 6.0 | 0.46 | 92 |
| CS2 (0.10M NaCl) | 6.5 | 0.50 | 100 |
| CS2 (0.10M NaCl) | 7.2 | 0.50 | 100 |
| CS2 (0.10M NaCl) | 7.5 | 0.53 | 106 |
| 0.55M NaCl | 6.0 | 4.10 | 820 |
| 0.55M NaCl | 6.5 | 4.34 | 868 |
| 0.55M NaCl | 7.0 | 4.30 | 860 |
| 0.55M NaCl | 7.5 | 3.56 | 712 |

*The conductivity in the CS is calculated to correspond to about 0.1M NaCl.

**FVIII:C concentration compensated for dilution factor.

Conclusion:

The pH has no significant effect of the release of FVIII within the pH interval tested (which was selected due to the pH stability of the FVIII molecule). The major difference in FVIII recovery between high (0.55 M NaCl) and low (0.1 M NaCl) of release concentration is independent of pH. The FVIII pH stability (pH 6-7) is discussed at p. 10 of Wang et al., International Journal of Pharmaceutics 259, 1-15 (2003).

Example 3C: Different Concentration of Lysine as a Release Component

Different concentrations of lysine was prepared and added to CS2 according to the above described procedure, to study in which range of lysine concentration the release of FVIII occurs. The results are summarized in Table 5.

TABLE 5

| Release conc.* | FVIII: C, (IU/ml) ** | FVIII: C (%) | FVIII: C × $10^{-6}$/cell (IU) | Cell Viability (%) | Purity FVIII (IU/μg prot.) | Ratio FVIII: C/ FVIII: ag |
|---|---|---|---|---|---|---|
| Ref. (CS2) | 0.50 | 100 | 0.36 | 36 | 3.4 | 0.57 |
| 0.15M lysine | 0.82 | 164 | 0.58 | 33 | 5.9 | 0.53 |
| 0.30M lysine | 1.37 | 274 | 0.96 | 40 | 9.4 | 0.39 |
| 0.5M lysine | 2.88 | 576 | 2.03 | 19 | 16.7 | 0.42 |

*The final release concentration, the conductivity in the CS is calculated to correspond to about 0.1M NaCl.

** FVIII: C concentration compensated for dilution factor.

Conclusion:

Lysine, a charged amino acid, releases FVIII. However, sodium chloride (Example 3A) seems to be a more effective and lenient releaser of FVIII, when compared at similar concentrations. It seems that the cells are more damaged by lysine than sodium chloride, as can be seen when comparing viability, purity and quotient FVIII:C/FVIII:ag.

Example 4: Study of Kinetic and Different Releasing Substances 5 ml of CS3 ($1.6 \times 10^6$ cells/ml, clone HEK 293T 48/9H5, vector pTGF8-3)) was added to 5 ml of a releasing solution. The cells had been cultivated as described in Example 1 and were withdrawn during the growth phase (C in FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C, etc. For a general schematic description of the experiment, see also FIG. 2. Examples 4A-4E are experiments performed with the same CS in parallel experiments and are thus directly comparable to each other.

Example 4A: Study of Time Needed for Release of FVIII Using 0.55 M NaCl

A release solution of 0.10 M and 1.0 M of sodium chloride was prepared and added to CS3 according to the above-described procedure. Samples were withdrawn after 0, 5, 10, 20, 40 and 60 minutes to study how fast FVIII was released. The results are summarized in Table 6.

TABLE 6

| Release concentration* | Time (minutes) | FVIII:C,** (IU/ml) | FVIII:C (%) | FVIII:C × $10^{-6}$/cell (IU) |
|---|---|---|---|---|
| 0.10M NaCl | 60 | 0.12 | 100 | 0.08 |
| 0.55M NaCl | 0 | 1.26 | 1050 | 0.79 |
| 0.55M NaCl | 5 | 1.30 | 1083 | 0.81 |
| 0.55M NaCl | 10 | 1.36 | 1133 | 0.85 |
| 0.55M NaCl | 20 | 1.26 | 1050 | 0.79 |
| 0.55M NaCl | 40 | 1.34 | 1117 | 0.84 |
| 0.55M NaCl | 60 | 1.26 | 1050 | 0.79 |

*The final release concentration, the conductivity of the CS is calculated to correspond to about 0.1M NaCl.
**FVIII:C concentration compensated for dilution factors.

Conclusion:

The increased salt concentration releases the FVIII molecules instantly. The incubation time has no effect on the recovery. This is an important finding that broadens the possible use of the invention, making it possible to use different techniques (dead end filtration, tangential filtration, centrifugation, etc.) to separate the FVIII molecule from the cell using the release procedure. A very interesting approach would be to add—during a perfusion batch (perfusion means normally a slowly continuously harvested cell suspension, where the cells can be used for months to produce the product)—the release buffer with increased ionic concentration, remove the release buffer and thereafter add the cultivation buffer and continue to use the cells to produce FVIII. Due to this procedure, the productivity of the cells can significantly be increased, compared to the normal procedure where either the cells are discarded (destroyed) after the harvest (it takes 1-2 weeks to cultivate new cells up to desired cell concentration) or use the normal slow perfusion harvest with low ionic content and the lower recovery.

Example 4B: Study of Release Composition Using Different NaCl Concentration

Different concentrations of NaCl were prepared and added to CS3 according to the above-described procedure, to study in which range of sodium chloride concentration the release of FVIII occurs. The results are summarized in Table 7 (see also example 3A for a similar NaCl study with another CS and additional analyses performed).

TABLE 7

| Release concentration* | FVIII:C** (IU/ml) | FVIII:C (%) | FVIII:C × $10^{-6}$/cell (IU) | Viability (%) |
|---|---|---|---|---|
| 0.10M NaCl | 0.12 | 100 | 0.08 | 89 |
| 0.30M NaCl | 0.76 | 633 | 0.48 | 92 |
| 0.40M NaCl | 1.03 | 858 | 0.64 | 93 |
| 0.50M NaCl | 0.98 | 817 | 0.61 | 90 |
| 0.55M NaCl | 1.26 | 1050 | 0.79 | NA |
| 0.60M NaCl | 1.10 | 917 | 0.69 | 88 |

*The final release concentration, the conductivity in the CS is calculated to correspond to about 0.1M NaCl.
**FVIII:C concentration compensated for dilution factors.
NA: not analysed.

Conclusion:

The FVIII release starts at about 0.30 M NaCl and reaches a peak at about 0.55 M NaCl. There is no significant difference in cell viability, within the NaCl concentration tested.

Example 4C: Study of Lysine as a Release Substance Compared with NaCl

Different concentrations of lysine was prepared (pH was adjusted to 7.0) and added to CS3 according to the above described procedure, to study at which level the maximum release of FVIII occurred compared with sodium chloride as releasing substance. The results are summarized in Table 8.

TABLE 8

| Wash concentration* | FVIII:C,** (IU/ml) | FVIII:C (%) | FVIII:C × $10^{-6}$/cell (IU) |
|---|---|---|---|
| 0.10M NaCl | 0.12 | 100 | 0.08 |
| 0.55M NaCl | 1.26 | 1050 | 0.79 |
| 0.50M lysine | 1.08 | 900 | 0.68 |
| 0.75M lysine | 1.24 | 1033 | 0.78 |
| 1.0M lysine | 1.22 | 1017 | 0.76 |

*The final release concentration, the conductivity of the CS is calculated to correspond to about 0.1M NaCl.
**FVIII:C concentration compensated for dilution factors Conclusion:

Lysine can be used as a release substance with the same degree of total FVIII release compared with sodium chloride. It seems that sodium chloride is a little bit more effective to release FVIII in regard of concentration (M) needed to achieve the same recovery.

Example 4D: Study of Different Types of Potential Release Compositions

Different buffers was prepared (pH was adjusted to 7.0 if applicable) and added to CS3 according to the above described procedure, to study if release of FVIII occurred. The results are summarized in Table 9.

TABLE 9

| Buffer concentration* | FVIII:C,** (IU/ml) | FVIII:C (%) | FVIII:C × $10^{-6}$/cell (IU) | Viability (%) |
|---|---|---|---|---|
| 0.10M NaCl | 0.12 | 100 | 0.08 | NA |
| 0.55M NaCl | 1.26 | 1050 | 0.79 | NA |
| 0.50M lysine | 1.08 | 900 | 0.68 | NA |
| 0.50M arginine | 0.48 | 400 | 0.30 | NA |
| 0.25M histidine | 0.54 | 450 | 0.34 | NA |
| 0.50M glycine | <0.1 | <90 | <0.08 | NA |
| 0.50M KCl | 1.64 | 1367 | 1.02 | NA |
| 0.50M ammonium acetate | 0.92 | 767 | 0.58 | NA |
| 0.50M $MgCl_2$ | 1.30 | 1083 | 0.81 | NA |
| 0.50M sorbitol | <0.1 | <90 | <0.08 | 90 |
| 1% Triton ® X-100 | 0.86 | 716 | 0.54 | 0 |

*The conductivity in the CS is calculated to correspond to about 0.1M NaCl.
**FVIII:C concentration compensated for dilution factors.
NA: not analysed.

Conclusion:

As already has been shown in previous examples, sodium chloride and lysine can be used as release substances with about the same degree of FVIII release. As shown in this example a lot of charged substances can achieve similar effects but not all, to the same level. When some charged amino acids was compared with each other, lysine was a more effective releasing agent of FVIII compared with arginine and histidine (however due to low solubility histidine concentration could only be raised to 0.25 M). A very interesting observation was that an amino acid with uncharged R-group (glycine) and a sugar (sorbitol) did not release FVIII at all. This gives a clear indication that the main force that retains the FVIII molecule is of ionic origin. The detergent, 1% Triton® x-100, which is known in the prior art to disrupt the cell membrane and release all proteins that have been inside the cells, was included in the experiment to study to which degree FVIII was trapped inside the cell. When studying the cells before and after the treatment with detergent, no cells or traces of cells could be seen after the detergent treatment, thus all cell material has been dissolved. The FVIII concentration in the sample, which had been detergent treated, was in principle the same as for the highest 0.50 M values (with the main part of the cells intact after treatment). This indicates that when using the releasing procedure, the main part of the released FVIII is originating from binding to cells surfaces outside the cell, this theory is also strengthen by the instant release of FVIII when using the washing procedure (example 4A).

Example 4E: Study of Combination of Releasing Substances

Different buffers were prepared in which different release substances were mixed (pH was adjusted to 7.0 if applicable) and added to CS3 according to the above described procedure, to study if the recovery of FVIII was changed compared to when using only one releasing substance. The results are summarized in Table 10.

TABLE 10

| Release concentration* | FVIII:C,** (IU/ml) | FVIII:C (%) | FVIII:C × $10^{-6}$/ cel (IU) | Viabilty (%) |
|---|---|---|---|---|
| 0.10M NaCl | 0.12 | 100 | 0.08 | 89 |
| 0.30M NaCl | 0.76 | 633 | 0.48 | 92 |
| 0.60M NaCl | 1.26 | 1050 | 0.79 | 88 |
| 0.50M lysine | 1.08 | 900 | 0.68 | NA |
| 1% Triton ® X-100 | 0.86 | 716 | 0.54 | 0 |
| 0.60M NaCl + 1% Triton ® | 0.92 | 766 | 0.57 | 0 |
| 0.25M NaCl + 0.25M lysine | 1.12 | 933 | 0.70 | NA |
| 0.17M NaCl + 0.17M lysine + 0.33M sorbitol | 0.94 | 783 | 0.59 | NA |

*The conductivity in the CS is calculated to correspond to about 0.1M NaCl.
**FVIII:C concentration compensated for dilution factors.
NA: not analysed.

Conclusion:

Different release substances can be combined to release the FVIII molecule.

Example 5: Study of Different Charged Substances as Releasing Agent 5 ml of CS4 ($6.37\times10^6$ cells/ml, clone HEK 293T 48/9H5, vector pTGF8-3)) was added to 5 ml of a releasing solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C, etc. For a general schematic description of the experiment, see also FIG. 2. Examples 5A-5D are experiments performed with the same CS batch in parallel experiments and are thus directly comparable to each other.

Example 5A: Study of Different Concentrations of KCl as Release Composition and Compared with NaCl Different concentrations of KCl were prepared and added to CS4 according to the above described procedure, to study in which range of sodium chloride concentration the release of FVIII occurs and to compare it with NaCl. The results are summarized in Table 11.

TABLE 11

| Release conc.* | FVIII: C, (IU/ml) | FVIII: C (%) | FVIII: C × $10^{-6}$/cell (IU) | Cell viability (%) | Purity FVIII, IU/μg prot. | Proteases** (a.u) |
|---|---|---|---|---|---|---|
| 0.10M KCl | 0.26 | 100 | 0.08 | 87 | NA | 82 |
| 0.15M KCl | 0.64 | 260 | 0.20 | 85 | NA | NA |
| 0.20M KCl | 1.21 | 480 | 0.38 | 86 | NA | NA |
| 0.25M KCl | 2.30 | 920 | 0.72 | 82 | NA | NA |
| 0.38M KCl | 4.47 | 1790 | 1.40 | 64 | NA | NA |
| 0.50M KCl | 4.42 | 1770 | 1.39 | 70 | 0.32 | 60 |

TABLE 11-continued

| Release conc.* | FVIII: C, (IU/ml) | FVIII: C (%) | FVIII: C × $10^{-6}$/cell (IU) | Cell viability (%) | Purity FVIII, IU/μg prot. | Proteases** (a.u) |
|---|---|---|---|---|---|---|
| 1.0M KCl | 5.08 | 2030 | 1.60 | 30 | 0.13 | 92 |
| 0.10M NaCl | 0.25 | 96 | 0.08 | 85 | 0.03 | 82 |
| 0.55M NaCl | 4.96 | 1980 | 1.56 | 80 | 0.35 | 73 |

*The final release concentration, the conductivity in the CS is calculated to correspond to about 0.1M NaCl.

NA: not analysed.

**Definition of protease activity: 1 arbitary unit of protease activity is defined as the activity corresponding to the activity of 1 μg of trypsin/l.

Conclusion:

The ability for different KCl concentrations to release FVIII is comparable with NaCl. Also the cell viability, purity and protease release are almost the same compared with those of NaCl. However, there is a small trend that maybe NaCl is milder against the cells, when comparing the cell viability and the purity within similar concentrations. A decreased purity is an indication of cell damage as can be seen for the 1 M KCl wash solution, in which the purity has significantly decreased, indicating in combination with the decreased cell viability, that host cell proteins have been released due to lysis of the cell membrane.

Example 5B: Study of Different Charged Release Compositions

Different release compositions were prepared (pH was adjusted to 7.0 if applicable) and added to CS4 according to the above described procedure, to study if release of FVIII occurred. The results are summarized in Table 12.

TABLE 12

| Release conc.* | FVIII: C, (IU/ml) | FVIII: C (%) | FVIII: C × $10^{-6}$/cell (IU) | Cell viability (%) | Purity FVIII, IU/μg prot. | Proteases*** (a.u) |
|---|---|---|---|---|---|---|
| 0.10M NaCl | 0.25 | 100 | 0.08 | 85 | 0.03 | 82 |
| 0.55M NaCl | 4.96 | 1980 | 1.56 | 80 | 0.35 | 73 |
| 0.50M KCl | 4.42 | 1768 | 1.39 | 70 | 0.32 | 60 |
| 0.50M $Na_2SO_4$ | 3.21 | 1284 | 1.01 | 34 | NA | 109 |
| 0.50M $KH_2PO_4$ | 3.62 | 1448 | 1.14 | 44 | NA | 94 |
| 0.25M $CaCl_2$ | 5.34 | 2136 | 1.68 | 78** | 0.53 | NA |
| 0.50M $MgCl_2$ | 2.26 | 904 | 0.71 | 16** | NA | NA |
| 0.75M lysine | 6.10 | 2440 | 1.92 | 75 | 0.20 | 113 |

*The final release concentration, the conductivity in the CS is calculated to correspond to about 0.1M NaCl.

**Difficulties within analysis as washing substance was precipitated when analytical chemical was added, during measurement.

***Definition of protease activity: 1 arbitary unit of protease activity is defined as the activity corresponding to the activity of 1 ug of trypsin/L.

NA: not analysed.

Conclusion:

Different charged substances can be used to release FVIII (as also shown in example 3D). However, as shown in some of the previous examples, it is preferable to choose a release substance which not destroys the cell membrane, as this releases host cell proteins and proteases which decrease the purity and can decrease the stability of the of the product. In addition, if the cells are destroyed, they cannot be used for continuous production of the product, which decrease the overall yield. It can be noted that 0.55 M NaCl, 0.50 M KCl and 0.25 M $CaCl_2$ all gives a very high recovery with almost unchanged cell viability and with a high purity of released product.

Example 6: Study of Calcium Chloride as Release Composition and Comparison with NaCl 5 ml of a CS5 ($3.47\times10^{-6}$ cells/ml, clone HEK 293T 48/9H5, vector pTGF8-3)) was added to 5 ml of a release solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C, etc. For a general schematic description of the experiment, see also FIG. 2. Examples 6A-6E are experiments performed with the same CS batch in parallel experiments and are thus directly comparable to each other.

A: Study of Different Concentrations of $CaCl_2$ as Release Composition and Compared with NaCl Different concentrations of $CaCl_2$ were prepared and added to CS5 according to the above-described procedure, to study in which range of calcium chloride concentration the release of FVIII occurs. The results are summarized in Table 13.

TABLE 13

| Release concentration* | FVIII:C, (IU/ml) | FVIII:C (%) | FVIII:C × $10^{-6}$/cell (IU) | Cell Viability (%) | Purity FVIII, IU/μg prot. |
|---|---|---|---|---|---|
| 0.10M NaCl | 5.06 | 100 | 2.92 | 94 | 0.22 |
| 0.55M NaCl | 13.6 | 269 | 7.86 | 82 | 1.05 |
| 0.05M $CaCl_2$ | 15.1 | 298 | 8.73 | 71** | 2.16 |

TABLE 13-continued

| Release concentration* | FVIII:C, (IU/ml) | FVIII:C (%) | FVIII:C × $10^{-6}$/cell (IU) | Cell Viability (%) | Purity FVIII, IU/μg prot. |
|---|---|---|---|---|---|
| 0.10M $CaCl_2$ | 18.0 | 356 | 10.4 | 77** | 1.80 |
| 0.20M $CaCl_2$ | 7.32 | 145 | 4.23 | 52** | 0.46 |

*The final release concentration, the conductivity in the CS is calculated to correspond to about 0.1M NaCl.
**uncertain results as $CaCl_2$ precipitates during the adding of analytical reagents.

Figures 3A, 3B:
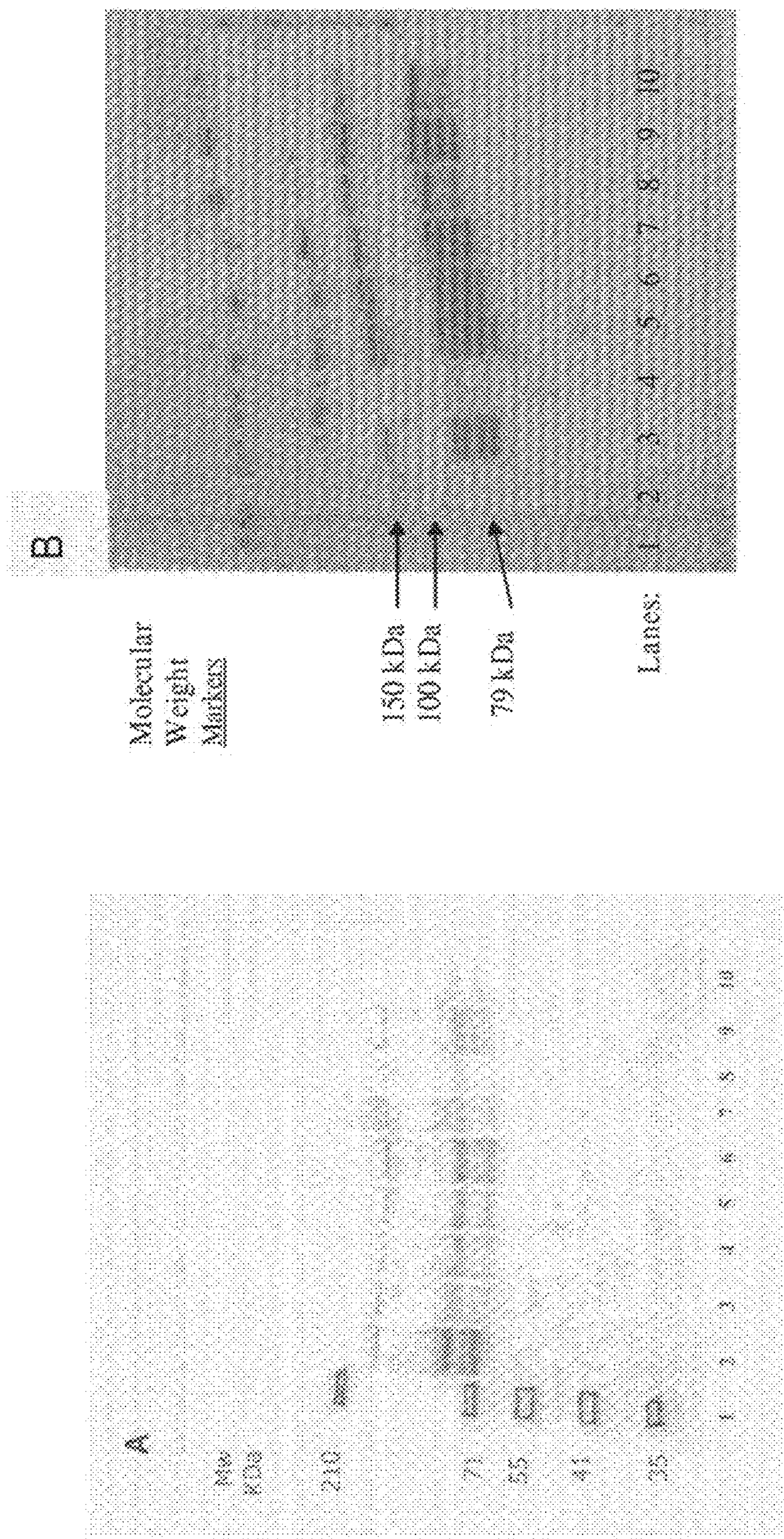
FIGS. 3A-3B show Western Blot analysis of crude research material harvested with different release compositions (FIG. 3A lanes 3 to 6, FIG. 3B lanes 2 to 8) which is compared with molecular markers (FIGS. 3A and 3B lane 1, respectively) and high purified FVIII product FIG. 3A lane 2).

Conclusion:

Calcium chloride can be used as an effective releaser of FVIII in the cell harvest procedure. A 10 fold lower concentration of calcium chloride (0.05 M) has the same releasing effect as compared to the higher sodium chloride concentration (0.55 M). In additional the calcium chloride wash seems to release significant lower amounts of other host cell proteins, resulting in that the purity of released FVIII significantly increased compared to that of using sodium chloride. The cell viability of the cells treated with calcium chloride seems to be slightly lower compared to the sodium chloride wash, this is however uncertain because of influence of Ca to the viability measurement method. Cell aggregation and not lysis of the cells, is a possible explanation strengthen by the still low amount of host cells proteins released (it is known that calcium chloride can induce aggregation within cells). The western blot analysis indicates that there is no significant difference in molecular mass pattern of the crude FVIII, released with 0.10M NaCl, 0.55M NaCl, 0.10 M $CaCl_2$ and 0.20M $CaCl_2$ (FIGS. 3A and 3B) and compared with a highly purified FVIII preparation (FIG. 3A).

B: Study of Cell Cultivation Media Added with Different Amounts of $CaCl_2$ as Release Composition.

Unused cell cultivation medium (the same as used during cell cultivation, Freestyle) was used as buffer solution. The cell cultivation media (CCM) was added to different amounts of $CaCl_2$, in order to study the FVIII release. The results are summarized in Table 14.

TABLE 14

| Release composition* | FVIII:C, (IU/ml) | FVIII:C (%) | FVIII:C × $10^6$/cell (IU) | Cell Viability (%) |
|---|---|---|---|---|
| Reference, 0.10M NaCl | 5.06 | 100 | 2.92 | 94 |
| CC M + 0.005M $CaCl_2$ | 9.72 | 192% | 5.60 | 91% |
| CC M + 0.01M $CaCl_2$ | 9.12 | 180% | 5.26 | 70% |

*The final release concentration, the conductivity in the CS is calculated to correspond to about 0.1M NaCl.

Conclusion:

A small increase (5-10 mM) in the calcium chloride concentration in the CCM, significantly increases the FVIII release.

Example 7: Study of Different Substances of Non-Charged Origin and Compared with NaCl as Release Composition 5 ml of a CS6 ($2.96\times10^6$ cells/ml, clone HEK 293T 12/24E4, vector pTGF8-2hyg-s)) was added to 5 ml of a release solution. The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C activity, etc. For a general schematic description of the experiment, see also FIG. 2. Examples 7A-7B are experiments performed with the same CS batch in parallel experiments and are thus directly comparable to each other.

A: Study of Different (Uncharged) Substances and Compared with NaCl as Release Composition.

Different solutions were prepared and added to CS6 according to the above-described procedure, to study if FVIII release occurs with substances working with different principles (non-ionic). The results are summarized in Table 15.

TABLE 15

| Release composition* | FVIII:C (IU/ml) | FVIII:C (%) | FVIII:C × $10^{-6}$/cell (IU) | Cell Viability (%) |
|---|---|---|---|---|
| 0.10M NaCl | 0.21 | 100 | 0.14 | 59 |
| 0.55M NaCl | 0.96 | 457 | 0.65 | 54 |
| 10% polyethylene glycol 4000 | 0.12 | 57 | 0.08 | 75 |
| 5% ethylene glycol | 0.20 | 95 | 0.14 | 50 |
| 10% ethylene glycol | <0.1 | <50 | <0.07 | 26 |
| 0.5M alanine | 0.18 | 86 | 0.12 | 62 |
| 0.25M valine | 0.25 | 119 | 0.17 | 68 |
| 10% ethanol | 0.11 | 52 | 0.07 | 32 |
| 5% sodium caprylate | <0.1 | <50 | <0.07 | Na |

*The final release concentration, the conductivity in the CS is calculated to correspond to about 0.1M NaCl.

Conclusion:

Different substances of non-ionic origin (hydrophilic, hydrophobic, alcohols) have been tested and the results have been compared with sodium chloride as release substance. The result shows that release substances of ionic nature are needed for the release of FVIII.

B: 0.55 M NaCl as Release Substance, Concentration and Analysis with Western Blot.

50 ml of CS6 was added to 50 ml of a 1 M NaCl solution. The mixture was gently rocked for 1 hour in room temperature, where after the solution was centrifuged 5 minutes (1200×g) and the supernatant was recovered. The cell supernatant was there after concentrated to a FVIII:C content of 13.6 IU/ml, using centrifugation containers including a 10 kDa membrane (Amicon, centriprep).

The centrifugation was necessary to be able to use the Western blot analytical method 1 as a tool, to increase the FVIII concentration.

Conclusion:

The molecular mass distribution of the crude FVIII released with 0.55M NaCl and compared with a highly purified commercially available FVIII preparation, shows a similar molecular mass distribution (FIG. 3A).

Example 8: Study of Different Concentrations of $CaCl_2$ as a Release Substance and Comparison with High (0.55 M) and Low (0.1 M) NaCl A: 5 ml of CS7 ($3.41\times10^6$ Cells/Ml, Clone HEK 293T 48/9H5, Vector pTGF8-3)) was Added to 5 ml of a Release Composition.

The cells had been cultivated as described in Example 1 and were withdrawn before harvest (see FIG. 1). The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C activity, etc. For a general schematic description of the experiment, see also FIG. 2.

Different concentrations of $CaCl_2$ were prepared and added to CS7 according to the above-described procedure, to study in which range of $CaCl_2$ concentration the release of FVIII occurs. The results are summarized in Table 16.

TABLE 16

| Release concentration* | FVIII:C, (IU/ml) | FVIII:C (%) | FVIII:C × $10^{-6}$/cell (IU) | Cell Viability (%) |
|---|---|---|---|---|
| 0.10M NaCl | 3.65 | 100 | 2.14 | 90 |
| 0.075M $CaCl_2$ | 9.42 | 258 | 5.52 | 73** |
| 0.10M $CaCl_2$ | 10.5 | 288 | 6.16 | 69** |
| 0.125M $CaCl_2$ | 11.7 | 320 | 6.86 | 67** |

*The final wash concentration, the conductivity in the CS is calculated to correspond to about 0.1M NaCl

**uncertain results as $CaCl_2$ precipitates during the adding of analytical reagents.

Conclusion:

$CaCl_2$ is a release substance, which release FVIII at relatively low concentration. The concentration needed is significant lower compared with NaCl.

B: Study of Time Needed for Release of FVIII Using 0.1 M $CaCl_2$.

A release solution of 0.10 M $CaCl_2$ was prepared and added to the cell suspension according to the above described procedure. Samples were withdrawn after 0, 10, 30 and 60 minutes to study how fast FVIII was released. The results are summarized in Table 17.

TABLE 17

| Release concentration* | Time, (minutes) | FVIII: C, (IU/ml) | FVIII: C × $10^{-6}$/cell (IU) |
|---|---|---|---|
| Reference, CS7 | 0 | 3.65 | 2.14 |
| 0.10M $CaCl_2$ | 0 | 9.34 | 5.48 |
| 0.10M $CaCl_2$ | 10 | 10.7 | 6.28 |
| 0.10M $CaCl_2$ | 30 | 10.3 | 6.04 |
| 0.10M $CaCl_2$ | 60 | 10.5 | 6.16 |

*The final release concentration, the conductivity in the CS is calculated to correspond to about 0.1M NaCl.

Conclusion:

The release of FVIII using 0.1 M $CaCl_2$ occurs fast, within minutes the main part of FVIII has been released.

Example 9: Study of Different Concentrations of $CaCl_2$ as Release Composition and Comparison with NaCl 5 ml of a CS8 ($3.1\times10^4$ cells/ml, clone HEK 293T 12/24E4, vector pTGF8-2hyg-s) was added to 5 ml of release composition. The cells had been cultivated as described in Example 1. The suspension was gently mixed (using a rocking mixer) for 1 h at room temperature (21° C.), using 15 ml tubes. The tubes were then centrifuged at 1200×g for 1 minute to remove the cells, where after the cell supernatant was analysed for FVIII:C. For a general schematic description of the experiment, see also FIG. 2. Different concentrations of $CaCl_2$ was prepared and added to the cell suspension according to the above-described procedure to study in which range of calcium chloride concentration the release of FVIII occurs. The results are summarized in Table 18.

TABLE 18

| Release conc.* | FVIII: C, (IU/ml) | FVIII: C (%) | FVIII: C × $10^{-6}$/cell (IU) | Ratio FVIII: C/ FVIII: Ag | Purity FVIII: C/protein, (IU/ug) | DNA/ FVIII (ug/IU) |
|---|---|---|---|---|---|---|
| 0.1M NaCl | 1.48 | 100 | 0.48 | 0.63 | 0.026 | 0.69 |
| 0.55M NaCl | 10.2 | 689 | 3.29 | 0.72 | 0.160 | 0.91 |
| 0.01M $CaCl_2$ | 1.14 | 77 | 0.37 | 0.51 | 0.020 | NA |
| 0.01M $CaCl_2$ + 0.10M NaCl | 2.12 | 143 | 0.68 | 0.56 | 0.050 | NA |
| 0.04M $CaCl_2$ | 3.32 | 224 | 1.07 | NA | 0.072 | NA |
| 0.05M $CaCl_2$ | 4.34 | 293 | 1.40 | 0.75 | 0.094 | NA |
| 0.075M $CaCl_2$ | 7.70 | 520 | 2.48 | 0.93 | 0.226 | NA |
| 0.10M $CaCl_2$ | 9.98 | 674 | 3.22 | 1.11 | 0.293 | 0.09 |
| 0.15M $CaCl_2$ | 10.5 | 707 | 3.39 | 0.98 | 0.327 | NA |
| 0.20M $CaCl_2$ | 10.5 | 707 | 3.39 | NA | NA | NA |

*The conductivity in the CS is calculated to correspond to about 0.1M NaCl.

NA: not analysed

Conclusion:

Calcium chloride can be used as an effective releaser of FVIII. The optimal release condition seems to be about 0.1 M $CaCl_2$. In comparison with NaCl, the $CaCl_2$ release procedure seems to produce a purer harvest with higher quality. The DNA release from the cells is significantly decreased (a factor 10) when using the calcium chloride release method compared with the high (0.55 M) NaCl release method. This is a very interesting feature of calcium chloride, as the removal of DNA in the product is an important issue from a purification point of view when working with recombinant produced pharmaceuticals. The regulatory demand of DNA content in the final product is set very low, to protect unwanted transmissions. Thus a low DNA release harvest procedure is a highly interesting property of the method of the invention.

Example 10 Cultivation in pilot scale, NaCl/$CaCl_2$/His FVIII release, capture step.

9844 g of CS9 (sample 1), $2.4\times10^6$ cells/ml, (clone HEK 293T 48/9H5, vector pTGF8-3)) was filtered through a 0.5 μm profile filter (0.6 $m^2$). The filter (with the removed cells) were then washed with 7.5 L of a solution of 0.55 M NaCl+10 mM $CaCl_2$+10 mM Histidin, pH 7, to release any adhering FVIII. The filtrate and the wash were pooled (sample 2). Before use, the filter had been washed with 12 LI of distilled water and equilibrated with 2 l of a buffer containing 100 mM NaCl+10 mM $CaCl_2$+10 mM histidine pH 7. The filtration was performed with a trans membrane pressure of 0.2 bar. About half of the filtrate (47%) was used for further processing to the capture step (anion chromatography exchanger), the material was diluted to a final conductivity of 13.0 mS/cm at 25° C. before applying it to the capture step. 9317 of the starting material (sample 3) were applied to the capture step after the elution of the capture step with increased ionic strength, 3.8 g of the product was eluted (sample 4). The results are summarized in Table 19.

TABLE 19

| Sample No | (g) | FVIII (IU/ml) | FVIII, total (IU) | Yield total, (%) | Yield each step (%) |
|---|---|---|---|---|---|
| Sample 1 (CS) | 9844 | 0.62 | 6103 | 100 | 100 |
| Sample 2 (cell filtrate) | 12276 | 1.13 | 13845 | 226 | 226 |
| Sample 3 (capture start) | 9317 | 0.68 | 6336 | 226 | 100 |
| Sample 4 (capture eluat) | 318 | 14.0 | 4452 | 146 | 70 |

Conclusion:

The example shows a different way of using the invention; the release substance (0.55 M NaCl) is added after the separation of cells and cell supernatant. The advantage is a lower level of ionic strength in the recovered solution after filtration. The lower ionic strength might be of importance if the solution is to be further purified on a ion-exchange based capture step. A ion-exchanger can not be processed with a to high ionic strength. In that cprotein solution must be diluted, which can have certain practical disadvantages due to large volumes after dilution. Thus the described release procedure minimizes the dilution volume before the capture step. The described procedure in liter scale increased the FVIII recovery about 2 times (compared with untreated c). The cell suspension media could successfully be removed using an anion chromatography exchanger, which also reduced the volume with a factor 29.

Example 11: Cultivation in Liter Scale, $CaCl_2$ Release, Capture Step 7403 g of cell suspension (sample 1 was withdrawn, centrifuged and cell free supernatant was analyzed for FVIII) containing $3\times10^6$ cells/ml, clone and vector will be included by SW was added 370 g of a 1 M $CaCl_2$ solution to a final concentration of 50 mM $CaCl_2$. The solution was stirred for 10 minutes (sample 2 was withdrawn, centrifuged and cell free supernatant was analyzed for FVIII) where after the cells were removed with filtration (0.4 $m^2$, 0.5 μm profile filter). Before use, the filter was washed with 10 l of distilled water and equilibrated with 5 l of a buffer containing 100 mM NaCl+50 mM $CaCl_2$+50 mM histidine pH 7.1. The filtration was performed with a trans membrane pressure of about 0.2 bar. After the cell suspension has been filtered, each filter was washed with 2 l of said equilibration buffer, to recover adsorbed FVIII. The filtrate and the wash was pooled (sample 3, 11856 g) and added Tween® 80 to a final concentration of 0.01% (to avoid protein adsorption during further processing).

Filtrate 1 was filtrated through a 0.2 $m^2$ 0.5 μm/0.2 μm filter to protect the capture resin in the next ion exchange step. Before use, each filter was washed with 5 l of distilled water and equilibrated with 5 l of a buffer containing 100 mM NaCl+50 mM CaCl2+50 mM histidine+0.01% Tween® 80, pH 7.1. The filtration was performed with a trans membrane pressure of 0.5 bar. After that filtrate 1 has been filtered, the filter was washed with 4 l of said equilibration buffer, to recover adsorbed FVIII. The filtrate and the wash were pooled (14286 g, sample 4).

The 0.2 μm filtrate was diluted before applying to the capture step. 28613 g of the starting material (capture start; sample 5) was applied to the capture step, 580 g of the product was eluted (sample 6). The results are summarized in Table 20.

TABLE 20

| Sample No | Weight (g) | FVIII (IU/ml) | FVIII, total (IU) | Yield, total (%) | Yield each step (%) |
|---|---|---|---|---|---|
| Sample 1 (cell susp.) | 7403 | 0.32 | 2369 | 100 | 100 |
| Sample 2 (cell susp. + Ca) | 7773 | 2.8 | 21764 | 919 | 919 |
| Sample 3 (cell filtrate) | 11874 | 1.7 | 20394 | 861 | 94 |
| Sample 4 (0.2 um filtrate) | 14286 | 1.39 | 19905 | 840 | 98 |
| Sample 5 (capture start) | 28613 | 0.61 | 17454 | 737 | 100 |
| Sample 6 (eluat) | 580 | 22.8 | 13224 | 558 | 76 |

Conclusion:

The release procedure of the invention, using a release composition of 50 mM $CaCl_2$, 50 mM histidine and 100 mM NaCl in pilot scale, increased the FVIII recovery with about 9 times compared with untreated CS. The cell suspension media could successfully be removed using an anion chromatography exchanger as a capture step, which reduced the volume with a factor 50.

Example 12: Increase (0.4 M NaCl) and Decrease (0.1 M NaCl) of Salt Content During Cultivation A very important feature of the invention would be if it were possible to use it in cycles during cultivation. This would significant increase the recovery and the productivity of the cell line. Below this idea has been tested with promising results.

A (0.4 M NaCl Cultivation):

To CS11 (1.8 ml) containing $2.8\times10^6$ cells/ml (clone HEK 293T 48/9H5, vector pTGF8-3)), which had been cultivated as described in Example 1, 0.32 ml of 2.1 M NaCl was added (final concentration 0.4 M NaCl). The solution was mixed for 15 minutes, where after the suspension was carefully centrifuged (60×g), the cell supernatant was withdrawn and analysed with regard to FVIII:C, the remaining cells where then dissolved in the cultivation media back to the normal salt content (about 0.1 M NaCl). The cell suspension was allowed to grow for 3 days, where after the above procedure was repeated again, with the exception that the salt treatment duration was 2.5 h. Again the NaCl concentration was decreased due to dilution with cultivation medium to about 0.1 M. The cell suspension was again allowed to grow, this time for 4 days. Cell concentration and FVIII:C was followed during the experiment B (0.1 M NaCl Cultivation):

The experiment was performed as in A, with the exception that no NaCl was added. Thus the NaCl concentration was about 0.1 M as present in the cultivation media. The results are summarized in Table 21.

TABLE 21

| Sample | Time (hour) | Cell conc. ($10^6$) | FVIII: C (IU/ml) |
|---|---|---|---|
| A CS 0.4M | 0 | 2.8 | 1.4 |
| B CS 0.1M | 0 | 2.8 | 0.3 |
| A CS 0.4M | 20 | 0.1 | NA |
| B CS 0.1M | 20 | 0.2 | 0.53 |
| A CS 0.4M | 70 | 0.8 | 0.24 |
| B CS 0.1M | 70 | 0.9 | NA |
| A CS 0.4M | 90 | 0.3 | NA |
| B CS 0.1M | 90 | 0.4 | NA |
| A CS 0.4M | 110 | 0.5 | NA |
| B CS 0.1M | 110 | 1.1 | NA |
| A CS 0.4M | 145 | 1.0 | NA |
| B CS 0.1M | 145 | 1.3 | NA |
| A CS 0.4M | 165 | 2.2 | NA |
| B CS 0.1M | 165 | 2.7 | NA |

NA: not analysed.

Conclusion:

The results show that the cells which has been treated with short pulses of 0.4 M NaCl, seems to initially grow a little bit slower. However, after 165 hours there is no significant difference between the high salt treatment and the reference. In conclusion, to use short periods of increased salt concentrations according to the invention, seems to be an interesting possibility.

Example 13: Production Scale, $CaCl_2$/Histidine/NaCl FVIII Release Composition Capture Step 150 kg CS12 (sample 1 was withdrawn, centrifuged and cell free supernatant was analyzed for FVIII) containing $0.8\times10^6$ cells/ml, (clone HEK 293T 48/9H5, vector pTGF8-3) was added 16.7 kg of a 0.5 M $CaCl_2$ solution, to a final concentration of 50 mM $CaCl_2$. The solution was stirred for 15 minutes (sample 2 was withdrawn, centrifuged and cell free supernatant was analyzed for FVIII) where after the cells were removed with filtration (7 $m^2$, 0.5 μm profile filter). Before use, the filters had been washed with 400 l of distilled water and equilibrated with 300 l of a buffer containing 100 mM NaCl+50 mM $CaCl_2$+50 mM histidine pH 7.1. The filtration was performed with a trans membrane pressure of about 0.2 bar. After the cell suspension has been filtered the filters were washed with 2×100 l of said equilibration buffer, to recover adsorbed FVIII. The filtrate and the wash were pooled (sample 3, 359 kg). and added Tween® 80 to a final concentration of 0.01% (to avoid protein adsorption during further processing).

The Tween® added filtrate (sample 3) was filtrated through a 0.6 $m^2$ 0.5 μm/0.2 pm filter to protect the capture step. Before use, the filter was washed with 50 l of distilled water and equilibrated with 50 l of a buffer containing 100 mM NaCl+50 mM $CaCl_2$+50 mM histidine+0.01% Tween® 80, pH 7.1. The filtration was performed with a trans membrane pressure of about 0.5 bar. The filter was washed with 30 l of equilibration buffer, to recover adsorbed FVIII. The filtrate and the wash was pooled (38 kg, sample 5).

The 0.2 μm filtrate was diluted before applying to the capture step 774 kg of the starting material (capture start, sample 5) were applied to the capture anion exchanger 4.68 kg was eluted (sample 6). The results are summarized in Table 22.

TABLE 22

| Sample No | Weight (kg) | FVIII: C IU/ml) | FVIII, total (kIU) | Yield total, (%) | Yield each step (%) |
|---|---|---|---|---|---|
| Sample 1 (cell susp.) | 150 | 0.75 | 112 | 100 | 100 |
| Sample 2 (cell susp. + Ca) | 168 | 5.1 | 857 | 765 | 765 |
| Sample 3 (cell filtrate) | 359 | 2.9 | 1041 | 929 | 929<br>100 |
| Sample 4 (0.2 μm filtrate) | 384 | 2.8 | 1075 | 960 | 97<br>100 |
| Sample 5 (capture start) | 774 | 1.3 | 1006 | 898 | 94<br>100 |
| Sample 6 (capture eluat) | 4.680 | 195 | 913 | 815 | 91 |

Conclusion:

The performance of the release procedure, using 50 mM $CaCl_2$, 50 mM histidine and 100 mM NaCl is not scale dependent. The FVIII recovery increases with more than 9 times for a batch size of 150 kg. In addition, the resulting FVIII solution could be further concentrated through a capture anion exchanger. The volume reduction factor over the capture step was 165 times and the process time was about 4 h.

Example 14: FVIII Release as a Function of Cell Concentration Using 0.1 M and 0.5 M NaCl During cell cultivation, performed as described in example 1, samples from CS13 (clone HEK 293T 48/9H5, vector pTGF8-3) were withdrawn regularly. Cells where counted and the CS sample was divided in two tubes. In one of the tubes a stock solution of 1 M NaCl was added 1+1 to the CS, to a final concentration of 0.5 M. The sample was incubated for 15 minutes where after the tubes were centrifuged at 2500 r/min for 1 minute to remove the cells and the cell supernatant was analyzed for FVIII:C activity. The results are summarized in Table 23.

TABLE 23

| Time (h) | Viable cells, ($10^4$/ml) | FVIII: C × $10^{-6}$/cell, low salt content (0.1M NaCl) | FVIII: C × $10^{-6}$/cell, high salt content (0.5M NaCl) |
|---|---|---|---|
| 0 | 9.7 | NA | NA |
| 26 | 15.0 | 0.5 | 1.8 |
| 70 | 13.4 | 0.2 | 1.0 |
| 93 | 37.2 | 0.8 | 1.7 |
| 141 | 51.0 | 0.9 | 2.4 |
| 163 | 85.0 | 1.0 | 2.9 |
| 192 | 157 | 0.4 | 2.5 |
| 215 | 118 | 0.4 | 3.1 |

NA: not analyzed.

Conclusion:

The example shows clearly that FVIII is bound to the surfaces on the cell during cell cultivation. The level of FVIII within the low salt harvest is almost unchanged when the cell concentration increases. Whereas within the high salt harvest, FVIII increase follow the increase in cell concentration, as expected, if no or minor interaction with the cell membrane occurs.

Example 15: Stability of FVIII Containing Cell Supernatant with Different Calcium Concentration A cell suspension (CS14) cultivated according to example 1 (clone HEK 293T 48/9H5, vector pTGF8-3), was harvested separating the cells with centrifugation. The cell free supernatant (pH 7) was added different amounts of calcium chloride. The solution was stored in room temperature and samples were withdrawn and frozen −70° C. after 0, 6 and 24 h. The FVIII stability was followed analyzing FVIII:C. The results are summarized in Table 24.

TABLE 24

| Addition | 0 h | 6 h | 24 h | 48 h |
|---|---|---|---|---|
| 0 mM calcium | 100% | 95% | 67% | 48% |
| 2 mM calcium | 100% | 89% | 92% | 85% |
| 10 mM calcium | 100% | 95% | 101% | 93% |
| 50 mM calcium | 100% | 98% | 100% | 97% |

Conclusion:

Calcium has a stabilizing effect on FVIII in cell supernatant medium. It is known in the literature that calcium is an important component for the structure, function and stability of FVIII in the range 1-50 mM (Wang et al., International Journal of Pharmaceutics 259 (2003) 1-15). Thus, the use of calcium chloride as a release substance for FVIII, according to the invention has double effects: releasing substance and stabilizing of FVIII.

Moreover, as can be seen from Western blot analysis in FIG. 3B, no significant change could be detected in the molecular mass distribution of crude FVIII, using different release substances of the invention and compared with normal harvest conditions (about 0.1 M NaCl).

Example 16: Production of Cell Lines for an Adsorption Study

In the following examples 16 to 20 an adsorption study is provided where FVIII was added to mock (=cells without FVIII production capacity) HEK-293F cells and also BHK cells. The result of these experiments shows that after addition of FVIII to the cell suspension, the amount of FVIII in the cell supernatant decreased with time, indicating adsorption to the cell surface. An identical experiment, with the exception that IgG was used instead of FVIII, was performed with the HEK-293F cells. This experiment showed that IgG did adsorb to the HEK 293F cells cultivated under serum free conditions.

Cell Line:

The expression cell line is based on the serum free adapted cell line HEK 293F (or shortly 293F, Invitrogen # R790-07). This cell line was originally generated by transformation of human foetal kidney cells with sheared adenovirus type 5 DNA (F. L. Graham et al., J. Gen. Virol. 36(1), 59-74 (1974)). Species: Human; Tissue: foetal kidney; Morphology: Epithelial like; Karyotype: The karyotype of 293F cells is not specified; the karyotype of 293 cells (ECACC #85120602), however, is known and described as 2n=46, hypotriploid, model chromosome number: 64.

Normal Expression Plasmid:

As expression plasmid a vector of the pcDNA3.1 family (Invitrogen) was used. The vector contain the expression cassette for B-domain deleted human clotting factor VIII with the linker peptide of SEQ ID NO:9 (SEQ ID NOs:4 and 6, respectively). It has three amino acid residue exchanges at position 162, 2011 and 2223 (relative to the full length sequence shown in SEQ ID NO:2). The expression of the BDDrFVIII is controlled by a CMV promoter. This promoter in connection with the SV40 intron and the polyadenylation site provide high-level recombinant protein production. The resistance against two antibiotics provides an efficient tool for clone selection after transfection. To be able to produce host cell proteins without FVIII (for development of antibody based analytical method for host cell proteins) a so-called mock cell line was produced where the FVIII gene was excluded out from the plasmid. This non FVIII producing cell line was also used for FVIII (and IgG) adsorption studies.

Cultivation:

Static cultivation of cells was done in TC-flasks of different size. All medium used was serum free. Bottles were used for dynamic cultivation. For agitation purpose the bottles where placed on a horizontal shaker situated within the incubator. All incubators were set to 5% carbon dioxide, 37° C. and 95% relative humidity.

Description of Analysis:

Factor VIII:C Screening Method Based on Coatest:

The method is based on the two-stage principle, and was performed using micro plate technique. In stage one, activated factor X (Xa) is generated via the intrinsic pathway where factor VIII: C acts as a co-factor. In stage two, Factor Xa is then determined by the use of a synthetic chromogenic substrate, S-2222 in the presence of a thrombin inhibitor 1-2581 to prevent hydrolysis of the substrate by thrombin. The reaction is stopped with acid, and the VIII: C activity, which is proportional to the release of pNA (para-nitroaniline), is determined photo metrically at 405 nm against a reagent blank. The method complies with the requirements in the European Pharmacopoeia. The unit of factor VIII: C is expressed in international units (IU) as defined in the current International Concentrate Standard (IS) established by the World Health Organization (WHO). The routine using buffer containing 1% BSA instead of severe haemophilic plasma for predilutions has been validated.

IqG Elisa:

The IgG concentrations were determined with an ELISA-method, Mouse-IgG ELISA (Roche Applied Science, Germany), according to the manufacturer's instructions. A special catching antibody is bound adsorptively to the wells of microplates. After blocking with Blocking reagent the antibody contained in the sample (e.g., hybridoma-supernatant, ascites dilution, etc.) is bound to the capture antibody during a further incubation step. POD is fixed to the monoclonal antibody using a POD-labeled, balanced mixture of anti-mouse- and anti-mouse-antibodies (immunosorbed Fab-fragments). With the highly sensitive ABTS-perborate system a dark green color is formed in the reaction with the fixed peroxidases. Evaluation is performed using a standard graph.

Example 17: Production of a Laboratory Sample of a B-Domain Deleted FVIII in HEK 293F Cell Line Cell Line:

The expression cell line is based on the serum free adapted cell line HEK 293F (or shortly 293F, Invitrogen # R790-07). This cell line was originally generated by transformation of human foetal kidney cells with sheared adenovirus type 5 DNA (F. L. Graham et al., J. Gen. Virol. 36(1), 59-74 (1974)). Species: Human; Tissue: foetal kidney; Morphology: Epithelial like; Karyotype: The karyotype of 293F cells is not specified; the karyotype of 293 cells (ECACC #85120602), however, is known and described as 2n=46, hypotriploid, model chromosome number: 64.

Expression Plasmid:

As expression plasmid a vector of the pcDNA3.1 family (Invitrogen) was used. The vector contain the expression cassette for B-domain deleted human clotting factor VIII with the linker peptide of SEQ ID NO:9 (SEQ ID NOs:4 and 6, respectively). It has three amino acid residue exchanges at position 162, 2011 and 2223 (relative to the full length sequence shown in SEQ ID NO:2). The expression of the BDDrFVIII is controlled by a CMV promoter. This promoter in connection with the SV40 intron and the polyadenylation site provide high level recombinant protein production. The resistance against two antibiotics provides an efficient tool for clone selection after transfection.

Transfection:

Immediately following revitalization, adherent 293F cells were transfected with pcDNA3.1 using the calcium phosphate method (C. Chen et al., Mol. Cell Biol. 7(8), 2745-2752 (19887)). Selection with hygromycin (200 ng/ml) started 72 h after transfection. After 10 days under selection, individual hygromycin-resistant clones were isolated, expanded and subcloned through two consecutive rounds of single cell cloning. Recombinant FVIII production was quantified in the supernatant of hygromycin-resistant clones using ELISA and aPTT assays. This procedure led to the selection of clone No. 293F 4/24K.

Cultivation:

Static cultivation of cells was done in TC-flasks of different size. All medium used was serum free. Bottles and up to 100 L bioreactors were used for dynamic cultivation. For agitation purpose the bottles where placed on a horizontal shaker situated within the incubator. All incubators were set to 5% carbon dioxide, 37° C. and 95% relative humidity.

Example 18: Adsorption of FVIII to Serum Free Cultivated HEK 293F Cells

A HEK 293F cell suspension was cultivated under serum free conditions according to example 16. FVIII was added as described in Table 25 and the cell suspension ($1\times10^6$ cells/ml) was cultivated as before, sample of cell free supernatant was taken after 1, 5 and 24 h (controls of respectively FVIII solution added to medium without cells and incubated under the same conditions as the cell suspension, were taken at the same time). Samples where frozen and analysed for FVIII:C activity. The results are summarized in Table 26.

TABLE 25

| FVIII addition | Type of factor |
|---|---|
| A, 100 IU/ml | Full length plasma derived FVIII stabilised with vWf* |
| B, 100 IU/ml | B-domain deleted recombinant FVIII** |

*Octanate ® (Octapharma)

**A laboratory sample of B-domain deleted FVIII, purity 90%, no vWf content, cultivated according to example 17

TABLE 26

| FVIII | FVIII: C [IU/ml] | Change* |
|---|---|---|
| A, 1 h | 50.1 | 7.5% |
| A, 5 h | 48.5 | 4.0% |
| A, 24 h | 27.4 | −41.4% |
| B, 1 h | 27.6 | 6.4% |
| B, 5 h | 15.0 | −42.2% |
| B, 24 h | 8.5 | −48.3% |

*After compensation with control

Conclusion:

FVIII adsorbs to cell surface under cultivation premises. Tendency that recombinant B-domain deleted FVIII adsorbs faster compared to full-length plasma FVIII stabilised with von Willebrandt factor.

Example 19: Adsorption of FVIII to BHK Cells

ABHK-21 cells (ATCC 13001) where cultivated on Cytodex-3 in 250 ml spinner flask (Corning). The medium used was D-MEM with 10% FBS. Before use, the cell supernatant was exchanged with 3 volumes of serum free buffer (PBS-A with 0.03% w/w EDTA) to remove the serum components. FVIII was added as described in Table 27 and the cell suspension ($1.5\times10^6$ cells/ml) was cultivated as before, sample of cell free supernatant was taken after 1, 5 and 24 h (controls of respectively FVIII solution added to medium without cells and incubated under the same conditions as the cell suspension, were taken at the same time). The results are summarized in Table 28.

TABLE 27

| FVIII addition | Type of factor |
|---|---|
| A, 100 IU/ml | Full length plasma derived FVIII stabilised with vWf* |

*Octanate ® (Octapharma)

TABLE 28

| FVIII | FVIII: C [IU/ml] | Change* |
|---|---|---|
| A, 1 h | 50.6 | 8.4% |
| A, 5 h | 45.6 | −2.3% |
| A, 24 h | 30.1 | −35.5% |

*After compensation with control

Conclusion:

FVIII adsorbs to BHK cell surface under cultivation premises.

Example 20: Adsorption of IGG to Serum Free Cultivated HEK 293F Cells

A HEK 293F cell suspension was cultivated 6 days under serum free conditions according to example 16. To the cells ($0.9\times10^6$ cells/ml) different amounts of IGG (lyophilised IgG standard (Roche Diagnostics) diluted in PBS to three different solutions of 10300, 1030, and 103 ng/ml). The different IgG stem solutions were portioned out into micro tubes and one part (0.25 ml) of these standard solutions were mixed with one part (0.25 ml) of the resuspended cells. This led to a 2-fold dilution of the IgG standards and therefore the expected IgG concentrations was 5150, 515 and 51.5 ng/ml. As positive controls, one part of each IgG standard solution was mixed with one part of culture medium and as negative controls one part of the resuspended cells was mixed with one part of pure PBS-A, containing no IgG. After 1 h of incubation the samples were centrifuged at 6000 rpm and the supernatants were collected and analysed. Sample experiments were repeated 6 times and control experiments were repeated at least 9 times. Samples where frozen and analysed for IGG content.

Results:

An overview of the results of the experiments where IgG standards of three different concentrations where incubated together with HEK cells is presented in Tables 29 and 30.

Even though the accuracy of the result after incubation with 5150 ng/ml standard solution is not adequate, −5.02±20.0%, all results show a decrease in IgG concentration after incubation. With the other two standard solutions, 515 and 51.5 ng/ml, the decrease was −26.0+9.10% and −15.8±11.5% respectively. This reduction of IgG in the sample supernatants, compared to the positive controls, indicates that IgG has adsorbed to HEK cells.

TABLE 29

Mean IgG concentrations and standard deviations for controls and samples in adsorption experiments. Three different IgG concentrations (5150 ng/ml, 515 ng/ml and 51.5 ng/ml) were incubated together with fresh medium (in controls) and HEK suspension containing $0.9 \times 10^6$ HEK cells/ml (in samples).

| | IgG conc. before incubation [ng/ml] | Mean IgG conc. after incubation, μ [ng/ml] | Standard dev. |
|---|---|---|---|
| Positive controls: | 5150 | 4860 | 945 |
| (no cells) | 515 | 619 | 59.1 |
| | 51.5 | 49.7 | 5.57 |
| Negative controls: | 0 | <7.00 | — |
| ($0.9 \times 10^6$ cells/ml) | | | |
| Samples: | 5150 | 4610 | 337 |
| ($0.9 \times 10^6$ cells/ml) | 515 | 458 | 30.6 |
| | 51.5 | 41.9 | 4.98 |

TABLE 30

95% confidence intervals for $\mu_s - \mu_c$, where $\mu_s$ is the mean IgG concentration in the samples and $\mu_c$ is the mean IgG concentration in the controls for each stem solution respectively.

| IgG concentration before incubation | 95% conf. interv. for $\mu_s - \mu_c$ | | Change in amount of IgG per cell |
|---|---|---|---|
| [ng/ml] | [ng/ml] | [%] | [pg/cell] |
| 5150 | −244 ± 970 | −5.02 ± 20.0 | −0.542 ± 2.17 |
| 515 | −161 ± 56.3 | −26.0 ± 9.10 | −0.357 ± 0.124 |
| 51.5 | −7.85 ± 5.72 | −15.8 ± 11.5 | −0.0174 ± 0.0131 |

Conclusion:

IGG binds to HEK 293 Cells cultivated under serum free conditions.

Example 21: Production of Expression Cell Line

Cell line: The expression cell line is based on the serum free adapted cell line HEK 293F (or shortly 293F, Invitrogen # R790-07). This cell line was originally generated by transformation of human foetal kidney cells with sheared adenovirus type 5 DNA (F. L. Graham et al., J. Gen. Virol. 36(1), 59-74 (1974)). Species: Human; Tissue: foetal kidney; Morphology: Epithelial like; Karyotype: The karyotype of 293F cells is not specified; the karyotype of 293 cells (ECACC #85120602), however, is known and described as 2n=46, hypotriploid, model chromosome number: 64.

Expression Plasmid:

As expression plasmid a vector of the pcDNA3.1 family (Invitrogen) was used. The vector contain the expression cassette for B-domain deleted human clotting factor VIII with the linker peptide of SEQ ID NO:9 (SEQ ID NOs:4 and 6, respectively). It has three amino acid residue exchanges at position 162, 2011 and 2223 (relative to the full length sequence shown in SEQ ID NO:2). The expression of the BDDrFVIII is controlled by a CMV promoter. This promoter in connection with the SV40 intron and the polyadenylation site provide high level recombinant protein production. The resistance against two antibiotics provides an efficient tool for clone selection after transfection.

Transfection:

Immediately following revitalization, adherent 293F cells were transfected with pcDNA3.1 using the calcium phosphate method (C. Chen et al., Mol. Cell Biol. 7(8), 2745-2752 (19887)). Selection with hygromycin (200 ng/ml) started 72 h after transfection. After 10 days under selection, individual hygromycin-resistant clones were isolated, expanded and subcloned through two consecutive rounds of single cell cloning. Recombinant FVIII production was quantified in the supernatant of hygromycin-resistant clones using ELISA and aPTT assays. This procedure led to the selection of clone No. 293F 4/24K.

Cultivation:

Static cultivation of cells was done in TC-flasks of different size. All medium used was serum free. Bottles and up to 100 L bioreactors were used for dynamic cultivation. For agitation purpose the bottles where placed on a horizontal shaker situated within the incubator. All incubators were set to 5% carbon dioxide, 37° C. and 95% relative humidity.

Cell Suspension:

The starting material for harvest experiments is the cell suspension (hereinafter shortly referred to as "CS".). Before use, the cell suspension has been induced with sodium butyrate for at least one day, to improve the productivity of the cells.

Description of Analysis, Factor VIII: C, Screening Method Based on Coatest:

The method is based on the two-stage principle, and was performed using micro plate technique. in stage one, activated factor X (Xa) is generated via the intrinsic pathway where factor VIII: C acts as a co-factor. In stage two, Factor Xa is then determined by the use of a synthetic chromogenic substrate, S-2222 in the presence of a thrombin inhibitor 1-2581 to prevent hydrolysis of the substrate by thrombin. The reaction is stopped with acid, and the VIII: C activity, which is proportional to the release of pNA (para-nitroaniline), is determined photo metrically at 405 nm against a reagent blank. The method complies with the requirements in the European Pharmacopoeia. The unit of factor VIII: C is expressed in international units (IU) as defined in the current International Concentrate Standard (IS) established by the World Health Organization (WHO). The routine using buffer containing 1% BSA instead of severe haemophilic plasma for predilutions has been validated.

Example 22: Harvest Using Different Concentration of Peptone

Different amounts of solid peptone (Soy Peptone A2 SC 19649, Organo Technie, La Courneuve, France) or salts (see, Table 31) were added to 10 ml of a cell suspension ($2.0 \times 10^6$ cells/ml). The cells had been cultivated as described in example 21 and were withdrawn before harvest. The washing substances were dissolved and the suspension was gently mixed (using a rocking mixer) for 1 h at room temperature (21° C.), using 15 ml tubes. The tubes were then centrifuged at 600 r/min for 5 min to remove the cells, where after the cell supernatant was analysed for FVIII:C activity. The results are summarized in Table 31.

TABLE 31

| Wash concentration | FVIII: C [IU/ml]* | FVIII release [IU FVIII: C × $10^{-6}$/cell]* |
|---|---|---|
| Reference, untreated | 1.1 | 0.55 |
| 0.5M NaCl | 6.7 | 3.35 |
| 50 mM $CaCl_2$ | 7.6 | 3.78 |
| 0.5M NaCl + 50 mM $CaCl_2$ | 8.5 | 4.25 |
| 2.5% Peptone | 2.0 | 1.00 |
| 5% Peptone | 3.3 | 1.65 |
| 10% Peptone | 5.9 | 2.95 |
| 20% Peptone | 6.7 | 3.35 |

*Compensated for dilution factors

Conclusion:

Increase of sodium chloride and or calcium chloride or peptone concentration before the harvest significant increase the recovered FVIII compared with untreated sample.

Example 23: Cultivation with and without Low Amount of Peptone and Thereafter Addition of Low Concentration Peptone to Study FVIII Release Under Conditions which can be Used During Cultivation Two different cultivated cell suspensions was used in this experiment, both containing 5 mg/ml insulin (Monotard®, Novo Nordisk) and one also containing 0.2% peptone in the serum free cultivation medium from start. Otherwise the cell suspension was cultivated as described in example 21.

Different amounts of peptone (Soy Peptone A2 SC 19649, Organo Technie, La Courneuve, France) or $CaCl_2$ (namely a 0.5 M solution of $CaCl_2$ to reach a final concentration of 50 mM $CaCl_2$; see table 32) were added to 5 ml of cell suspension ($1.62 \times 10^6$ cells/ml for cell suspension cultivated without peptone and $1.38 \times 10^6$ cells/ml for cell suspension cultivated with 0.2% peptone) The added peptone was a 10% solution dissolved in cultivation medium (with the exception for the 18% peptone experiment in which the peptone was added as solid). After addition of release substances, the suspension was gently mixed (using a rocking mixer) for 1 h at room temperature (21° C.) using 15 ml tubes. The tubes were then centrifuged at 600 r/min for 5 min to remove the cells, where after the cell supernatant was analysed for FVIII:C activity. The results are summarized in Table 32.

TABLE 32

| Added amount of release component at time for harvest | FVIII: C × $10^{-6}$/cell (cultivated with 0.2% peptone)* | FVIII: C × $10^{-6}$/cell (cultivated with 0% peptone)* |
|---|---|---|
| 0 (reference, untreated) | 0.51 | 0.40 |
| 0.2% peptone | 0.51 | 0.41 |
| 0.9% peptone | 0.54 | 0.52 |
| 1.7% peptone | 0.70 | 0.50 |
| 2.9% peptone | 0.72 | 0.53 |
| 18% peptone (high conc. ref.) | 1.71 | 1.57 |
| 50 mM $CaCl_2$ (salt reference) | 1.62 | 1.84 |

*Compensated for dilution factors

Conclusion:

Cultivation with low amounts peptone releases more FVIII from the cell surface compared with cultivation without any added peptone (see sample reference, untreated). This is also valid when small amount of peptone is added 1 h before the harvest. Thus, peptone contributes to the release of FVIII from the cell surface even in relative low concentrations which can be used during the cultivation process without negative effect towards the cells.

SEQUENCE LISTING, FREE TEXT

SEQ ID NO:1: DNA sequence of human factor VIII.
SEQ ID NO:2: Amino acid sequence of human factor VIII.
SEQ ID NO:3: DNA sequence of vector pTGF8-3.
SEQ ID NO:4: Amino acid sequence of B-domain deleted factor VIII as encoded by pTGF8-3.
SEQ ID NO:5: DNA sequence of vector pTGF8-2hyg-s.
SEQ ID NO:6: Amino acid sequence of B-domain deleted factor VIII as encoded by pTGF8-2hyg-s.
SEQ ID NOs: 7 to 9: Linker peptides.
SEQ ID NO:10: DNA sequence of vector pTGF36.
SEQ ID NO:11: Amino acid sequence of human factor IX as encoded by pTGF36.

The invention claimed is:

1. A method for the recombinant production of at least one target protein in eukaryotic cells, which comprises effecting cultivation of eukaryotic cells, being capable of expression of said at least one target protein, under protein-free conditions and subjecting a suspension of said cells, prior to separation of the protein from the cells, to a non-physiologically increased concentration of at least one ionic substance selected from the group consisting of NaCl and $CaCl_2$); wherein at least a subset of cells in said suspension remains viable in order to allow for reculture of the cells; and wherein:

(i) NaCl is added to raise its concentration in the cell suspension to range from 0.1 M to 0.6 M;

(ii) NaCl is added to raise its concentration in the cell suspension to about 0.5 M;

(iii) $CaCl_2$ is added to raise its concentration in the cell suspension to more than 0.002 M;

(iv) $CaCl_2$ is added to raise its concentration in the cell suspension to range from more than 0.002 M to 0.5 M;

(v) $CaCl_2$ is added to raise its concentration in the cell suspension to range from 0.05 M to 0.5 M; or (vi) $CaCl_2$ is added to raise its concentration in the cell suspension to about 0.1 M.

2. The method of claim 1, wherein the adjusting of the concentration of the cell suspension is effected by adding to the cell suspension a release composition comprising said at least one ionic substance, said release composition (i) being added to the cell suspension in solid or liquid form; and/or (ii) being added to the cell suspension up to 3 days prior to the separation of the protein; and/or (iii) being added to the cell suspension at the start and kept constant during continuous cultivation and harvest of the protein; and/or (iv) being added to the cell suspension during harvest periods and in between exchanged with physiological conditions, during the continuous cultivation and harvest process of the protein; and/or (v) being directly added to the culture broth or being added to the cells or a suspension of the cells isolated from the culture broth; and/or (vi) being gradually added to reach the final concentration within 1-2000 minutes; and/or (vii) being added with diafiltration technique.

3. The method of claim 1, wherein (i) the target protein(s) is/are selected from plasma proteins, peptide hormones, growth factors, cytokines and antibodies, wherein the proteins are plasma proteins the plasma proteins are selected from human and animal blood clotting factors including fibrinogen, prothrombin, thrombin, FX, Fa, FIX, FIXa, FVII, FVIIa, FVIII, FVIIIa, FXI, FXIa, FXII, FXIIa, FXIII and FXIIIa, muteins of clotting factors, von Willebrand factor, transport proteins including albumin, transferrin, ceruloplasmin, haptoglobin, hemoglobin and hemopexin, protease inhibitors including ß-antithrombin, α-antithrombin, α2-macroglobulin, Cl-inhibitor, tissue factor pathway inhibitor (TFPI), heparin cofactor II, protein C inhibitor (PAI-3), Protein C and Protein S, antiangionetic proteins including latent-antithrombin, highly glycosylated proteins including α-1-acid glycoprotein, antichymotrypsin, inter-α-trypsin inhibitor, α-2-HS glycoprotein and C-reactive protein and other proteins including histidine-rich glycoprotein, mannan binding lectin, C4-binding protein, fibronectin, GC-globulin, plasminogen, erythropoeitin, interferon, tumor factors, tPA, gCSF and derivatives and muteins thereof, domain deleted factor VIII protein, and a factor VIII mutein having SEQ ID NO:4 or 6; and/or (ii) the eukaryotic cells are isolated cells or isolated tissue cells of invertebrates, including insects and worms, of plants, and cells of lower eukaryotes including yeast, of vertebrates, including mammals and fish including human cell and rodent cells, immortalized human fetal kidney cells including HEK293 deposited with the ATCC receiving the ATCC accession number CLR-1573, HEK293 T deposited with the DSM and receiving the DSM accession number ATCC 2494, 293 H and 293 freestyle 293 F cells, CHO cell, Cos cell, hybridoma cell, and NSO myeloma cell; and/or (iii) the mammalian cells are stably transfected with an expression cassette carrying the gene coding for the target protein(s); and/or (iv) the ionic substance(s) is/are added to reach the equilibration balance within protein and cell surface, enough to disrupt the ionic binding and release bound proteins from the cell surface without destroying the cell; and/or (v) at least one or more ionic substance, is/are added; and/or (vi) no or only small amounts of non-ionic detergents are added to the suspension and/or are present in an ionic release composition; and/or (vii) the least one ionic substance further comprises a buffering substance to stabilize the pH; and/or (viii) the pH of the cell suspension when subjected to the increased concentration of the at least one ionic substance is in the range of stability for the selected protein, for FVIII it is from about 6.0 to 7.5; and/or (ix) by harvesting of the protein the viability of the cells is maintained, and after harvest the non naturally increased concentration of the ionic substance is reduced or the cells are transferred into fresh culture medium, to enable a continuous cyclic production process of the protein using the same cells; and/or (xi) the ionic release composition is selected to contain at least one substance aimed to stabilize the released proteins.

4. The method of claim 1, which comprises one or more of the following steps:

(a) cultivating the cells in a culture medium;

(b) separating the culture medium from the cultivated cells, resulting in two separate fractions, a fraction of cultivated cells and a fraction of liquid medium;

(c) contacting or suspending the fraction of cultivated cells with a release composition comprising a non-physiologically increased concentration of at least one ionic substance selected from NaCl and $CaCl_2$;

(d) removing the culture medium from the cells, resulting in two separate fractions, a fraction of cells and a fraction of release composition;

(e) isolating the recombinant protein from the fraction of the release composition; and (f) suspending the fraction of cells of (d) above in culture medium and reculture.

5. The method of claim 4, wherein (i) the cultivation of the cells is effected in suspension culture or adherent culture;

(ii) the separation of the medium from the cultivated cells in steps (b) and (d) is effected by centrifugation, filtration, diafiltration, tangential filtration, dead end filtration, micro filtration, electrical fields, magnetic fields and ultra filtration; and/or (iii) the isolation of the protein from the medium and its purification is effected by using at least one technique selected from immuno-affinity chromatography, affinity chromatography, protein precipitation, buffer exchanges, ionic exchange chromatography, hydrophobic interaction chromatography, mixed mode hydrophobic/ion exchange chromatography media, chelating chromatography, carbohydrate affinity like lectin or heparin affinity chromatography, size-exclusion chromatography, electrophoresis, dialysis, polyethylene glycol precipitation, ammonium sulphate precipitation, ethanol precipitation, hydroxy apatite adsorption, filter membrane adsorption, ligands coupled to magnetic particles; and/or (iv) the carrier used for the chromatography purification, is selected from resins, particles, beads, membranes, hollow fiber or similar; and/or (v) the isolation of the protein comprises a capture step, where the product is bound and cell cultivation media and release composition is washed away; and/or (vi) steps (d) and (e) are effected by mixing the cell suspension with a chromatographic medium which binds the product and thereafter the chromatography media is removed from the cell suspension, using centrifugation, filtration, dead end filtration, tangential filtration, micro filtration, electrical fields, magnetic fields and/or ultra filtration.

6. The method of claim 1, (i) which is performed under sterile conditions; and/or (ii) wherein the medium and/or the purified protein is subjected to a virus inactivation and/or removal step.

7. The method of claim 1, wherein (i) two or more ionic substances are mixed to form an ionic release composition; and/or (ii) the concentration of a mixture of ionic substances needed to reach the desired release of proteins is determined by dividing the theoretic amount of ionic substances, being based on the optimal release concentration for each ionic release substance when used separately, with the number of substances; and/or (iii) by a combination of ionic substances, due to combinatorial effects of the different ionic substances, a lower amount of each ionic substance is required to achieve the protein releasing properties of the composition and to provide simultaneously acceptable cultivation conditions for the cells; and/or (iv) the ionic release composition is selected so that at least one component acts as an stabilizer for the released protein being active before and/or after the separation of protein and cells.

8. The method of claim 1, wherein the cell suspension is processed with a micro filtration system where the pore in the filter has been chosen to retain the cells and the filtration technique being chosen from dead-end or tangential flow filtration techniques, and wherein a release composition is applied to the cells immediately or with a gradual increase using the diafiltration technique and the cell free product is recovered in the filtrate of said micro filtration system.

9. The method of claim 2, wherein said release composition being added 1 to 24 h prior to the separation of the protein.

10. The method of claim 2, wherein said release composition being added 1 to 120 min prior to the separation of the protein.

11. The method of claim 3, wherein (i) the target protein(s) comprise a factor VIII mutein having SEQ ID NO:4 or 6; and/or (ii) the eukaryotic cells are isolated cells or isolated tissue cells including HEK293 deposited with the ATCC receiving the ATCC accession number CLR-1573, HEK293 T deposited with the DSM and receiving the DSM accession number ATCC 2494, 293 H and 293 freestyle 293 F cells, CHO cell, Cos cell, hybridoma cell, and NSO myeloma cell; and/or (iii) the mammalian cells are stably transfected with an expression cassette carrying the gene coding for the target protein(s); and/or (iv) in the ionic substance(s) the amino acid is lysine, histidine or arginine, and the peptone is a soy peptone; and/or (v) the ionic substance(s) is/are added to reach the equilibration balance within protein and cell surface, enough to disrupt the ionic binding and release bound proteins from the cell surface without destroying the cell; and/or (vi) the release composition is free of non-ionic detergents; and/or (vii) the least one ionic substance further comprises a buffering substance selected from Goods buffer substances, including HEPES, MES and TRIS; and/or (viii) the pH of the cell suspension when subjected to the increased concentration of the at least one ionic substance is in the range of stability for the selected protein, for FVIII it is from about 6.0 to 7.5; and/or (ix) by harvesting of the protein the viability of the cells is maintained, and after harvest the non naturally increased concentration of the ionic substance is reduced or the cells are transferred into fresh culture medium, to enable a continuous cyclic production process of the protein using the same cells; and/or (xi) the ionic release composition is selected to contain at least one substance aimed to stabilize the released proteins.

12. The method of claim 6, wherein the capture step utilizes a chromatography media.

* * * * *